United States Patent [19]

Gottstein et al.

[11] 4,297,489

[45] Oct. 27, 1981

[54] 7-α-AMINO-SUBSTITUTED ACYLAMINO-3-(1-CARBOXYMETHYLTET-RAZOL-5-YLTHIOMETHYL)-3-CEPHEM-4-CARBOXYLIC ACIDS

[75] Inventors: William J. Gottstein, Fayetteville; Murray A. Kaplan, Syracuse; Alphonse P. Granatek, Baldwinsville, all of N.Y.

[73] Assignee: Bristol-Myers Company, New York, N.Y.

[21] Appl. No.: 590,971

[22] Filed: Jun. 27, 1975

Related U.S. Application Data

[63] Continuation-in-part of Ser. No. 502,991, Sep. 3, 1974, abandoned.

[51] Int. Cl.³ .............. C07D 501/54; C07D 501/56; A61K 31/545
[52] U.S. Cl. .............................. 544/27; 260/340.2; 260/453 AL; 260/544 N; 424/246; 542/419; 544/21; 544/23; 544/26; 546/114; 548/251; 549/64; 549/65; 549/66; 560/24; 560/29; 560/115; 562/444; 562/507
[58] Field of Search .................... 544/26, 27

[56] References Cited

U.S. PATENT DOCUMENTS

| | | | |
|---|---|---|---|
| 3,819,623 | 6/1974 | Takano et al. | 544/27 |
| 4,068,074 | 1/1978 | Murakami et al. | 544/27 |
| 4,092,476 | 5/1978 | Bentley et al. | 544/23 |
| 4,098,888 | 7/1978 | Ochiai et al. | 424/246 |
| 4,100,346 | 7/1978 | Gottstein et al. | 544/27 |
| 4,113,944 | 9/1978 | Kai et al. | 544/27 |
| 4,118,563 | 10/1978 | Lim et al. | 544/26 |
| 4,160,086 | 7/1979 | Burton et al. | 544/26 |
| 4,172,196 | 10/1979 | Gottstein et al. | 544/26 |
| 4,182,863 | 1/1980 | Gottstein et al. | 544/26 |
| 4,183,925 | 1/1980 | Baxter et al. | 424/246 |
| 4,205,166 | 5/1980 | Kamiya et al. | 544/27 |
| 4,220,644 | 9/1980 | Berges | 424/246 |

FOREIGN PATENT DOCUMENTS

| | | |
|---|---|---|
| 819209 | 11/1974 | Belgium . |
| 47-05550 | 2/1972 | Japan . |
| 7410059 | 1/1975 | Netherlands . |

*Primary Examiner*—Donald G. Daus
*Assistant Examiner*—Diana G. Rivers
*Attorney, Agent, or Firm*—Herbert W. Taylor, Jr.

[57] ABSTRACT

Certain 7-acylamido-3-(1-carboxy-loweralkyl-tetrazol-5-ylthiomethyl)-3-cephem-4-carboxylic acids and their salts and easily hydrolyzed esters of the 4-carboxyl group were synthesized and found to be potent antibacterial agents which exhibited good aqueous solubility. In a preferred embodiment the 7-substituent was 2'-aminomethylphenylacetamido.

15 Claims, No Drawings

7-α-AMINO-SUBSTITUTED ACYLAMINO-3-(1-CARBOXYMETHYLTETRAZOL-5-YLTHIOMETHYL)-3-CEPHEM-4-CARBOXYLIC ACIDS

CROSS-REFERENCE TO RELATED APPLICATIONS

This application is a continuation-in-part of a copending application Ser. No. 502,991 filed Sept. 3, 1974, now abandoned.

BACKGROUND OF THE INVENTION

1. Field of the Invention

The cephalosporins of the present invention in general possess the usual attributes of such compounds and are particularly useful in the treatment of bacterial infections.

2. Description of the Prior Art

The cephalosporins are a well-known group of semisynthetic antibacterial agents made originally, for example, by acylation of the 7-amino group of the nucleus 7-aminocephalosporanic acid (7-ACA) and later by similar acylation of nuclei derived therefrom, as by modification of its substituent at the 3-position. Various reviews have appeared in the scientific literature (e.g. Cephalosporins and Penicillins-Chemistry and Biology, edited by Edwin H. Flynn, Academic Press, New York, 1972, and particularly pages 554–569) and in the patent literature, e.g. as in U.S. Pat. Nos. 3,687,948; 3,741,965; 3,743,644; 3,759,904; 3,759,905; 3,766,175; 3,766,906; 3,769,281; 3,796,801; 3,799,923; 3,812,116; 3,813,388; 3,814,754 and 3,814,755 (all U.S. Class 260-243C).

Issued patents on 3-thiolated cephalosporins in which the 7-substituent is (a) α-Amino-α-phenylacetamido include U.S. Pat. Nos. 3,641,021, 3,734,907, 3,687,948, 3,741,965, 3,757,015, 3,743,644, Japan No. 71/24400 (Farmdoc 46374S), Belgium No. 776,222 (Farmdoc 38983T; U.K. No. 1,328,340 which includes various substituents on the benzene ring), Belgium No. 772,592 (Farmdoc 19696T; U.S. Pat. Nos. 3,687,948, 3,734,907 and 3,757,012), West Germany No. 2,202,274 (Farmdoc 50428T) corresponding to U.S. Pat. No. 3,759,904, Netherlands No. 7205644 (Farmdoc 76309T; U.S. Pat. No. 3,757,014); and (b) o-, m- or p-aminoethoxyphenylacetamido as Netherlands 72/13968 (Farmdoc 24740U) corresponding to U.S. 3,759,905 and (c) o-aminomethylphenylacetamido as Netherlands No. 72/06326 (Farmdoc 76374T) (which also reviews the older patent literature concerning substituted 7-phenylacetamidocephalosporanic acids) corresponding to U.S. Pat. Nos. 3,766,176 and 3,766,175; and (d) N-(phenylacetimidoyl)aminoacetamido as U.S. Pat. No. 3,692,779; and (e) α-amino-α-(1,4-cyclohexadienyl)acetamido as in Belgium No. 776,222 (Farmdoc 38983T; U.K. No. 1,328,340).

Additional similar disclosures are found in U.S. Pat. No. 3,692,779 (Belgium No. 771,189; Farmdoc 12819T), Japan No. 72/05550 (Farmdoc 12921T), Japan No. 72/05551 (Farmdoc 12922T), U.S. Pat. No. 3,719,673 (Belgium No. 759,570; Farmdoc 39819S), Belgium No. 793,311 (Farmdoc 39702U) and Belgium No. 793,191 (Farmdoc 39684U).

Issued disclosures of 3-thiolated cephalosporins in which the 7-substituent is 7-mandelamino (7-α-hydroxyphenylacetamido) are found, for example, in U.S. Pat. No. 3,641,021, France No. 73.10112, U.S. Pat. No. 3,796,801, Great Britain No. 1,328,340 (Farmdoc 38983T), U.S. Pat. No. 3,701,775, Japan No. 4844293 (Farmdoc 55334U) and in Hoover et al., J. Med. Chem. 17(1), 34–41 (1974) and Wick et al., Antimicrobial Ag. Chemo., 1(3), 221–234 (1972).

U.S. Pat. No. 3,819,623 (and, for example, also U.K. No. 1,295,841 and West Germany No. 1,953,861) discloses specifically and with working details the preparation of 2-mercapto-1,3,4-thiadiazole-5-acetic acid and its conversion to 7-(1H-tetrazol-1-ylacetamido)-3-(5-carboxymethyl-1,3,4-thiadiazol-2-ylthiomethyl)-3-cephem-4-carboxylic acid which is also disclosed in West Germany Offenlegungsschrift No. 2,262,262.

SUMMARY OF THE INVENTION

The present invention provides the compounds having the structure:

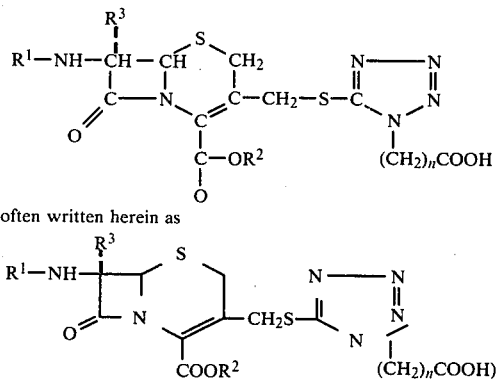

(often written herein as

wherein $R^1$ is acyl or hydrogen and n is an integer of 1 to 9 inclusive, $R^3$ is H or methoxy, and $R^2$ is hydrogen or the group having the formula $$-CH{\overset{W}{\underset{Z}{\diagup\!\!\!\diagdown}}}$$

wherein, when W represents hydrogen, Z represents (lower)alkanoyl, benzoyl, naphthoyl, furoyl, thenoyl, nitrobenzoyl, methylbenzoyl, halobenzoyl, phenylbenzoyl, N-phthalimido, N-succinimido, N-saccharino, N-(lower)alkylcarbamoyl, (lower)alkoxy, (lower)alkylthio, phenoxy, carbalkoxy, carbobenzoxy, carbamoyl, benzyloxy, chlorobenzyloxy, carbophenoxy, carbo-tert.-butoxy or (lower)alkylsulfonyl, and when W represents carbalkoxy, Z represents carbalkoxy and, when W represents phenyl, Z represents benzoyl or cyano or wherein W and Z taken together represent 2-oxocycloalkyl containing 4 to 8 carbon atoms inclusive. In the preferred embodiments of this invention $R^2$ is hydrogen, pivaloyloxymethyl, acetoxymethyl, methoxymethyl, acetonyl, phenacyl, p-nitrobenzyl, β,β,β-trichloroethyl, 3-phthalidyl or 5-indanyl.

As set forth below in more detail the present invention also provides salts of these acids. The stereochemistry of the bicyclic nucleus is that found in Cephalosporin C.

Acyl ($R^1$) includes, but is not limited to, the groups having the structures:

(i) $R^uC_nH_{2n}CO-$ where $R^u$ is aryl (carbocyclic or heterocyclic), cycloalkyl, substituted aryl, substituted cycloalkyl, or a non-aromatic or mesoionic heterocyclic group, and n is an integer from 1–4. Examples of this group include phenylacetyl; substituted phenylacetyl, e.g. fluorophenylacetyl, nitrophenylacetyl, aminophenylacetyl, β-(o-aminomethylphenyl)-propionyl, o-aminomethylphenylthioacetyl, o-, m- and p-guanidinophenylacetyl, o-, m- and p-aminomethylphenylacetyl, acetoxyphenylacetyl, methoxyphenylacetyl, methylphenylacetyl, or hydroxyphenylacetyl; N,N-bis-(2-chloroethyl)aminophenylpropionyl; thien-2- and -3-acetyl; 4-isoxazolyl- and substituted 4-isoxazolylacetyl; 1-cyclohexenylacetyl, 2-aminomethyl-1-cyclohexenylacetyl, 1,4-cyclohexadienylacetyl, 2-aminomethyl-1,4-cyclohexadienylacetyl; pyridylacetyl; tetrazolylacetyl (other heterocyclic-acetyl groups of this type are disclosed in U.S. Pat. Nos. 3,819,623 and 3,516,997) or a sydnoneacetyl group as disclosed in U.S. Pat. Nos. 3,681,328; 3,530,123 and 3,563,983. The substituted 4-isoxazolyl group may be a 3-aryl-5-methyl isoxazol-4-yl group, the aryl group being, e.g. phenyl or halophenyl, e.g. chloro- or bromo-phenyl. An acyl group of this typ is 3-o-chlorophenyl-5-methyl isoxazol-4-yl-acetyl and another is that in which isoxazol is replaced by isothiazole as disclosed in U.S. Pat. No. 3,551,440. Other acyl groups of this type include cyanoacetyl (and similar compounds disclosed in U.S. Pat. No. 3,719,673), 3,5,7-triaza-1-azonia-1-adamantyl)acetyl (as disclosed in U.S. Pat. No. 3,720,669), m-aminopyridiniumacetyl (as disclosed in U.S. Pat. No. 3,757,013), o-, m- and p-(2'-aminoethoxy)phenylacetyl (as disclosed in U.S. Pat. No. 3,759,905), 4,5-dimethoxycarbonyl-1,2,3-triazol-1-ylacetyl or 4-cyano-1,2,3-triazol-1-ylacetyl (as disclosed in U.S. Pat. No. 3,821,206), imidazol-(1)-acetyl (as disclosed in U.S. Pat. No. 3,632,810), p-aminomethylphenylacetyl (as disclosed in U.S. Pat. No. 3,382,241), o-aminomethyl-p-hydroxyphenylacetyl (as disclosed in U.S. Pat. No. 3,823,141), β-(o-aminomethylphenyl)propionyl (as disclosed in U.S. Pat. No. 3,813,391), α-amino-2,4,6-cycloheptatrienyl-acetyl (as disclosed in U.S. Pat. No. 3,539,562) and lower alkoxycarbonylacetyl (as disclosed in U.S. Pat. No. 3,557,104);

(ii) $C_nH_{2n+1}CO-$ where n is an integer from 1–7. The alkyl group may be straight or branched, and if desired, may be interrupted by an oxygen or sulphur atom or substituted by, e.g. a cyano group. Examples of such groups include cyanoacetyl, hexanoyl, heptanoyl, octanoyl, butylthioacetyl and trifluoromethylthioacetyl;

(iii) $C_nH_{2n-1}CO-$ where n is an integer from 2–7. The alkenyl group may be straight or branched and, if desired, may be interrupted by an oxygen or a sulphur atom. An example of such is allylthioacetyl;

where $R^u$ has the meaning defined under (i) and in addition may be benzyl, and $R^v$ and $R^w$, which may be the same or different, each represent hydrogen, phenyl, benzyl, phenethyl or lower alkyl. Examples of such groups include phenoxyacetyl, 2-phenoxy-2-phenylacetyl, 2-phenoxypropionyl, 2-phenoxybutyryl, benzyloxycarbonyl, 2-methyl-2-phenoxypropionyl, p-cresoxyacetyl and p-methylthiophenoxyacetyl;

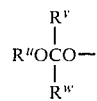

where $R^u$ has the meaning defined under (i) and, in addition, may be benzyl and $R^v$ and $R^w$ have the meanings defined under (iv). Examples of such groups include S-phenylthioacetyl, S-chlorophenylthioacetyl, S-fluorophenylthioacetyl, pyridylthioacetyl, and S-benzylthioacetyl and o-aminomethylphenylthioacetyl, p-aminomethylphenylthioacetyl (as disclosed in U.S. Pat. No. 3,663,540), cyanomethylthioacetyl (as disclosed in France No. 2,194,417), 4-pyridylthioacetyl (as disclosed in U.S. Pat. No. 3,503,967), and heterocyclylmercaptoacetyl (as disclosed in U.S. Pat. No. 3,627,760);

(vi) $R^uZ(CH_2)_mCO-$ where $R^u$ has the meaning defined under (i) and, in addition, may be benzyl, Z is an oxygen or sulphur atom and m is an integer from 2–5. An example of such a group is S-benzylthiopropionyl;

(vii) $R^uCO-$ where $R^u$ has the meaning defined under (i). Examples of such groups include benzoyl, substituted benzoyl (e.g. aminobenzoyl), 4-isoxazolyl- and substituted 4-isoxazolyl carbonyl, cyclopentanecarbonyl, sydnone carbonyl, naphthoyl, and substituted naphthoyl (e.g. 2-ethoxynapthoyl), quinoxalinylcarbonyl and substituted quinoxalinylcarbonyl (e.g. 3-carboxy-2-quinoxalinylcarbonyl). Other possible substituents for benzoyl include alkyl, alkoxy, phenyl or phenyl substituted with carboxy, alkylamido, cycloalkylamido, allylamido, phenyl(lower)alkylamido, morpholinocarbonyl, pyrrolidinocarbonyl, piperidinocarbonyl, tetrahydropyridino, furfurylamido or N-alkyl-N-anilino, or derivatives thereof, and such substituents may be in the 2- or 2- and 6-positions. Examples of such substituted benzoyl groups are 2,6-dimethoxybenzoyl, 2-biphenylcarbonyl, 2-methylaminobenzoyl and 2-carboxybenzoyl. Where the group $R^u$ represents a substituted 4-isoxazolyl group, the substituents may be as set out above under (i). Examples of such 4-isoxazol groups are 3-phenyl-5-methylisoxazol-4-yl carbonyl, 3-o-chlorophenyl-5-methyl-isoxazol-4-yl carbonyl and 3-(2,6-dichlorophenyl)-5-methylisoxazol-4-ylcarbonyl;

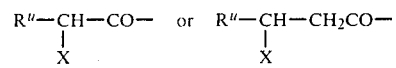

where $R^u$ has the meaning defined under (i) and X is hydrazino, guanidino, ureido, thioureido and substituted thioureido as disclosed in U.S. Pat. No. 3,741,962, allophanamido (as in U.S. Pat. No. 3,483,188), 3-guanyl-1-ureido (see U.S. Pat. No. 3,579,501), cyanamino (see U.S. Pat. No. 3,796,709), amino, substituted amino (e.g. acylamido or a group obtained by reacting the amino group and/or group(s) of the 7-side chain with an aldehyde or ketone, e.g. formaldehyde, acetaldehyde, butyraldehyde, acetylacetone, methyl acetoacetamide, benzaldehyde, salicylaldehyde, acetone, methyl ethyl ketone or ethyl acetoacetate), hydroxy, carboxy (as disclosed in U.S. Pat. Nos. 3,282,926 and U.S. 3,819,601), esterified carboxy (as disclosed, for example, in U.S. Pat. No. 3,635,961), triazolyl, tetrazolyl, cyano, halogeno, acyloxy, (e.g. formyloxy or lower alkanoyloxy) or etherified hydroxy group. Examples of such acyl groups are α-aminophenylacetyl, α-carboxyphenylacetyl, 2,2-dimethyl-5-oxo-4-phenyl-1-imidazolidinyl, α-amino-p-hydroxyphenylacetyl, α-amino-p-acetoxyphenylacetyl, α-hydroxyphenylacetyl and α-formyloxyphenylacetyl or other acyl groups of this type as disclosed, for example, in U.S. Pat. Nos. 3,812,116 and 3,821,017, and α-amino-2- or 3-thienylacetyl (see U.S. Pat. No. 3,342,677) and α-amino-3- or 4- or 5-isothiazolacetyl (see U.S. Pat. No. 3,579,506) and other α-amino and α-hydroxy-heterocyclyl-acetyl groups as disclosed, for example, in U.S. Pat. No. 3,821,207;

$$R^y-\underset{\underset{R^z}{|}}{\overset{\overset{R^x}{|}}{C}}-CO- \quad (ix)$$

where $R^x$, $R^y$ and $R^z$, which may be the same or different, may each represent lower alkyl, phenyl or substituted phenyl. An example of such an acyl group is triphenylcarbonyl;

$$R^u-NH-\overset{\overset{Y}{\|}}{C}- \quad (x)$$

wherein $R^u$ has the meaning defined under (i) and in addition may be hydrogen, lower alkyl or halogen substituted lower alkyl, and Y represents oxygen or sulphur. An example of such a group is $Cl(CH_2)_2NHCO$;

$$(CH_2)_n\underset{CH_2}{\overset{CH_2}{\diagup\diagdown}}\underset{X}{\overset{|}{C}}-CO- \quad (xi)$$

where X has the meaning defined under (viii) above and n is an integer of from 1 to 4. An example of such an acyl group is 1-amino-cyclohexanecarbonyl;

(xii) Amino acyl, for example $R^wCH(NH_2)-(CH_2)_nCO-$ where n is an integer from 1–10, or $H_2N-C_nH_{2n}Ar(CH_2)_mCO$, where m is zero or an integer from 1–10, and n is 0, 1, or 2 $R^w$ is a hydrogen atom or an alkyl, aralkyl or carboxy group or a group as defined under $R^u$ above, and Ar is an arylene group, e.g. p-phenylene or 1,4-naphthylene. Examples of such groups are disclosed in British patent specification No. 1,054,806. A group of this type is the p-aminophenylacetyl group. Other acyl groups of this type include those, e.g. δ-aminoadipoyl derived from naturally occurring amino acids and derivatives thereof, e.g. N-benzoyl-δ-aminoadipoyl;

(xiii) Substituted glyoxylyl groups of the formula $R^y.CO.CO-$ where $R^y$ is an aliphatic, araliphatic or aromatic group, e.g. a thienyl group, a phenyl group, or a mono-, di- or tri-substituted phenyl group, the substituents being, for example, one or more halogen atoms (F, Cl, Br, or I), methoxy groups, methyl groups, or amino groups, or a fused benzene ring as disclosed, for example, in U.S. Pat. Nos. 3,546,219 and 3,573,294;

$$HO_2C-\underset{\underset{\underset{OR^{16}}{|}}{\underset{C=O}{|}}}{\overset{\overset{}{|}}{CH}}-(CH_2)_3-\overset{\overset{O}{\|}}{C}- \quad (xiv)$$

wherein $R^{16}$ is (lower)alkyl or an aralkyl group of the formula $$-(CH_2)_n-\overset{R^{17}}{\underset{R^{18}}{\diagup\diagdown}}$$

wherein n is an integer of 1 to 6 and $R^{17}$ and $R^{18}$ are alike or different and each is H, Cl, Br, F, $NO_2$, (lower)alkyl or (lower)alkoxy;

$$HO_2C-\underset{\underset{\underset{R^{19}}{|}}{\underset{C=O}{|}}}{\overset{\overset{}{|}}{CH}}-(CH_2)_3-\overset{\overset{O}{\|}}{C}- \quad (xv)$$

wherein $R^{19}$ is (lower)alkyl or a group of the formula $$-(CH_2)_n-\overset{R^{17}}{\underset{R^{18}}{\diagup\diagdown}}$$

wherein n is an integer of 0 to 6 and $R^{17}$ and $R^{18}$ are alike or different and each is H, Cl, Br, F, $NO_2$, (lower)alkyl or (lower)alkoxy;

$$HO_2C-\underset{\underset{R^{20}}{|}}{\overset{\overset{}{|}}{CH}}-(CH_2)_3-\overset{\overset{O}{\|}}{C}- \quad (xvi)$$

wherein $R^{20}$ is an α-halo or α,α-dihalo $C_2-C_4$ alkanoyl or $R^{20}$ is N-isobornyloxycarbonyl as disclosed in U.S. Pat. No. 3,819,619 or $R^{20}$ is the group of the formula $$-\underset{\underset{X}{\|}}{\overset{}{C}}-N\overset{R^{21}}{\underset{R^{22}}{\diagdown}} \quad \text{or} \quad -\underset{\underset{O}{\|}}{\overset{}{C}}-O-R^{23}$$

in which $R^{21}$ and $R^{22}$ are each hydrogen, lower alkyl, phenyl, halophenyl, tolyl, lower alkoxyphenyl, or naphthyl, X is oxygen or sulfur, and $R^{23}$ is lower alkyl as disclosed in U.S. Pat. No. 3,819,621 or $R^{20}$ is hydrogen (as in Cephalosporin C);

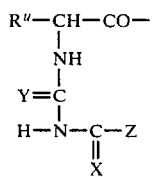 (XVII)

where $R^u$ has the meaning defined under (i), X represents oxygen or imino, Y represents oxygen or sulfur and Z represents (lower)alkyl, cycloalkyl having four, five, six or seven carbon atoms, monohalo(lower)alkyl, dichloromethyl, trichloromethyl, (lower)alkenyl of two to six carbon atoms,

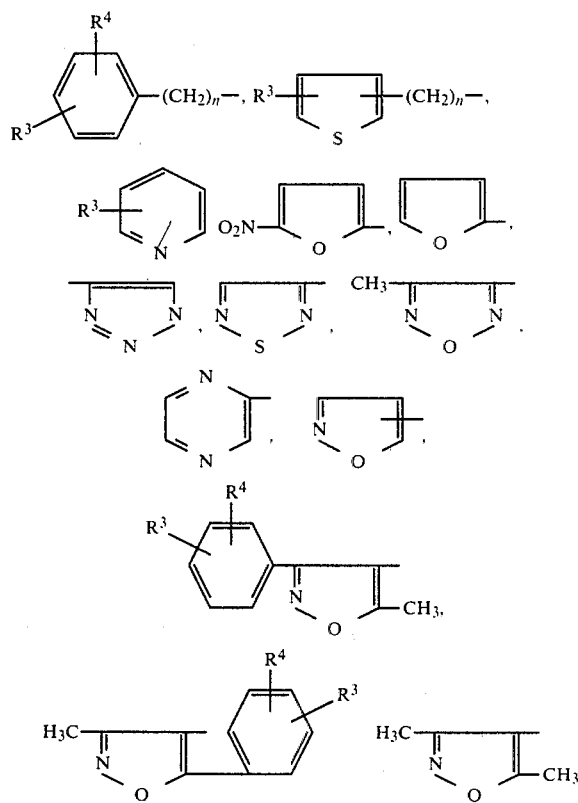

n is an integer from 0 to 3 inclusive and each of $R^3$ and $R^4$ is hydrogen, nitro, di(lower)alkylamine, (lower)alkanoylamino, (lower)alkanoyloxy, (lower)-alkyl (comprising straight and branched chain saturated aliphatic groups having from one to six carbon atoms inclusive), (lower)-alkoxy, sulfamyl, chloro, iodo, bromo, fluoro or trifluoromethyl. In preferred embodiments $R^u$ is phenyl, p-hydroxyphenyl or 2- or 3-thienyl and Z is 2-furyl or phenyl.

Examples are disclosed in U.S. Pat. Nos. 3,687,949 and 3,646,024;

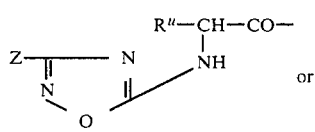 (xviii)

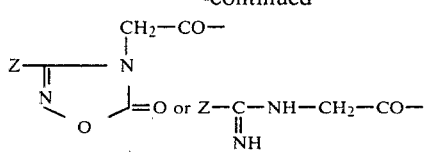

wherein $R^u$ has the meaning defined in (i) and Z has the meaning defined in (xvii). Examples are disclosed in U.S. Pat. Nos. 3,626,024 and 3,692,779;

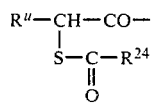 (xix)

where $R^u$ has the meaning defined in (i) and $R^{24}$ is lower alkyl, cycloalkyl, aryl or certain heterocyclic groups. Examples are disclosed in U.S. Pat. No. 3,778,436.

A preferred embodiment of the present invention consists of the compounds of Formula I wherein $R^1$ has the structure

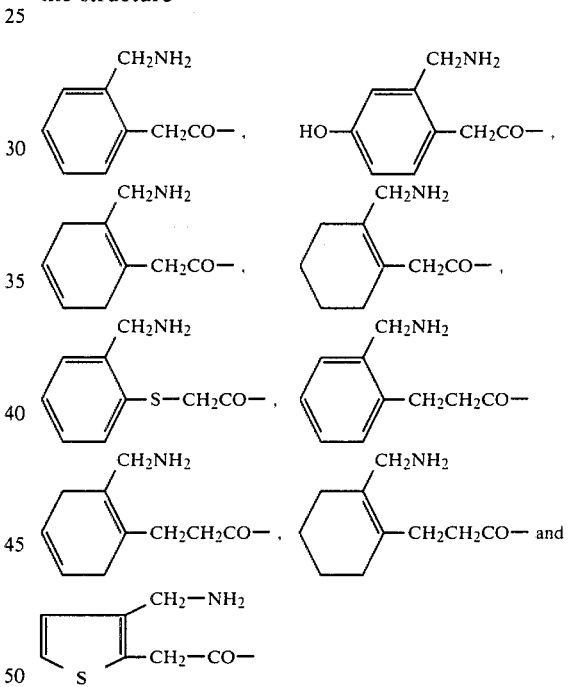

Another preferred embodiment of the present invention consists of the compounds of Formula I having the D configuration in the 7-side chain wherein $R^1$ has the structure

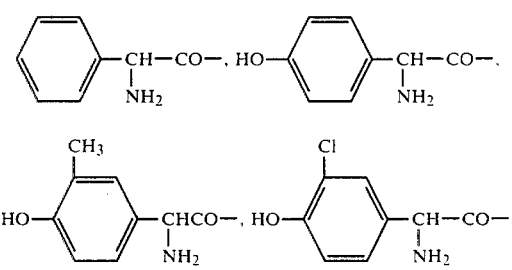

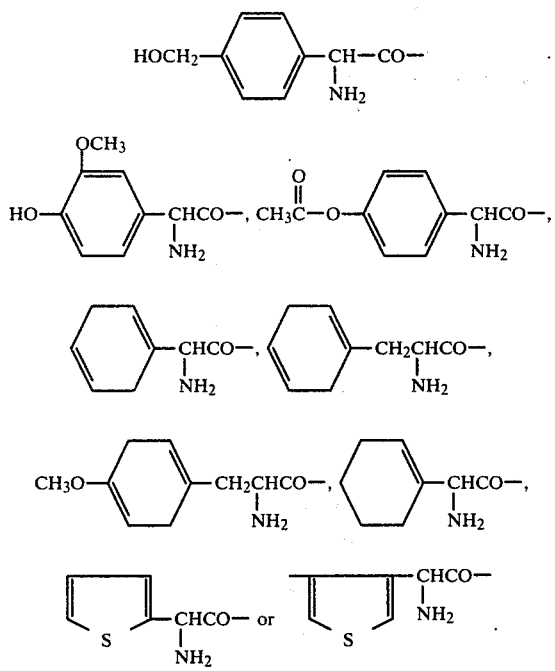

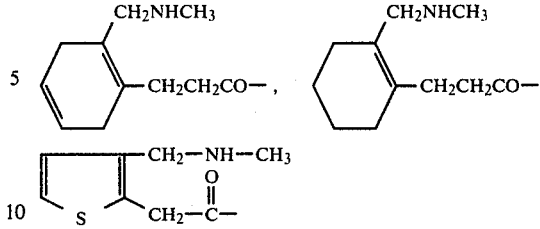

Another preferred embodiment of the present invention consists of the compounds of Formula I wherein $R^1$ has the structure

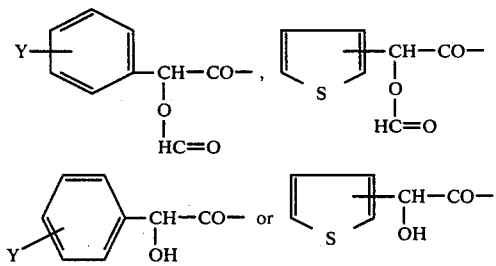

Another preferred embodiment of the present invention consists of the compounds of Formula I having the D configuration in the 7-side chain wherein $R^1$ has the structure

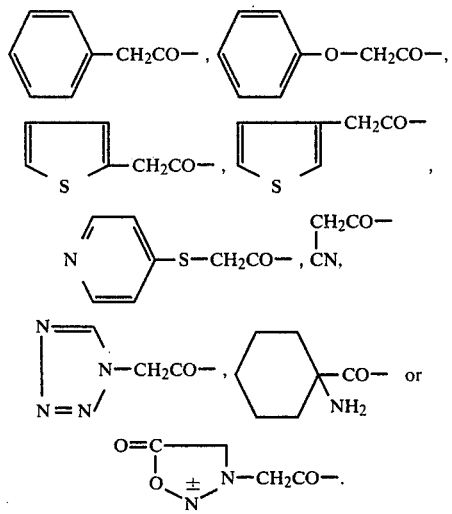

and Y is hydrogen, chlorine, bromine, fluorine, trifluoromethyl, amino, nitro, hydroxy, lower alkyl of 1–4 carbon atoms or lower alkoxy of 1–4 carbon atoms.

Another preferred embodiment of the present invention consists of the compounds of Formula I wherein $R^1$ has the structure

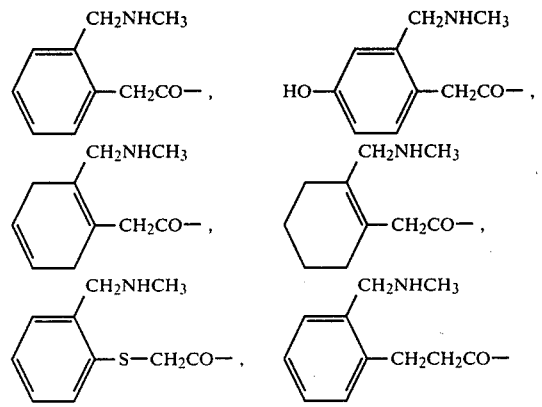

Another preferred embodiment of the present invention consists of the compounds of Formula I wherein $R^1$ has the structure

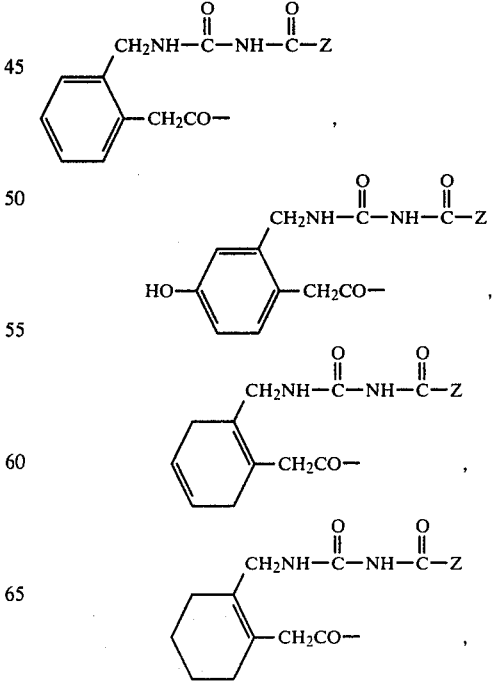

-continued

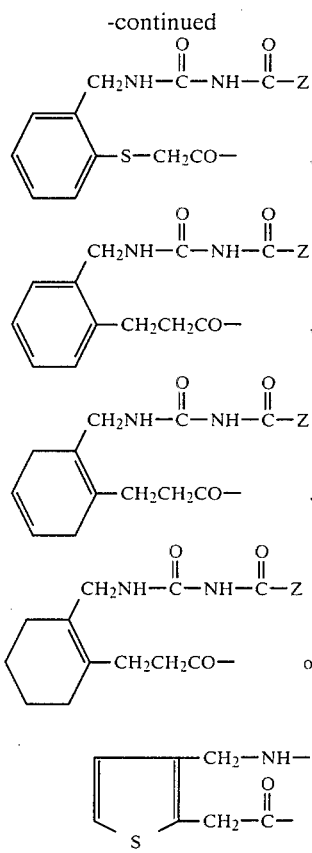

in which Z represents (lower)alkyl, cycloalkyl having 4, 5, 6 or 7 carbon atoms, monohalo(lower)alkyl, dichloromethyl, trichloromethyl, (lower)alkenyl of 2 to 6 carbon atoms,

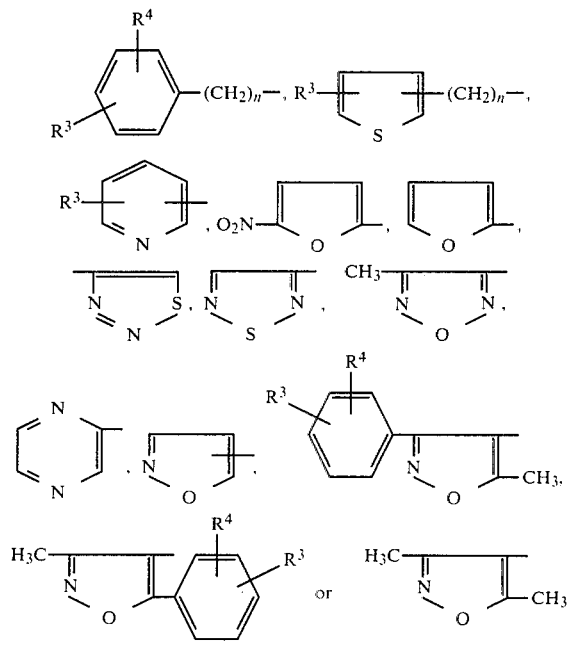

n is an integer from 0 to 3 inclusive and each of $R^3$ and $R^4$ is hydrogen, nitro, di(lower)alkylamino, (lower)alkanoylamino, (lower)alkanoyloxy, (lower)alkyl, (lower)alkoxy, sulfamyl, chloro, iodo, bromo, fluoro or trifluoromethyl. In the most preferred embodiments Z is phenyl, 2-thienyl, 3-thienyl, 2-furyl or 5-nitro-2-furyl.

Another preferred embodiment of the present invention consists of the compounds of Formula I having the D configuration in the 7-side chain wherein $R^1$ has the structure

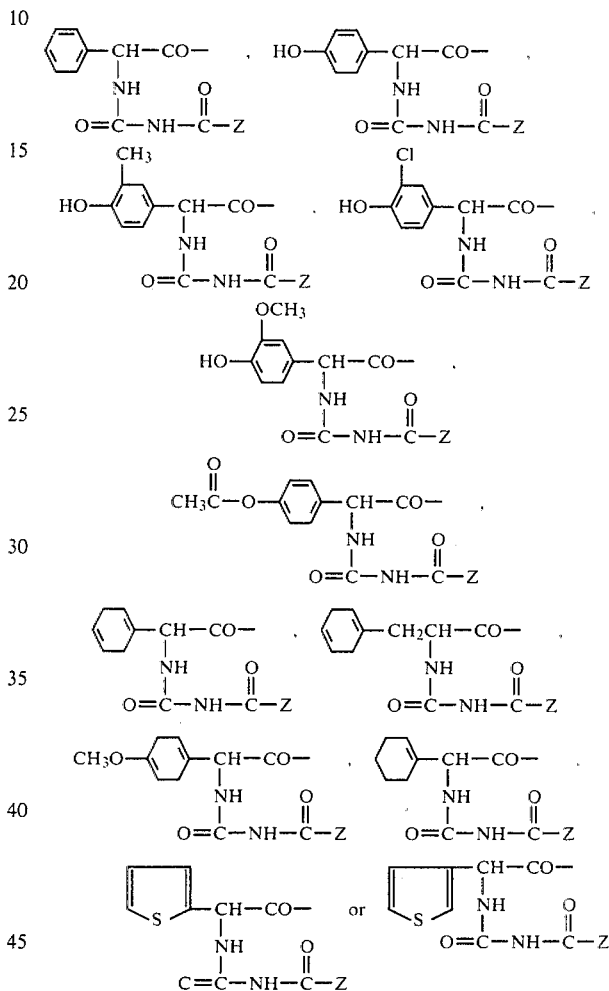

in which z represents (lower)alkyl, cycloalkyl having 4, 5, 6 or 7 carbon atoms, monohalo(lower)alkyl, dichloromethyl, trichloromethyl, (lower)alkenyl of 2 to 6 carbon atoms,

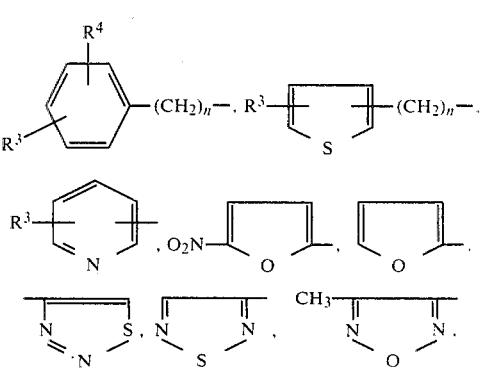

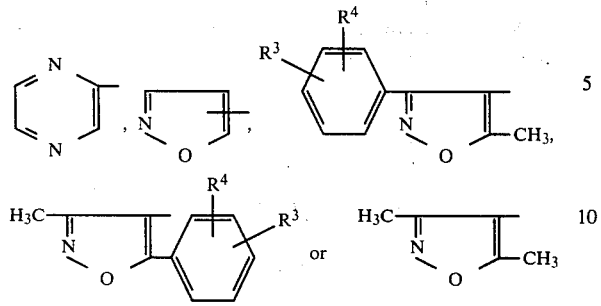

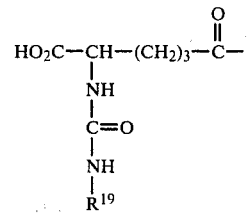

wherein $R^{19}$ is (lower)alkyl or a group of the formula

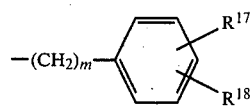

wherein m is an integer of 0 to 6 and $R^{17}$ and $R^{18}$ are alike or different and each is H, Cl, Br, F, $NO_2$, (lower)alkyl or (lower)alkoxy.

n is an integer from 0 to 3 inclusive and each of $R^3$ and $R^4$ is hydrogen, nitro, di(lower)alkylamino, (lower)alkanoylamino, (lower)alkanoyloxy, (lower)alkyl, (lower)alkoxy, sulfamyl, chloro, iodo, bromo, fluoro and trifluoromethyl. In the most preferred embodiments Z is phenyl, 2-thienyl, 3-thienyl, 2-furyl or 5-nitro-2-furyl.

Another preferred embodiment of the present invention consists of the compounds having the formula

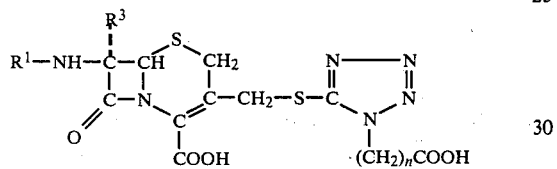

wherein $R^3$ is H or methoxy, n is an integer of 1 to 9, $R^1$ has the formula

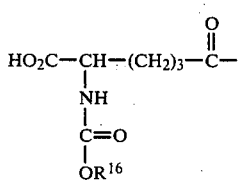

wherein $R^{16}$ is (lower)alkyl or an aralkyl group of the formula

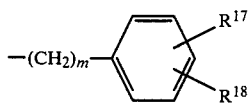

wherein m is an integer of 0 to 6 and $R^{17}$ and $R_{18}$ are alike or different and each is H, Cl, Br, F, $NO_2$, (lower)alkyl or (lower)alkoxy.

Another preferred embodiment of the present invention consists of the compounds having the formula

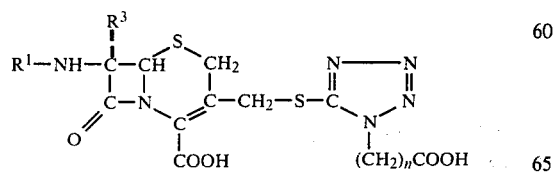

wherein $R^3$ is H or methoxy and n is an integer of 1 to 9, $R^1$ has the formula Another preferred embodiment of the present invention consists of the compounds of the formula

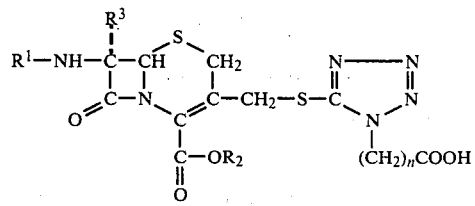

wherein $R^3$ is methoxy, n is an integer of 1 to 9 inclusive, $R^2$ is hydrogen, pivaloyloxymethyl, acetoxymethyl, methoxymethyl, acetonyl, phenacyl, p-nitrobenzyl or $\beta,\beta,\beta$-trichloroethyl and wherein $R^1$ has the structure

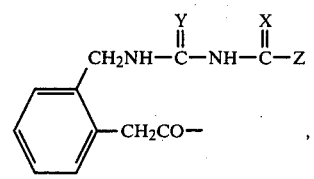

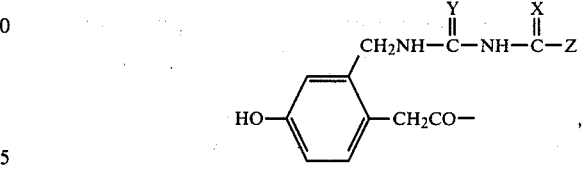

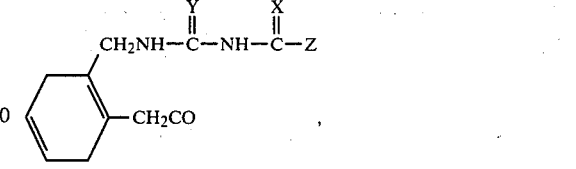

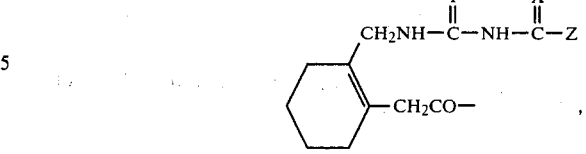

-continued

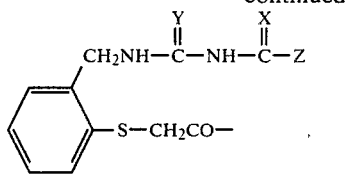

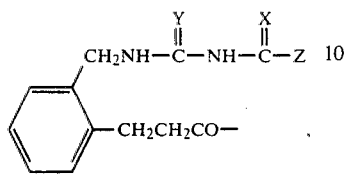

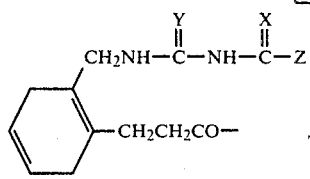

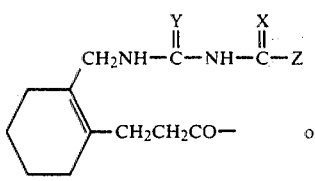

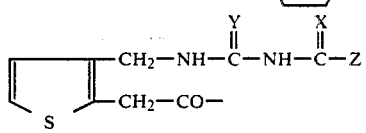

in which X represents oxygen or imino, Y represents oxygen or sulfur and Z represents amino, (lower)alkyl, cycloalkyl having 4, 5, 6 or 7 carbon atoms, monohalo(lower)alkyl, dichloromethyl, trichloromethyl, (lower)alkenyl of 2 to 6 carbon atoms,

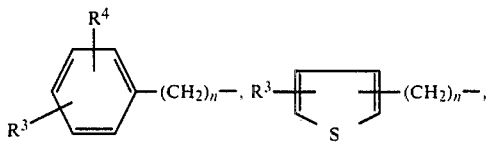

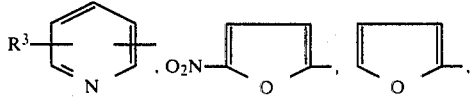

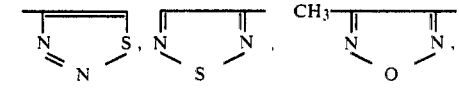

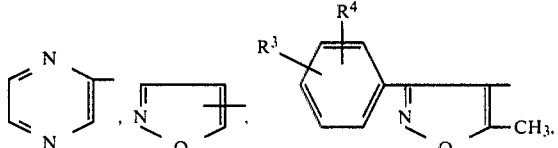

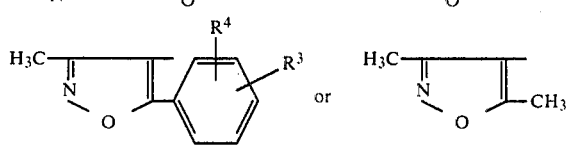 or n is an integer from 0 to 3 inclusive and each of $R^3$ and $R^4$ is hydrogen, nitro, di(lower)alkylamino, (lower)alkanoylamino, (lower)alkanoyloxy, (lower)alkyl, (lower)alkoxy, sulfamyl, chloro, iodo, bromo, fluoro or trifluoromethyl.

Another preferred embodiment of the present invention consists of the compounds of the formula

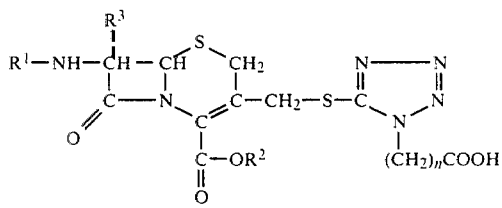

wherein $R^3$ is H or methoxy, n is an integer of 1 to 9 inclusive, $R^2$ is hydrogen, pivaloyloxymethyl, acetoxymethyl, methoxymethyl, acetonyl, phenacyl, p-nitrobenzyl or $\beta,\beta,\beta$-trichloroethyl and having the D configuration in the 7-side chain wherein $R^1$ has the structure

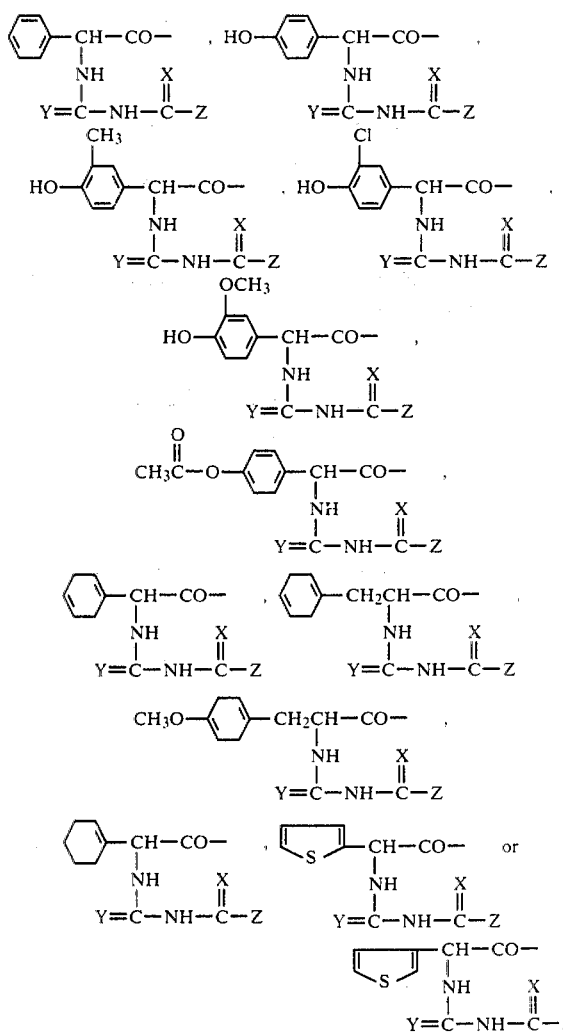

in which X represents oxygen or imino, Y represents oxygen or sulfur and Z represents amino, (lower)alkyl, cycloalkyl having 4, 5, 6 or 7 carbon atoms, monohalo(lower)alkyl, dichloromethyl, trichloromethyl, (lower)alkenyl of 2 to 6 carbon atoms,

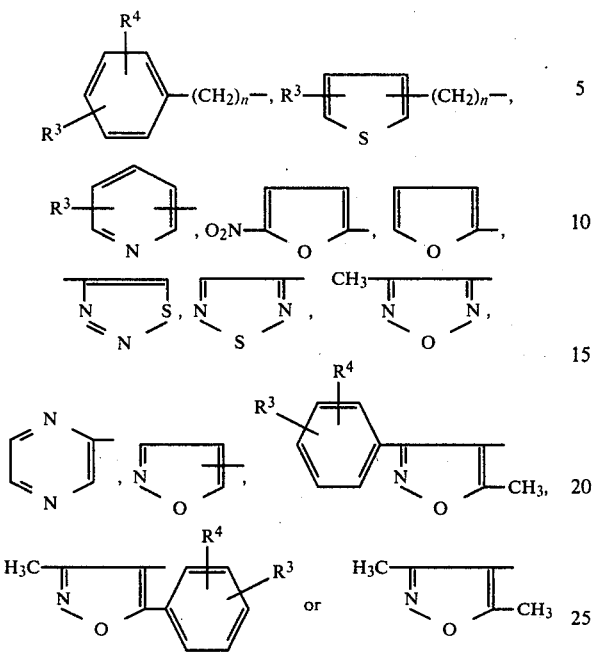

n is an integer from 0 to 3 inclusive and each of R³ and R⁴ is hydrogen, nitro, di(lower)alkylamino, (lower)alkanoylamino, (lower)alkanoyloxy, (lower)alkyl, (lower)alkoxy, sulfamyl, chloro, iodo, bromo, fluoro or trifluoromethyl.

Another preferred embodiment of the present invention consists of the compounds having the formula

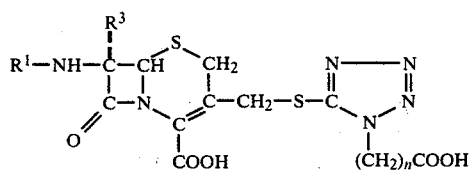

wherein R³ is H or methoxy, n is an integer of 1 to 9 inclusive, R¹ has the D configuration at the alpha carbon atom and has the formula

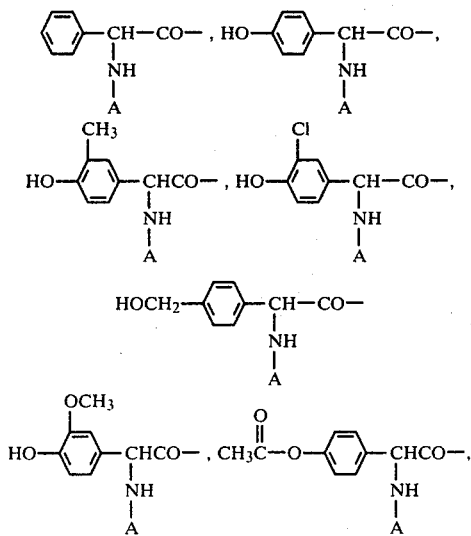

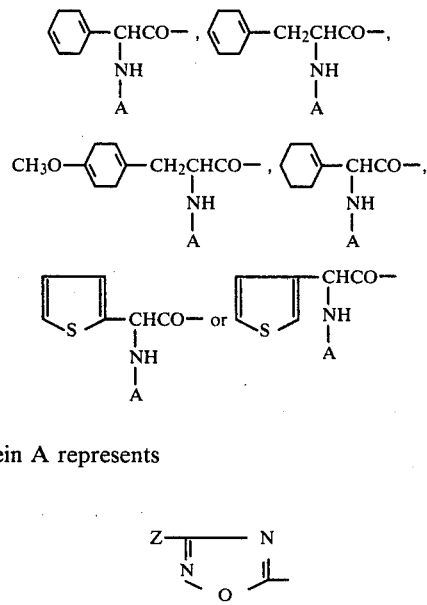

wherein A represents

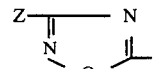

in which Z represents (lower)alkyl, cycloalkyl having four, five, six or seven carbon atoms, monohalo(lower)alkyl, dichloromethyl, trichloromethyl, (lower)alkenyl of two to six carbon atoms,

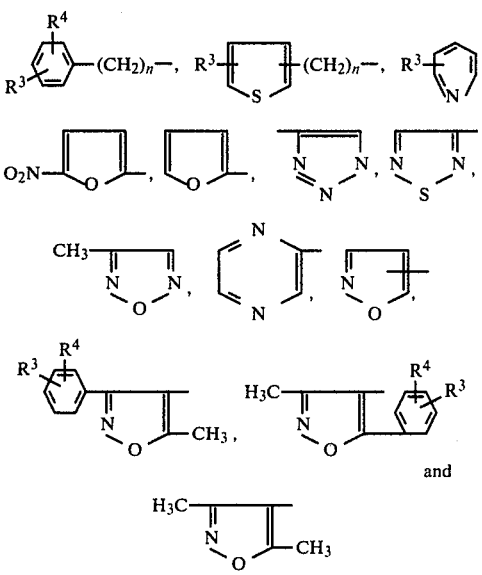

n is an integer from 0 to 3 inclusive and each of R³ and R⁴ is hydrogen, nitro, di(lower)alkylamine, (lower)alkanoylamino, (lower)alkanoyloxy, (lower)-alkyl (comprising straight and branched chain saturated aliphatic groups having from one to six carbon atoms inclusive), (lower)-alkoxy, sulfamyl, chloro, iodo, bromo, fluoro or trifluoromethyl.

Another preferred embodiment of the present invention consists of the compounds having the formula

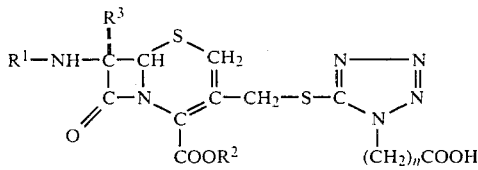

wherein R³ is H or methoxy, n is an integer of 1 to 9 inclusive, R² represents hydrogen, pivaloyloxymethyl, acetoxymethyl, methoxymethyl, acetonyl, phenacyl, p-nitrobenzyl or β,β,β-trichloroethyl and R¹ represents phenylacetyl,
o-, m- and p-fluorophenylacetyl,
o-, m- and p-nitrophenylacetyl,
o-, m- and p-guanidino-phenylacetyl,
o-, m- and p-acetoxyphenylacetyl,
o-, m- and p-methoxyphenylacetyl,
o-, m- and p-methylphenylacetyl,
o-, m- and p-hydroxyphenylacetyl,
N,N'bis-(2-chloroethyl)aminophenylpropionyl,
thien-2-acetyl,
thien-3-acetyl,
4-isoxazolylacetyl,
1-cyclohexenylacetyl,
1,4-cyclohexadienylacetyl,
pyridylacetyl,
sydnoneacetyl,
3-o-chlorophenyl-5-methyl-isoxazol-4-yl-acetyl,
cyanoacetyl,
3,5,7-triaza-1-azonia-1-adamantyl)acetyl,
m-aminopyridiniumacetyl,
o-, m- and p-(2'-aminoethoxy)phenylacetyl,
4,5-dimethoxycarbonyl-1,2,3-triazol-1-ylacetyl,
4-cyano-1,2,3-triazol-1-ylacetyl,
imidazol-(1)-acetyl,
m- and p-aminomethylphenylacetyl,
α-amino-2,4,6-cycloheptatrienyl-acetyl,
lower alkoxycarbonylacetyl,
cyanoacetyl,
hexanoyl,
heptanoyl,
octanoyl,
butylthioacetyl,
trifluoromethylthioacetyl,
allylthioacetyl,
phenoxyacetyl,
2-phenoxy-2-phenylacetyl,
2-phenoxypropionyl,
2-phenoxybutyryl,
benzyloxycarbonyl,
2-methyl-2-phenoxypropionyl,
p-cresoxyacetyl,
p-methylthiophenoxyacetyl,
S-phenylthioacetyl,
S-chlorophenylthioacetyl,
S-fluorophenylthioacetyl,
pyridylthioacetyl,
S-benzylthioacetyl,
p-aminomethylphenylthioacetyl,
cyanomethylthioacetyl,
4-pyridylthioacetyl,
S-benzylthiopropionyl,
benzoyl,
aminobenzoyl,
4-isoxazolyl-carbonyl,
cyclopentane-carbonyl,
sydnone-carbonyl,
naphthoyl,
2-ethoxynapthoyl,
quinoxalinyl-carbonyl,
3-carboxy-2-quinoxalinylcarbonyl,
2,6-dimethoxybenzoyl,
2-biphenylcarbonyl,
2-methylaminobenzoyl,
2-carboxybenzoyl,
3-phenyl-5-methylisoxazol-4-yl-carbonyl,
3-o-chlorophenyl-5-methyl-isoxazol-4-yl-carbonyl or
3-2',6'-dichlorophenyl-5-methylisoxazol-4-ylcarbonyl.

Another preferred embodiment of the present invention consists of the compounds having the formula

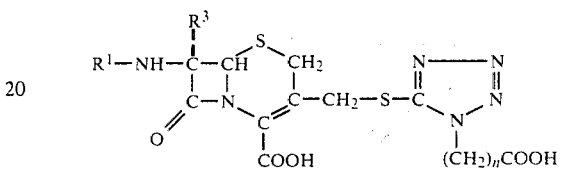

wherein R³ is H or methoxy, n is an integer of 1 to 9 inclusive, R¹ is

wherein Z is amino(lower)alkyl, N-(lower)alkylamino(lower)alkyl, or N,N-di(lower)alkylamino(lower)alkyl or R¹ is

wherein Z is aminophenyl, aminophenyl(lower)alkyl, N-(lower)alkylaminophenyl, N,N-di(lower)alkylaminophenyl, N-(lower)alkylaminophenyl(lower)alkyl, N,N-di(lower)alkylaminophenyl(lower)alkyl, phenylamino(lower)alkyl, phenyl(lower)alkylamino(lower)alkyl, substituted phenylamino(lower)alkyl or substituted phenyl(lower)alkylamino(lower)alkyl, wherein substituted phenyl is defined as a group having the formula

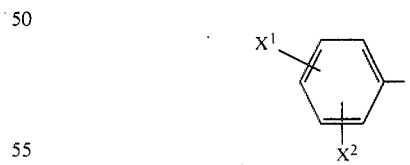

in which X¹ and X² are alike or different and are selected from the group consisting of hydrogen, fluoro, chloro, bromo, (lower)alkyl, (lower)alkoxy, nitro, amino, trifluoromethyl and phenyl or R¹ is

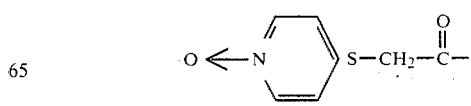

or R¹ is

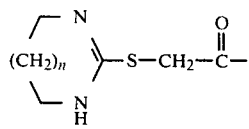

wherein n is 1 or 2 or $R^1$ is

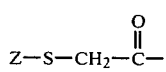

wherein Z is a radical of the formula

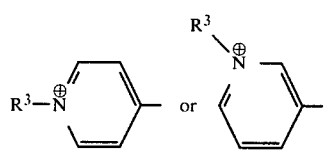

in which $R^3$ is (lower)alkyl, (lower)alkenyl or (lower)alkynyl or $R^1$ is

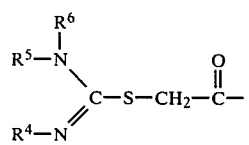

wherein formula $R^4$, $R^5$ and $R^6$ are each (lower)alkyl, (lower)alkynyl, (lower)alkenyl or (lower)cycloalkyl and $R^5$ may also be hydrogen; or $R^1$ is

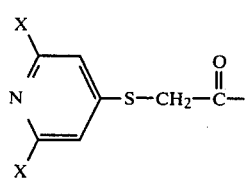

in which X is fluoro or chloro or $R^1$ is

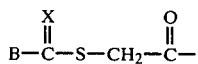

wherein X is oxygen or sulfur; B represents di(lower)alkylamino wherein the alkyl group may be alike or different, piperidino, methylpiperidino, dimethylpiperidino, pyrrolidino, methylpyrrolidino, dimethylpyrrolidino, morpholino, methylmorpholino, dimethylmorpholino, N'-(lower)alkylpiperazino, N'-(lower)alkyl-methylpiperazino, N'-(lower)alkyl-dimethylpiperazino, trimethyleneimino, hexamethyleneimino or a radical of the formula

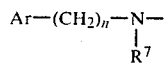

wherein n is zero, one, two or three, $R^7$ is (lower)alkyl and Ar is a radical of the formula

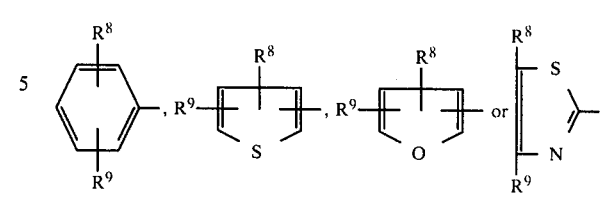

wherein $R^8$ and $R^9$ are each hydrogen, fluoro, chloro, bromo, (lower)alkyl or (lower)alkoxy.

Another preferred embodiment of the present invention consists of the compounds having the formula

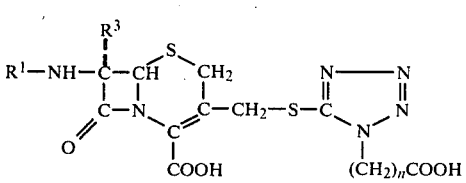

wherein $R^3$ is H or methoxy, n is an integer of 1 to 9 inclusive, $R^1$ has the formula

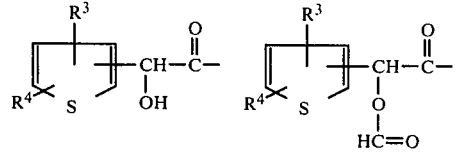

wherein $R^3$ and $R^4$ are each hydrogen, chloro, bromo, fluoro, iodo, nitro, (lower)alkyl, (lower)alkoxy, (lower)alkylthio, di(lower)alkylamino, (lower)alkanoylamino, (lower)alkanoyl or (lower)alkylsulfonyl.

Another preferred embodiment of the present invention consists of the compounds having the formula

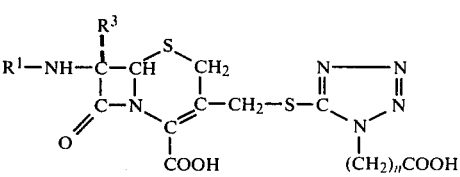

wherein $R^3$ is H or methoxy, n is an integer of 1 to 9 inclusive, $R^1$ has the formula

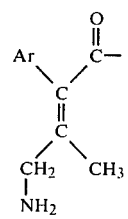

wherein Ar is

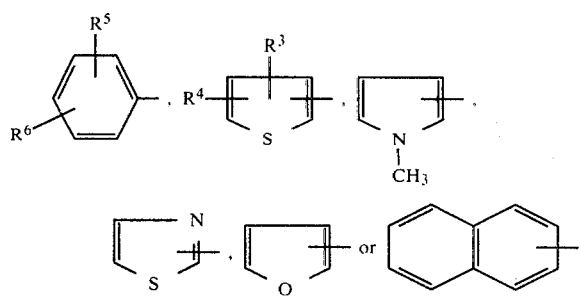

in which $R^5$ and $R^6$ are each hydrogen, fluoro, chloro, methoxy or methyl and $R^3$ and $R^4$ are each hydrogen, bromo or chloro.

Another preferred embodiment of the present invention consists of the compounds having the formula

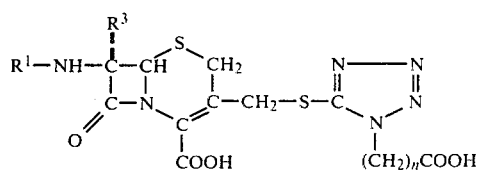

wherein $R^3$ is H or methoxy, n is an integer of 1 to 9 inclusive, $R^1$ is

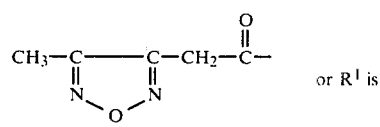

or $R^1$ is

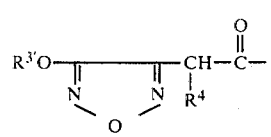

wherein $R^{3'}$ and $R^4$ are each a member selected from the group consisting of hydrogen and (lower)alkyl or $R^1$ is

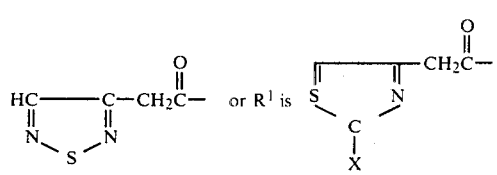

wherein X represents a member selected from the group consisting of hydrogen and (lower)alkyl or $R^1$ is

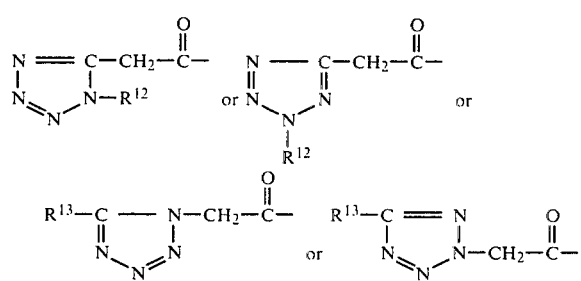

wherein $R^{12}$ is hydrogen or (lower)alkyl; $R^{13}$ is hydrogen, chloro, bromo, iodo, fluoro, trifluoromethyl, (lower)alkyl, (lower)alkoxy, (lower)alkylthio, carboxymethoxy, (lower)alkylsulfonyl, phenyl, benzyl, phenoxy, benzyloxy, and radicals of the formula

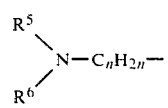

wherein $R^5$ and $R^6$ each represent hydrogen, (lower)alkyl, phenyl, benzyl, cycloalkyl having from three to seven carbon atoms, inclusive, and when taken together with >N-, constitute a heterocyclic ring selected from the group consisting of pyrrolidino, piperidino, morpholino, 1,2,5,6-tetrahydropyridino, N-(lower)alkylpiperazino and hexamethyleneimino and n is an integer from 0 to 3 inclusive; or $R^1$ is

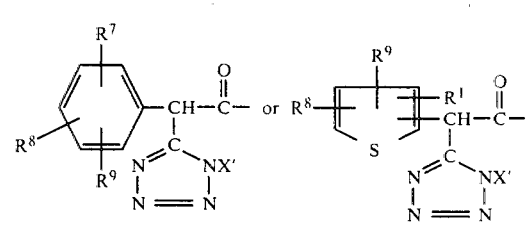

wherein $R^7$, $R^8$ and $R^9$ each represents a member selected from the group consisting of hydrogen, nitro, di(lower)alkylamino, (lower)alkanoylamino, (lower)alkanoyloxy, (lower)alkyl, (lower)alkoxy, sulfamyl, chloro, iodo, bromo, fluoro and trifluoromethyl; X and X' are a like or different and each represents hydrogen or $R^1$ is

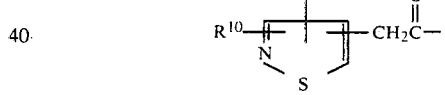

wherein $R^{10}$ and $R^{11}$ each represent a member selected from the group consisting of hydrogen, chloro, bromo, iodo and methyl.

Another preferred embodiment of the present invention consists of the compounds having the formula

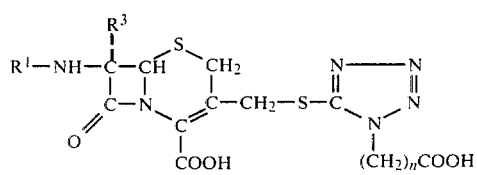

wherein $R^3$ is H or methoxy, n is an integer of 1 to 9 inclusive, $R^1$ is

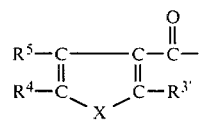

wherein X is a divalent radical selected from the group consisting of

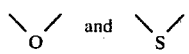 and 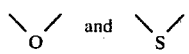

wherein R³' and R⁴ each represent a member selected from the group consisting of (lower)alkyl, chloro, bromo and the radical having the formula

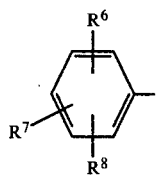

wherein R⁶, R⁷ and R⁸ each represent a member selected from the group consisting of hydrogen, fluoro, bromo and chloro, and R⁵ represents a member selected from the group consisting of hydrogen, (lower)alkyl and the radical having the formula

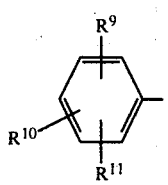

wherein R⁹, R¹⁰ and R¹¹ each represent a member selected from the group consisting of hydrogen, fluoro, bromo and chloro and, when bonded together as a benz group, R⁴ and R⁵ each represent vinyl or R¹ is

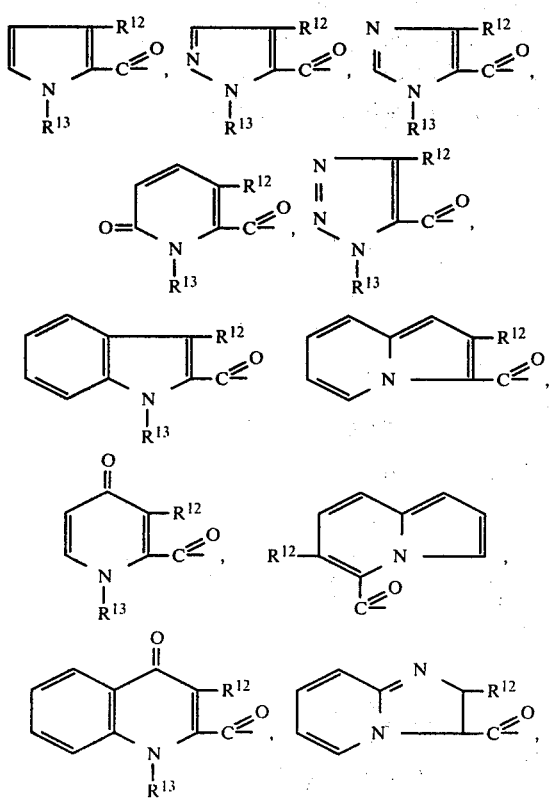

-continued

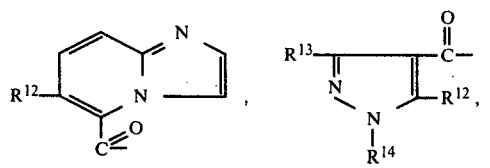

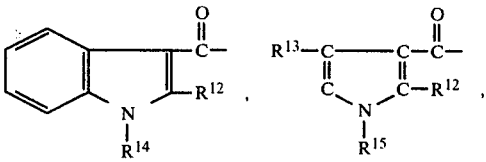

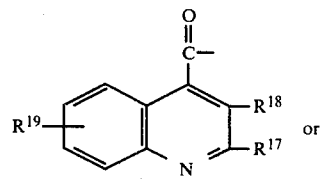 or

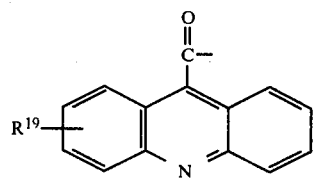

wherein R¹² and R¹³ each represent a member selected from the group consisting of nitro, (lower)alkyl, (lower)alkoxy, (lower)alkanoylamino, chloro, bromo, iodo, fluoro, hydroxy, (lower)alkylthio, cyclohexyl, cyclopentyl, cycloheptyl, (lower)alkoxycarbonyl, mercapto, (lower)alkylsulfonyl, (lower)alkanoyl, (lower)alkanoyloxy and the three radicals having the formulae

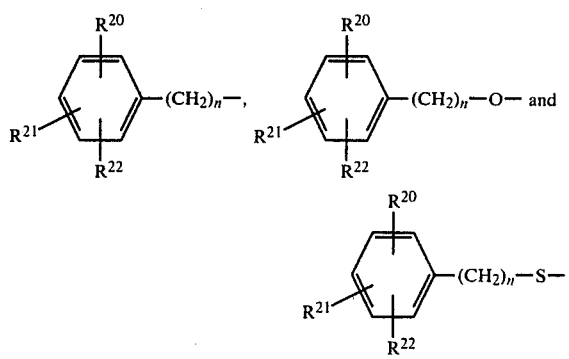

wherein n is an integer from zero to three inclusive and R²⁰, R²¹ and R²² each represent a member selected from the group consisting of hydrogen, fluoro, bromo, chloro, iodo, trifluoromethyl, (lower)alkyl, (lower)alkoxy, hydroxy, nitro and amino; R¹⁴ represents a member selected from the group consisting of hydrogen, (lower)alkyl and the radical having the formula

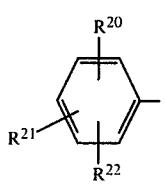

wherein $R^{20}$, $R^{21}$ and $R^{22}$ have the meaning defined above; $R^{15}$ represents a member selected from the group consisting of hydrogen and (lower)alkyl; $R^{16}$ represents a member selected from the group consisting of hydrogen and $R^{12}$ as defined above; $R^{17}$ and $R^{18}$ each represent a member selected from the group consisting of (lower)alkyl, (lower)alkoxy, chloro, bromo, iodo, fluoro, cyclohexyl, cyclopentyl, cycloheptyl and the two radicals having the formulae

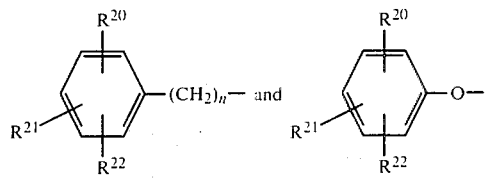

wherein n is an integer from zero to three inclusive and $R^{20}$, $R^{21}$ and $R^{22}$ have the meaning defined above; and $R^{19}$ represents a member selected from the group consisting of hydrogen and $R^{17}$ as defined above; or $R^1$ is

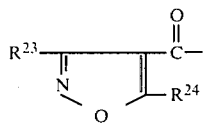

wherein $R^{23}$ and $R^{24}$ each represent a member selected from the group consisting of (lower)alkyl, (lower)alkylthio, benzylthio, cyclohexyl, cyclopentyl, cycloheptyl, benzyl, styryl, phenylethyl, phenylpropyl, furyl, thienyl, naphthyl and a member selected from the group consisting of a radical having the formula

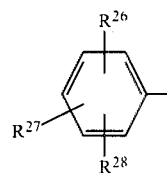

wherein $R^{26}$, $R^{27}$ and $R^{28}$ each represent a member selected from the group consisting of hydrogen, fluoro, chloro, bromo, iodo, trifluoromethyl, (lower)alkyl, (lower)alkoxy, nitro, methylsulfonyl, cyano, di(lower)alkylamino and methylmercapto; or $R^1$ is

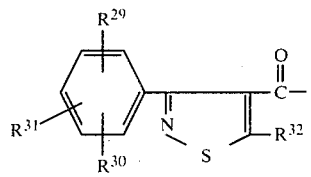

wherein $R^{29}$, $R^{30}$ and $R^{31}$ represent hydrogen, chloro, bromo, iodo, trifluoromethyl, fluoro, methylsulfonyl, nitro, (lower)alkyl or (lower)alkoxy, and $R^{32}$ represents (lower)alkyl or $R^1$ is

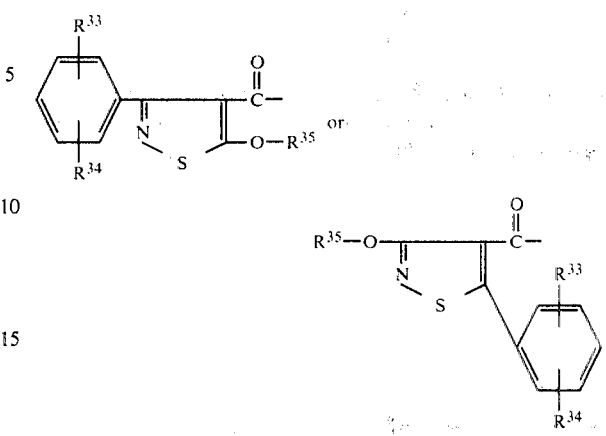

wherein $R^{33}$ and $R^{34}$ are each hydrogen, chloro, bromo, iodo, (lower)alkyl, (lower)alkoxy or trifluoromethyl and $R^{35}$ represents (lower)alkyl.

Another preferred embodiment of the present invention consists of the compounds of the formula

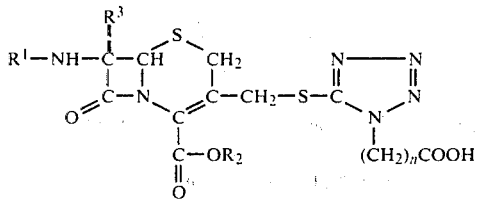

wherein $R^3$ is H or methoxy, n is an integer of 1 to 9 inclusive, $R^2$ is hydrogen, pivaloyloxymethyl, acetoxymethyl, methoxymethyl, acetonyl, phenacyl, p-nitrobenzyl or $\beta,\beta,\beta$-trichloroethyl and $R^1$ has the structure

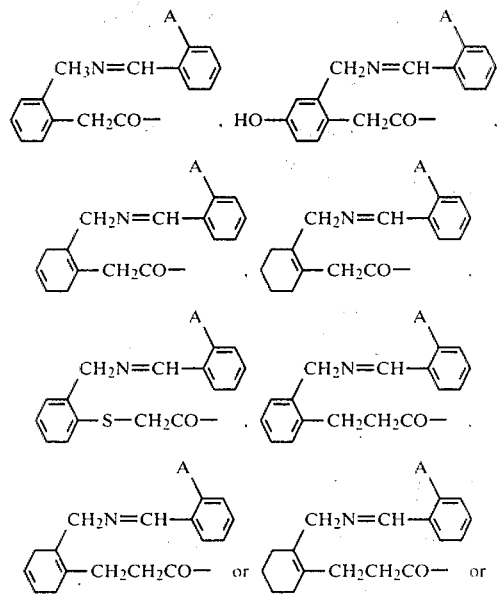

-continued

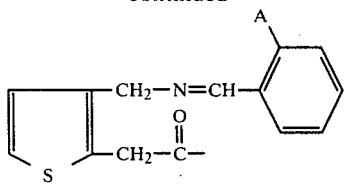

wherein A is —H or —OH.

Another preferred embodiment of the present invention consists of the compounds of the formula

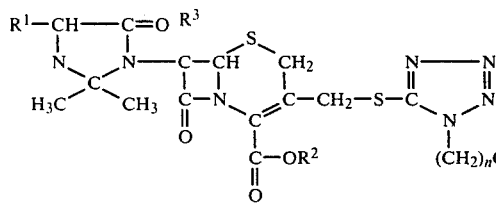

wherein $R^3$ is H or methoxy, n is an integer of 1 to 9 inclusive, $R^2$ is hydrogen, pivaloyloxymethyl, acetoxymethyl, methoxymethyl, acetonyl, phenacyl, p-nitrobenzyl or $\beta,\beta,\beta$-trichloroethyl and having the D configuration in the 7-side chain wherein $R^1$ has the structure

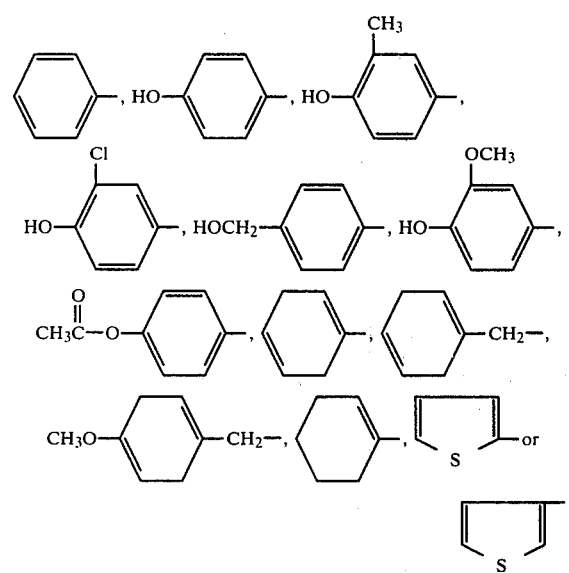

Another preferred embodiment of the present invention consists of the compounds of the formula

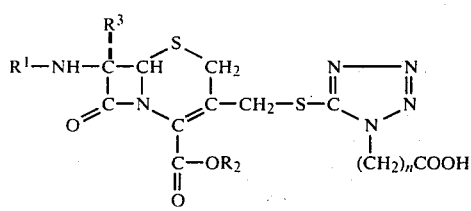

wherein $R^3$ is H or methoxy, n is an integer of 1 to 9 inclusive, $R^2$ is hydrogen, pivaloyloxymethyl, acetoxymethyl, methoxymethyl, acetonyl, phenacyl, p-nitrobenzyl or $\beta,\beta,\beta$-trichloroethyl and having the D configuration in the 7-side chain wherein $R^1$ has the structure

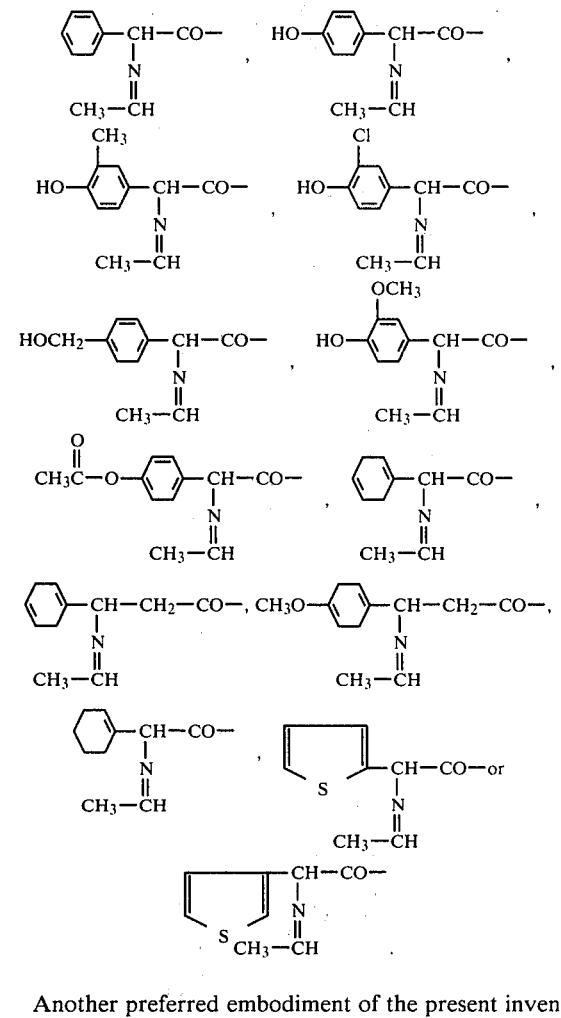

Another preferred embodiment of the present invention consists of the compounds of the formula

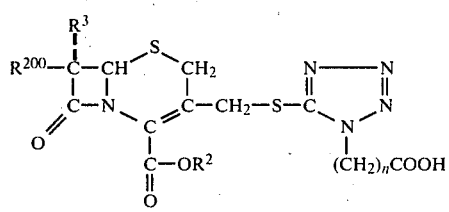

wherein $R^3$ is H or methoxy, n is an integer of 1 to 9 inclusive, $R^2$ is hydrogen, pivaloyloxymethyl, acetoxymethyl, methoxymethyl, acetonyl, phenacyl, p-nitrobenzyl or $\beta,\beta,\beta$-trichloroethyl and having the D configuration in the 7-side chain wherein $R^{200}$ has the structure

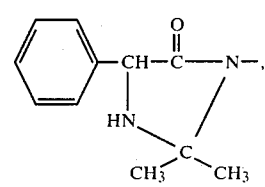

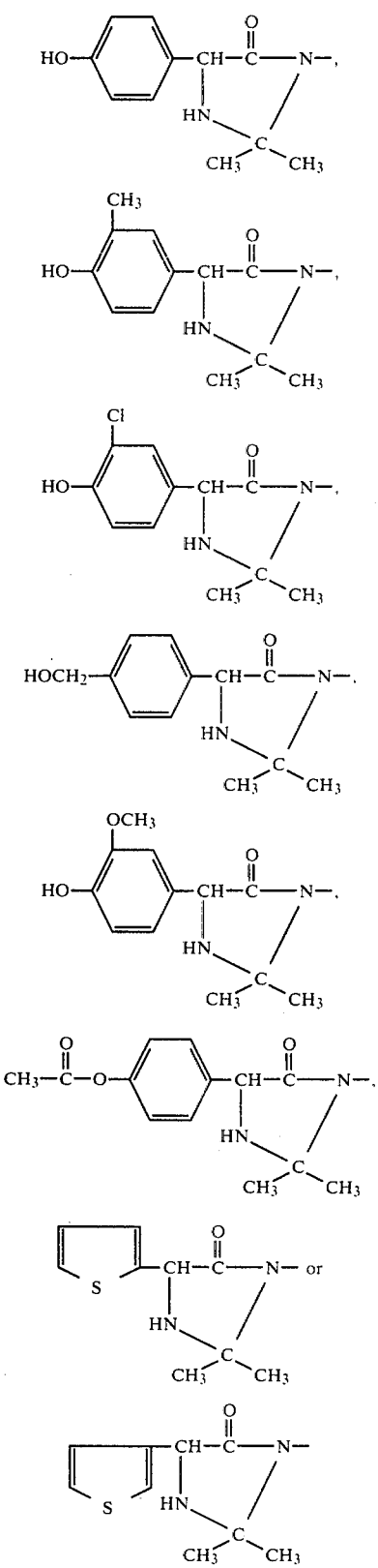

Another preferred embodiment of the present invention consists of the compounds having the formula

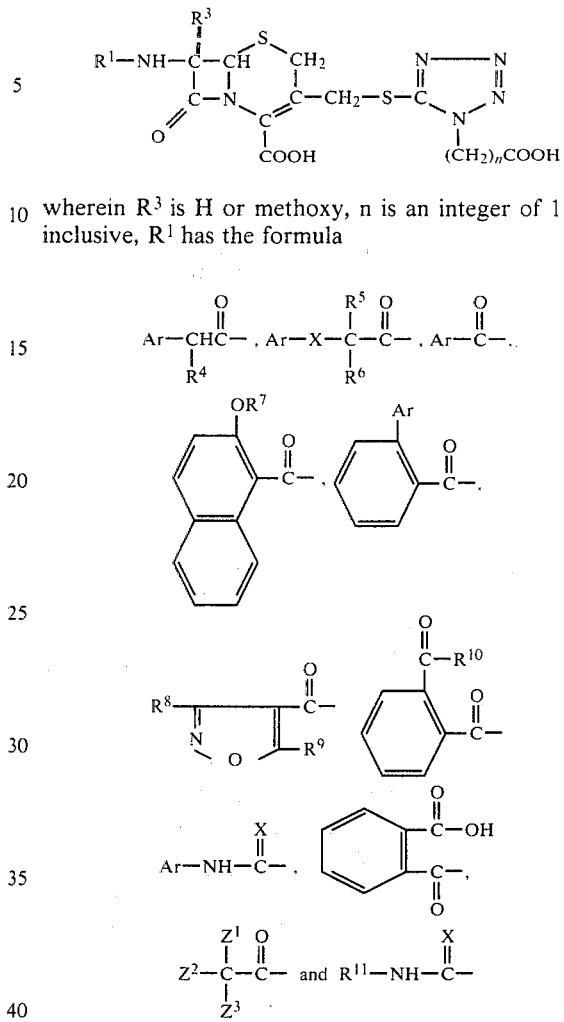

wherein $R^3$ is H or methoxy, n is an integer of 1 to 9 inclusive, $R^1$ has the formula wherein $R^4$ represents a member selected from the group consisting of hydrogen, amino, carbobenzoxyamino, phenyl, fluoro, chloro, bromo, iodo, hydroxy, (lower)alkanoyloxy and (lower)alkoxy; X represents a member selected from the group consisting of oxygen and sulfur; $R^5$ and $R^6$ each represent a member selected from the group consisting of hydrogen, phenyl, benzyl, phenethyl and (lower)alkyl; $R^7$ represents (lower)alkyl; $R^8$ and $R^9$ each represent a member selected from the group consisting of (lower)alkyl, (lower)alkylthio, benzylthio, cyclohexyl, cyclopentyl, cycloheptyl, benzyl, phenethyl, phenylpropyl, furyl, thienyl, naphthyl and Ar—; $R^{10}$ represents a member selected from the group consisting of (lower)alkylamino, di(lower)alkylamino, cycloalkylamino having from 3 to 7 carbon atoms inclusive, allylamino, diallylamino, phenyl(lower)alkylamino, morpholino, (lower)alkylamino, pyrrolidino, (lower)alkylpyrrolidino, di(lower)alkylpyrrolidino, N,N-hexamethyleneimino, piperidino, (lower)alkylpiperidino, di(lower)alkylpiperidino, 1,2,5,6-tetrahydropyridino, N-(lower)alkylpiperazino, N-(lower)alkylpiperazino, N-phenylpiperazino, N-(lower)alkyl(lower)alkylpiperazino, N-(lower)alkyl-di-(lower alkylpiperazino, furfurylamino, tetrahydrofurfurylamino, N-(lower)alkyl-N-furfurylamino, N-alkyl-N-anilino and (lower)alkoxyanilino; $Z^1$, $Z^2$ and $Z^3$ each represent a member selected from the group consisting of (lower- )alkyl, and Ar—; $R^{11}$ represents a member selected from the group consisting of (lower)alkyl, (lower)cycloalkyl, naphthyl, benzyl, phenethyl and

and Ar represent a monovalent radical having one of the formulae

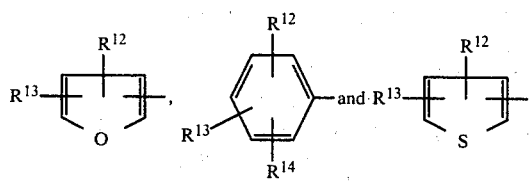

wherein $R^{12}$, $R^{13}$ and $R^{14}$ are each a member selected from the group consisting of hydrogen, chloro, bromo, iodo, trifluoromethyl, phenyl, (lower)alkyl and (lower)alkoxy, but only one R group may represent phenyl.

The present invention also provides the process for the production of the antibacterial agents having the structure

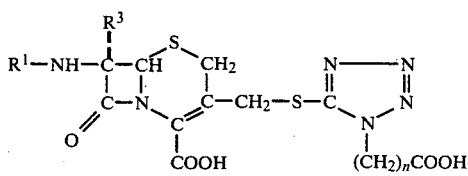

wherein $R^3$ is H or methoxy, n is an integer of 1 to 9 inclusive, $R^1$ is acyl which comprises reacting a compound of the formula

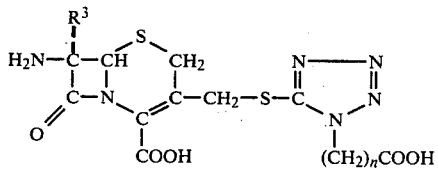

in which $R^3$ and n are as above, or a salt or easily hydrolyzed ester or Schiff base as with benzaldehyde or salicylaldehyde thereof (including, but not limited to, those of U.S. Pat. No. 3,284,451 and U.K. No. 1,229,453 and any of the silyl esters described in U.S. Pat. No. 3,249,622 for use with 7-aminopenicillanic acid and used in Great Britain No. 1,073,530 and particularly the pivaloyloxymethyl, acetoxymethyl, methoxymethyl, acetonyl, phenacyl, p-nitrobenzyl, β,β,β-trichloroethyl, 3-phthalidyl and 5-indanyl esters) thereof with an organic monocarboxylic acid chloride or a functional equivalent thereof as an acylating agent.

Such functional equivalents include the corresponding acid anhydrides, including mixed anhydrides and particularly the mixed anhydrides prepared from stronger acids such as the lower aliphatic monoesters or carbonic acid, or alkyl and aryl sulfonic acids and of more hindered acids such as diphenylacetic acid. A particularly useful anhydride is an N-carboxy-anhydride (also called a Leuch's anhydride; see U.S. Pat. Nos. 3,080,356 and 3,206,455) including but not limited to D-mandelic acid carboxyanhydride (U.S. Pat. No. 3,167,549) or the corresponding substituted D-mandelic acid carboxyanhydride. In addition, an acid azide or an active ester or thioester (e.g. with p-nitrophenyl, 2,4-dinitrophenol, thiophenol, thioacetic acid) may be used or the free acid itself may be coupled with compound II after first reacting said free acid with N,N'-dimethylchloroformiminium chloride [cf. Great Britain 1,008,170 and Novak and Weichet, Experientia XXI, 6, 360 (1965)] or by the use of enzymes or of an N,N'-carbonyldiimidazole or an N,N'-carbonylditriazole [cf. South African patent specification No. 63/2684] or a carbodiimide reagent [especially N,N'-dicyclohexylcarbodiimide, N,N'-diisopropylcarbodiimide or N-cyclohexyl-N'-(2-morpholinoethyl)carbodiimide; cf. Sheehan and Hess. J. Amer. Chem. Soc., 77, 1967 (1955)], or of alkylylamine reagent [cf. R. Buijle and H. G. Viehe, Angew. Chem. International Edition 3, 582, (1964)] or of an isoxasolium salt reagent [cf. R. B. Woodward, R. A. Olofson and H. Mayer, J. Amer. Chem. Soc., 83, 1010 (1961)], or of a ketenimine reagent [cf. C. L. Stevens and M. F. Munk, J. Amer. Chem. Soc., 80, 4065 (1958)] or of hexachlorocyclotriphosphatriazine or hexabromocyclotriphosphatriazine (U.S. Pat. No. 3,651,050) or of diphenylphosphoryl azide [DPPA; J. Amer. Chem. Soc., 94, 6203–6205 (1972)] or of diethylphosphoryl cyanide [DEPC; Tetrahedron Letters No. 18, pp. 1595–1598 (1973)] or of diphenyl phosphite [Tetrahedron Letters No. 49, pp. 5047–5050 (1972)]. Another equivalent of the acid chloride is a corresponding azolide, i.e., an amide of the corresponding acid whose amide nitrogen is a member of a quasiaromatic five membered ring containing at least two nitrogen atoms, i.e., imidazole, pyrazole, the triazoles, benzimidazole, benzotriazole and their substituted derivatives. As an example of the general method for the preparation of an azolide, N,N'-carbonyldiimidazole is reacted with a carboxylic acid in equimolar proportions at room temperature in tetrahydrofuran, chloroform, dimethylformamide or a similar inert solvent to form the carboxylic acid imidazolide in practically quantitative yield with liberation of carbon dioxide and one mole of imidazole. Dicarboxylic acids yield dimidazolide. The by-product, imidazole, precipitates and may be separated and the imidazolide isolated, but this is not essential. The methods for carrying out these reactions to produce a cephalosphorin and the methods used to isolate the cephalosporin so produced are well known in the art.

Mention was made above of the use of enzymes to couple the free acid with compound II. Included in the scope of such processes are the use of an ester, e.g. the methyl ester, of that free acid with enzymes provided by various microorganisms, e.g. those described by T. Takahashi et al., J. Amer. Chem. Soc., 94(11), 4035–4037 (1972) and by T. Nara et al., J. Antibiotics (Japan) 24(5), 321–323 (1971) and in U.S. Pat. No. 3,682,777.

For the coupling of the organic carboxylic acid, including but not limited to a substituted or unsubstituted D-mandelic acid (with or without a protecting group on the α-hydroxyl), as described above with compound II (or a salt or preferably an easily hydrolyzed ester or Schiff base, as with benzaldehyde, thereof) it is also convenient and efficient to utilize as the coupling agent phosphonitrilic chloride trimer (J. Org. Chem., 33(7), 2979–81, 1968) or N-ethoxy-1,2-dihydroquinoline (EEDQ) as described in J. Amer. Chem. Soc., 90, 823–824 and 1652–1653 (1968) and U.S. Pat. No.

3,455,929. The reaction is preferably carried out at 30°–35° C. in benzene, ethanol or tetrahydrofuran using about equimolar quantities of all three reagents followed by conventional isolation and removal by conventional methods of any blocking groups present.

An additional process of the present invention comprises the preparation of the compounds of the present invention by the displacement of the 3-acetoxy group of a 7-acylaminocephalosporanic acid (prepared by substituting 7-aminocephalosporanic acid for the 3-thiolated-7-aminocephalosporanic acids in the acylation procedures described herein and elsewhere reported) with a thiol having the formula

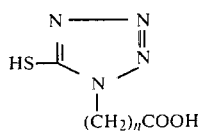

in which n is 1 to 9 and then removing the protecting group if any is present, as on an α-hydroxy or α-amino or the like or on the carboxyl group or both. The displacement of such a 3-acetoxy group with such a thiol may be accomplished in solution as in water or aqueous acetone at a temperature of at least room temperature and preferably within the range of about 50° to 100° C. in the presence of a mild base such as sodium bicarbonate, e.g. preferably near neutrality such as at about pH 6. An excess of the thiol is preferably employed. The reaction product is isolated by careful acidification of the reaction mixture followed by extraction with a water-immiscible organic solvent. To provide some specific examples for purposes of illustration but not of limitation, substituted or unsubstituted D-mandelamido-cephalosporanic acids are prepared by the procedures described generally or specifically in *J. Med. Chem.* 17(1), 34–41 (1974) and the references cited therein. As noted above, the preparation of many other 7-acylamidocephalosporanic acids is described in the patent and scientific literature, e.g. in U.S. Class 260-243C.

When the organic carboxylic acid contains a functional group such as amino or hydroxyl it is often desirable to first block (or protect) the amino or hydroxy group, then carry out the coupling reaction and finally subject the resulting compound to chemical removal of the protecting group, that is, subjecting the resulting compound to elimination reaction of the protecting group.

There are particularly included within the scope of the present invention the antibacterial agents which are prepared in the above-described acylation process by the use therein of the organic monocarboxylic acids or their acid chlorides or other equivalents which have previously been used to acylate 6-aminopenicillanic acid as described, for example U.S. Pat. Nos. 2,941,995; 2,951,839; 2,985,648; 2,996,501; 3,007,920; 3,025,290; 3,028,379; 3,035,047; 3,040,033; 3,041,332; 3,041,333; 3,043,831; 3,053,831; 3,071,575; 3,071,576; 3,079,305; 3,079,306; 3,080,356; 3,082,204; 3,093,547; 3,093,633; 3,116,285; 3,117,119; 3,118,877; 3,120,512; 3,120,513; 3,130,514; 3,127,394; 3,140,282; 3,040,032; 3,142,673; 3,147,247; 3,174,964; 3,180,863; 3,198,804; 3,202,653; 3,202,654; 3,202,655; 3,210,337; 3,157,639; 3,134,767; 3,132,136; in British Pat. Specifications Nos. 874,414; 874,416; 876,516; 876,662; 877,120; 877,323; 877,531; 878,233; 880,042; 880,400; 882,335; 888,100; 888,552; 889,066; 889,069; 889,070; 889,168; 889,231; 890,201; 891,174; 891,279; 891,586; 891,777; 891,938; 893,518; 894,247; 894,457; 894,460; 896,072; 899,199; 900,666; 902,703; 903,785; 904,576; 905,778; 906,383; 908,787; 914,419; 916,097; 916,204; 916,205; 916,488; 918,169; 920,176; 920,177; 920,300; 921,513; 922,278; 924,037; 925,281; 931,567; 932,644; 938,066; 938,321; 939,708; 940,488; 943,608; 944,417; in numerous Belgian Pat. Nos. e.g. 593,222; 595,171; 597,857; 602,494; 603,703; 609,039; 616,419; 617,187; and in South African Patent Applications, e.g. Nos. 60/2882; 60/3057; 60/3748; 61/1649; R61/2751; 62/54; 62/4920; 63/1612 and 63/2423.

The term "(lower)alkyl" as used herein means both straight and branched chain aliphatic hydrocarbon radicals having from one to ten carbon atoms such as methyl, ethyl, propyl, isopropol, butyl, isobutyl, t-butyl, amyl, hexyl, 2-ethylhexyl, heptyl, decyl, etc. Similarly, where the term "(lower)" is used as part of the description of another group, e.g. "(lower)alkoxy", it refers to the alkyl portion of such group which is therefore as described above in connection with "(lower)alkyl".

The present invention thus also provides the process for the production of the antibacterial agents having the structure

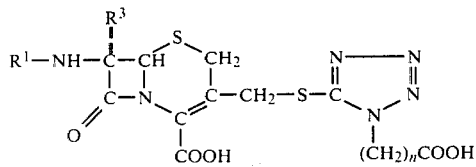

wherein $R^3$ is H or methoxy, n is an integer of 1 to 9 inclusive, $R^1$ is acyl which comprises reacting a compound having the formula

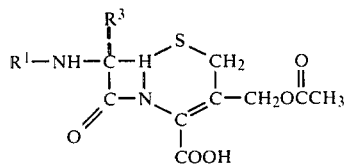

wherein $R^1$ is acyl and $R^3$ is H or methoxy (including cephalosporin C itself) with a compound having the formula

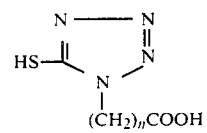

in which n is 1 to 9.

In the case of the compounds having a substituted amino group in the 7-side chain it is often desirable to prepare first the compound containing an unsubstituted (free or primary) amino group and then react that product with the appropriate reagent to produce final products of the type illustrated above in the definitions of acyl groups under viii, xvii and xviii as appropriate.

The present invention also provides the process for the production of the novel and valuable intermediate having the structure

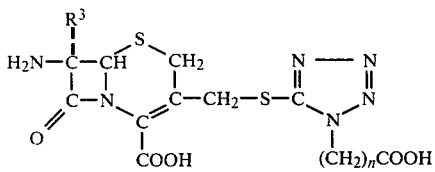

in which n is 1 to 9 and $R^3$ is H or methoxy, which comprises removing the 7-side chain from a reagent having the structure

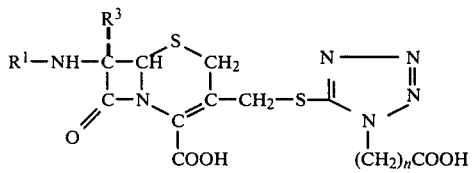

in which n is an integer of 1 to 9, wherein the acyl group ($R^1$) is one of those defined above in xiv, xv and xvi by converting said reagent, preferably in silylated form, to an imino-chloride (as with $PCl_5$) and thence to an imino-ether (as with methanol) and thence to the desired product by hydrolysis (as with water). Details for the conduct of such reactions are known to the art and taught, for example, in U.S. Pat. Nos. 3,575,970; 3,573,295 and 3,573,296.

The present invention also provides the process for the production of the novel and valuable intermediate having the structure

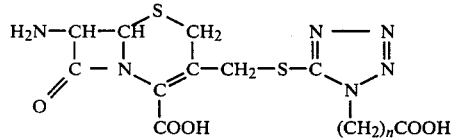

in which n is 1 to 9, which comprises reacting 7-aminocephalosporanic acid or a salt or easily hydrolyzed ester or Schiff base thereof with a compound having the formula

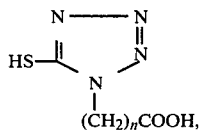

in which n is 1 to 9, also called $HSR^2$ herein.

Such salts include the nontoxic carboxylic acid salts thereof, including nontoxic metallic salts such as sodium, potassium, calcium and aluminum, the ammonium salt and substituted ammonium salts, e.g. salts of such nontoxic amines as trialkylamines including triethylamine, procaine, dibenzylamine, N-benzyl-beta-phenethylamine, 1-ephenamine, N,N'-dibenzylethylenediamine, dehydroabietylamine, N,N'-bis-dehydroabietylethylenediamine, N-(lower)alkylpiperidine, e.g. N-ethylpiperidine, and other amines which have been used to form salts with benzylpenicillin; and the nontoxic acid addition salts thereof (i.e., the amine salts) including the mineral acid addition salts such as the hydrochloride, hydrobromide, hydroiodide, sulfate, sulfamate and phosphate and the organic acid addition salts such as the maleate, acetate, citrate, oxalate, succinate, benzoate, tartrate, fumarate, malate, mandelate, ascorbate and the like.

Also included in this invention are the compounds (used as either intermediates or metabolic precursors) in which the amino group is "blocked" by substituents such as 2-iodoethoxycarbonyl (U.K. No. 1,349,673), t-butoxycarbonyl, carbobenzyloxy, formyl, o-nitrophenylsulfenyl, $\beta,\beta,\beta$-trichloroethoxycarbonyl, 4-oxo-2-pentenyl-2, 1-carbomethoxy-1-propenyl-2- and the like. Particularly included in such blocking groups are the ketones (especially acetone) and aldehydes (especially formaldehyde and acetaldehyde) disclosed, for example, in U.S. Pat. Nos. 3,198,804 and 3,347,851 and the $\beta$-ketoesters and $\beta$-diketones disclosed, for example, in U.S. Pat. No. 3,325,479 and the $\beta$-ketoamides disclosed in Japan No. 71/24714 (Farmdoc 47,321S).

The preferred esters of the cephalosporins of the present invention are the pivaloyloxymethyl, acetoxymethyl, methoxymethyl, acetonyl and phenacyl esters. All are useful intermediates in the production of the cephalosporin having a free carboxyl group and the first three are also of interest because on oral administration they provide different rates and amounts of absorption and give differing concentrations of the active antibacterial agent in blood and tissues.

As indicated above, these five esters of 7-aminocephalosporanic acid are each prepared by known methods. One excellent procedure is that of U.S. Pat. No. 3,284,451 in which sodium cephalothin is esterified by reaction with the corresponding active chloro or bromo compound (e.g. phenacyl bromide, chloroacetone, chloromethyl ether, pivaloyloxymethyl chloride [also called chloromethyl pivalate], acetoxymethyl chloride) and then the thienylacetic acid sidechain is removed enzymatically as in the same patent or chemically as in U.S. Pat. No. 3,575,970 and in Journal of Antibiotics, XXIV (11), 767–773 (1971). In another good method the triethylamine salt of 7-aminocephalosporanic acid is reacted directly with the active halogen compound, as in United Kingdom No. 1,229,453.

These esters of 7-aminocephalosporanic acid are then reacted with the nucleophile $HSR^2$ in the same manner as is illustrated herein for 7-aminocephalosporanic acid itself. The 3-thiolated ester of 7-aminocephalosporanic acid is then coupled with the organic carboxylic acid, e.g. D-(—)-2-phenylglycine, as before. Before or after removal of any blocking group, e.g. on an amino or hydroxy group in the 7-sidechain, the ester of the cephalosporin so obtained is, if not used per se, converted to its free acid, including its zwitterion (and, if desired, any salt) by removal of the esterifying group, as by aqueous or enzymatic hydrolysis (as with human or animal serum) or acidic or alkaline hydrolysis or by treatment with sodium thiophenoxide as taught in U.S. Pat. No. 3,284,451 and, in the penicillin series, by Sheehan et al., J. Org. Chem. 29(7), 2006–2008 (1964).

In another alternative synthesis, the 3-thiolated 7-aminocephalosporanic acid is prepared as described herein and then acylated at the 7-amino group and finally esterified, as by reaction of the appropriate alcohol with the acid chloride prepared, for example, by reaction of the final cephalosporin with thionyl chloride or by other essentially acidic esterification procedures.

The present invention also provides the process for the production of the novel and valuable intermediate having the structure

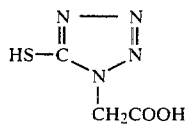

which comprises forming in an anhydrous solvent the lithio derivative of a thiol of the formula

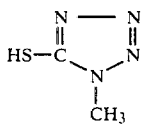

and reacting said lithio derivative with carbon dioxide to form a product which is then hydrolyzed to give the compound of the formula

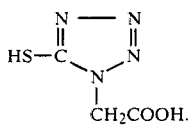

The present invention also provides the process for the production of the novel and valuable intermediate having the structure

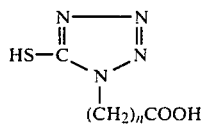

in which n is 1 to 9 which comprises (A) treating an isocyanate having the formula

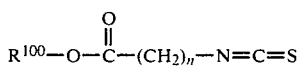

in which n is an integer of 1 to 9 inclusive, $R^{100}$ is (lower)alkyl of 1 to 6 carbon atoms and n is an integer of 1 to 9 inclusive or a radical having the formula

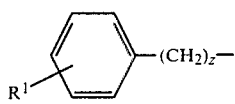

in which $R^1$ is H, Br, I, Cl, F, (lower)alkyl or alkoxy of 1 to 6 carbon atoms, $NO_2$, or the like and Z is 0 to 4, with sodium azide to produce the thiol-ester having the formula

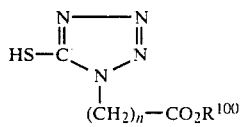

in which n and $R^{100}$ are as defined above; and (B) hydrolyzing the thiol-ester to produce the thiol-acid having the formula

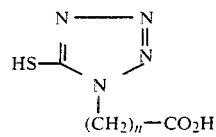

in which n is as above.

In the treatment of bacterial infections in man, the compounds of this invention are administered parenterally or orally in an amount of from about 5 to 200 mg./kg./day and preferably about 5 to 20 mg./kg./day in divided dosage, e.g. three to four times a day. They are administered in dosage units containing, for example, 125, 250 or 500 mg. of active ingredient with suitable physiologically acceptable carriers or excepients. The dosage units are in the form of liquid preparations such as solutions or suspensions.

STARTING MATERIALS

A. 1-Carboxymethyl-5-mercaptotetrazole

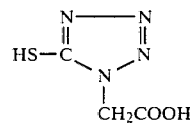

(a) Recrystallization of 1-methyl-5-mercaptotetrazole

Procedure:

1. One hundred and ten grams of 1-methyl-5-mercaptotetrazole is slurried in 350 ml. of boiling chloroform. A near solution is obtained.

2. The hot solution (50°–60°) is rapidly filtered by vacuum through a heated Buchner funnel (11 cm. SS No. 604 paper containing ¼ to ⅓ inch of packed filter aid ("Supercel"). The filter pad is washed with 50 ml. of 50°–60° C. chloroform which is added to the filtrate.

3. The filtrate is cooled to approximately 0°–6° C. and kept at 0°–6° C. for 2 hours. The crystals which have formed are collected by filtration at 0°–6° C. and washed with 60 ml. of 0°–6° C. chloroform which is added to the filtrate. The crystals (cut A) are air dried at 37°–45° C. for 18 hours.

4. The filtrate is concentrated on the rotary vacuum evaporator (60° C. bath) to approximately one-half volume. This slurry is cooled to 0°–6° C. and kept at 0°–6° C. for 2 hours. The crystals are collected by filtration at 0°–6° C., washed with 40 ml. of 0°–6° C. chloroform which is added to the filtrate. The crystals (cut B) are air dried at 37°–45° C. for 18 hours. Crystal cuts A and B are composited to give an approximate 65% weight yield.

5. The filtrate of cut B, Step 4 may be reworked twice as described in Step 4 to obtain an additional 15% recovery.

(b) Preparation of the Di-sodium Salt of 1-carboxymethyl-5-mercaptotetrazole

Procedure:

1. Five hundred ml. of substantially dry and pure tetrahydrofuran in a 2-liter 3 neck flask with stirrer is cooled in a salt-acetone-ice bath to approximately −10° C. Dry nitrogen gas is blown on the liquid surface.

2. Five hundred ml. of 15.06% (1.6 N) butyl lithium in hexane (Foote Mineral Co.) is added over a ten minute period under dry nitrogen and stirring to the tetrahydrofuran. The near solution is cooled to −5° to −10° C.

3. Forty six and four tenths gram (46.4 g.) of 1-methyl-5-mercaptotetrazole (recrystallized as above) is dissolved in 200 ml. of substantially pure and dry tetrahydrofuran. The solution is filtered if cloudy and then cooled to 5° to 10° C.

4. The cooled solution of step 3 is added over 10 minutes with stirring and under dry nitrogen to the butyl lithium solution. The temperature should be maintained at −5° C. to +10° C. maximum. Precipitates may form.

5. The mixture is stirred under dry nitrogen and 0° C. to +10° C. for one half hour.

6. Anhydrous carbon dioxide gas is bubbled through at a rapid rate and with rapid stirring for 15–30 minutes at approximately ambient temperature (0° to 10° C.) to no higher than +20° C.

7. The white precipitate which forms is suitably collected by filtration in an area of low humidity. The precipitate is washed with about 75 ml. of tetrahydrofuran.

8. The precipitate is dissolved in 250 ml. of water (pH 8.5–9.5). A second layer of tetrahydrofuran may be present. This may be removed in the vacuum rotary evaporator (50° C. bath).

9. The aqueous solution is adjusted to pH 1.6–2.0 with concentrated hydrochloric acid.

10. The acid aqueous solution is extracted twice with 250 ml. portions of ethyl acetate. Each 250 ml. ethyl acetate extract is back extracted with 100 ml. portions of water. The water extracts are discarded. The ethyl acetate extracts (free of any water layer) are filtered and composited.

11. The combined ethyl acetate extracts are concentrated to dryness on the vacuum rotary evaporator (60° C. bath).

12. The crystals in the flask are boiled with 300 ml. of chloroform for about 2 minutes. The hot slurry (50°–60° C.) is vacuum filtered through a heated Buchner funnel (11 cm-SS-604 paper). The crystals are washed with about 75 ml. of 50° C. chloroform. The crystals are air dried at room temperature for about 3 hours and then made about 100–200 mesh.

13. The 100–200 mesh crystals are treated with boiling chloroform exactly as described in step 12 (the hot chloroform removes most of the unreacted 1-methyl-5-mercaptotetrazole). Yield: approximately 45 to 50 grams of crystalline 1-carboxymethyl-5-mercaptotetrazole. These crystals may contain 0.02 to 0.05 moles of 1-methyl-5-mercaptotetrazole.

14. The crystals of step 13 are slurried with 250 ml. of ethyl ether at room temperature for 3–5 minutes. The mixture is filtered. The insolubles (0.5–5%) may be a contaminating symmetrical mercaptotetrazole ketone of the following tentative structure:

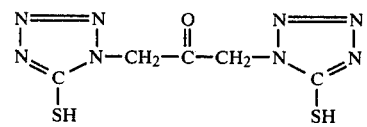

CAUTION: This compound EXPLODES at approximately 205°–210° C.

15. The ether filtrate of step 14 is evaporated to dryness on the vacuum rotary evaporator (50° C. bath). Approximately 42 to 48 grams of crystalline 1-carboxymethyl-5-mercaptotetrazole containing approximately 0.01–0.05 mole of 1-methyl-5-mercaptotetrazole is recovered.

16. The crystals are dissolved in 420 ml. of absolute ethanol (approximately 100 mg./ml.). The solution is warmed to 50°–60° C.

17. To the hot solution of step 16, 310 ml. of a 41% sodium 2-ethylhexanoate (SEH) solution in isopropanol is added with very rapid stirring over a 10 minute period. A crystalline precipitate forms. The mixture is slurried at 50°–60° C. for 20 minutes.

18. The mixture is filtered hot (50°–60° C.) through a heated Buchner funnel (11 cm-SS-No. 604 paper). The crystals are washed with 75 ml. of 50° C. ethanol.

19. The ethanol damp crystals of step 18 are slurried in 200–300 ml. of ethanol. The slurry is passed through a 200 mesh screen. The slurry is heated to 50°–60° C. for 5 minutes with rapid stirring (unreacted-sodium 1-methyl-5-mercaptotetrazole is very soluble in hot ethanol).

20. The crystals are collected at 50°–60° C. on a 11 cm-SS No. 604 paper in a heated Buchner funnel. The crystals are washed with 75–100 ml. of ethanol and vacuum dried at 50°–60° C. for 24–48 hours. Yield: 40–48 grams of di-sodium 1-carboxymethyl-5-mercaptotetrazole (free of 1-methyl-5-mercaptotetrazole as observed by NMR).

B.
7-Amino-3-(1-carboxymethyltetrazol-5-ylthiomethyl)-3-cephem-4-carboxylic acid

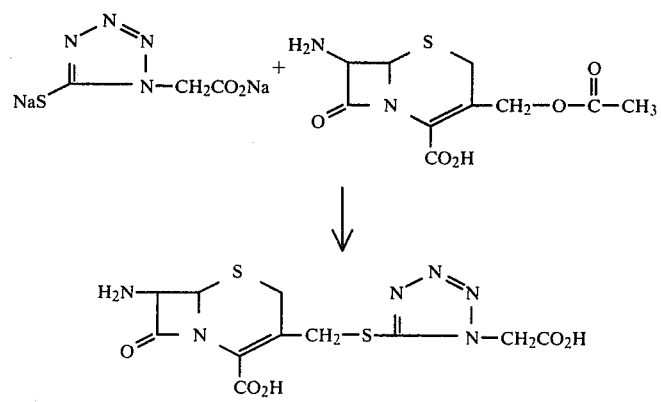

1. Into a 3 necked flask set up with an agitator, a temperature regulator, thermometer and a nitrogen inlet tube, place 18 grams (0.066 mole) of 7-aminocephalosporanic acid, and 300 ml. of 0.1 M pH 6.4 phosphate buffer (20.7 grams of sodium phosphate, monobasic 0.1H$_2$O+8.5 grams of sodium phosphate, dibasic, anhydrous, q.s. to 2 liters).

2. With agitation of the mixture described in step 1, add 1.5 grams of sodium bisulfite and 16 grams (0.078 moles) of 1-carboxymethyl-5-mercaptotetrazole disodium.

3. With agitation continuing, bubble nitrogen through the mixture of 10 minutes.

4. Maintaining agitation and nitrogen inflow, heat the slurry over a 20 minute period to 56° C. During this time interval, 6.5 grams of sodium bicarbonate is added in small increments.

5. With continued agitation and nitrogen inflow, maintain the temperature of the solution at 56° C. for 4 hours. The pH should remain at between 6.2–6.6.

6. Cool the reaction mixture in an ice bath to 5° C.

7. Add 50 ml. of a 1:1 phosphoric acid/water solution to the mixture or concentrated HCl to a pH of 2.0–3.0.

8. Collect the product by filtration. Wash the filter cake with 20 ml. of cold water followed by 200 ml. of cold methanol.

9. Air dry the solid to constant weight. (A typical run produced 14.5 grams of product.) This product may vary in color from yellow to dark brown.

10. Pass the product through a 200 mesh stainless steel screen.

11. Suspend 10 grams of the 200 mesh powder in 200 ml. of n-propanol with rapid stirring.

12. Add 2.0 ml. of concentrated hydrochloric acid and stir vigorously for 0.5 hour at room temperature.

13. Filter the slurry. Wash the brown solids with 20 ml. of n-propanol and add the wash to the filtrate (save the filter cake for possible recovery of additional product).

14. Add 1.5 grams of charcoal ("Darco G-60") to the n-propanol filtrate of step 13. Slurry for 0.5 hour. Remove the carbon by filtration. Wash the carbon with 20 ml. of n-propanol and add the wash to the filtrate.

15. With rapid stirring, add triethylamine to the n-propanol filtrate to an apparent pH of 3.0. Crystals form. Slurry for 10 minutes 16. Collect the white crystals by filtration and wash with 30 ml. of n-propanol, 50 ml. of methanol, and vacuum dry at 40° C. for 24 hours. Yield: 4 to 8 grams of 7-amino-3-(1-carboxymethyltetrazol-5-ylthiomethyl)-3-cephem-4-carboxylic acid.

17. An alternate procedure for the purification of 7-amino-3-(1-carboxylmethyltetrazol-5-ylthiomethyl)-3-cephem-4-carboxylic acid follows:

(a) Slurry 10 grams of the 200 mesh product (from step 10) in 75 ml. of 1 N hydrochloric acid for 10–15 minutes at room temperature. Filter to remove dark brown solids.

(b) Add 2.5 grams of charcoal ("Darco G-60") and slurry for 0.5 hour.

(c) Remove the carbon by filtration. Wash the carbon with 15 ml. of water and add the wash to the filtrate.

(d) With rapid stirring, add concentrated ammonium hydroxide to the filtrate to pH 2.5–3.0. Crystals form.

(e) Slurry the crystal mass for 25 minutes. Remove the crystals by filtration. Wash the crystals with 30 ml. of water, 50 ml. of methanol, and vacuum dry at room temperature. Yield: 4–7 grams of near white crystals.

The other reagents used to prepare the compounds of the present invention are synthesized either as described in the art (e.g. as in the patents and publications noted above) or by strictly analogous procedures. For example when use is made of a D-(−)-α-aminoacid it is prepared according to the procedures set forth in U.S. Pat. Nos. 3,198,804; 3,342,677 or 3,634,418 or by Friis et al., Acta Chem. Scand. 17, 2391–2396 (1966) or by Neims et al., Biochemistry (Wash.) 5, 203–213 (1966) or in other publications on this subject. For convenience and purposes of illustration, however, there are given below some specific examples of such syntheses to prepare carboxylic acids containing a free amino grop which is "blocked" with tert.-butoxycarbonyl.

C.
2-(tert.-Butoxycarbonylaminomethyl)-1,4-cyclohexadienylacetic acid

A solution of 16.5 g. (0.1 mole) of o-aminomethylphenylacetic acid in 1.5 l of liquid ammonia (which had been treated with 50 mg. of Li to remove a trace of moisture) was slowly diluted with 500 ml. of dry t-BuOH. To the solution was added in small portions 3.4 g. (0.5 atom) of Li over a period of 4 hours and the mixture was stirred for 16 hours at room temperature removing the liquid ammonia in a hood and finally evaporated to dryness below 40° C. The residue was dissolved in 500 ml. of water and the solution was chromatographed on a column of IR-120 (H$^+$, 700 ml.) resin and eluted with 1% NH$_4$OH solution. Ninhydrin positive fractions of the eluate were combined and evaporated to dryness. The residue was washed with four 50 ml. portions of hot acetone and recrystallized from 500 ml. of ethanol-water (1:1) to give 11.2 g. (67%) of colorless needles, o-(2-aminomethyl-1,4-cyclohexadienyl)acetic acid. M.p. 183° C.

IR: $\nu_{max}^{nuj}$ 1630, 1520, 1380, 1356 cm$^{-1}$.
NMR: $\delta^{D_2O+K_2CO_3}$ 2.72

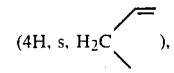

(4H, s, H$_2$C ), 3.01 (2H, s, CH$_2$CO), 3.20 (2H, s, CH$_2$-N), 5.78

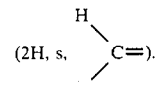

(2H, s, C=).

Anal. Calcd. for C$_9$H$_{13}$NO$_2$: C, 64.65; H, 7.84; N, 8.38. Found: C, 64.77; H, 8.06; N, 8.44.

Improved Procedure for the Preparation of o-(2-aminomethyl-1,4-cyclohexadienyl)-acetic acid

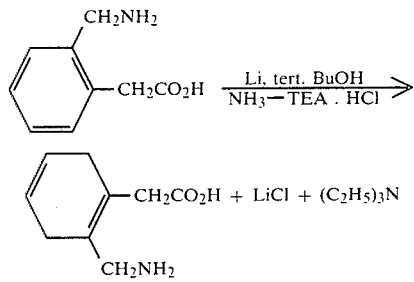

The procedure used by Welch, Dolfini and Giarrusso in U.S. Pat. No. 3,720,665 (Example 1) to make D-2-amino-2-(1,4-cyclohexadienyl)acetic acid was adapted. A solution of 830 ml. of distilled liquid ammonia was dried with 40 mg. of lithium under an argon atmosphere. To this stirred solution was added 11.0 g. (0.07 mole) of 2-aminomethylphenylacetic acid and 340 ml. of tert. butyl alcohol. A total of 1.6 g. (0.225 mole) of lithium was added to the vigorously stirred solution over a period of 2 hours. The grey mixture was then treated with 35 g. (0.215 mole) of triethylamine (TEA) hydrochloride and stirred overnight at room temperature for 18 hours. The tert. butyl alcohol was removed at 40° (15 mm.) to yield a white residue which was dried in vacuo over $P_2O_5$ overnight. The solid was dissolved in 30 ml. of 1:1 methanol-water and added with stirring to 3.5 l. of 1:1 chloroform-acetone at 5°. The mixture was stirred for 20 min. and the amino acid, α-(2-aminomethyl-1,4-cyclohexadienyl) acetic acid, was collected and dried for 16 hours in vacuo over $P_2O_5$ to yield 6.3 g. (58%) of white crystals, m.p. 190° decomp. The IR and NMR spectra were consistent for the structure.

A solution of 19.31 g. (0.135 m) of tert.-butoxycarbonylazide in 152 ml. of tetrahydrofuran (THF) was added to a stirred solution of 14.89 g. (0.09 m) of 2-aminomethyl-1,4-cyclohexadienylacetic acid and 7.20 g. (0.18 m) of sodium hydroxide in 281 ml. of water. The solution was stirred for 18 hour at 25° and then filtered thru diatomaceous earth (Super-cel). The THF was removed at 40° (15 mm) and the residual solution was washed with ether (2×175 ml.) and acidified with 6 N hydrochloric acid (HCl). The mixture was stirred in an ice-bath and the precipitate was collected and dried for 18 hr. in vacuo over $P_2O_5$ at 25° to yield 17.3 g. (72.6%) of 2-(tert.-butoxycarbonylaminomethyl)-1,4-cyclohexadienylacetic acid as a white powder. The IR and NMR spectra were consistant for the structure.

D.
D-(—)-p-Hydroxy-α-tert.-butoxycarboxamidophenylacetic acid

In a mortar 5.65 g. (0.14 m) of magnesium oxide and 11.7 g. (0.07 m) of D-(—)-p-hydroxyphenylglycine were triturated and added to 177 ml. of 50% dioxane. Slowly 20.0 g. (0.14 m) of tert.-butoxycarbonylazide was added to the rapidly stirring mixture and stirred for 20 hours at 45° to 50°. The mixture was then diluted out with 710 ml. of ice water and 177 ml. of ethyl acetate. The mixture was filtered and the filtrate separated into 2 phases. The organic phase was washed 3×50 ml. with 3% sodium bicarbonate solution and 3×50 ml. with water. All the water phases were combined, cooled and adjusted to pH 5.0 with conc. hydrochloric acid. The product was extracted 3×125 ml. into ethyl acetate. The ethyl acetate was washed 2×50 ml. with water, dried over magnesium sulfate and then evaporated at 35° at 15 mm to an oil. The oil was triturated with "Skellysolve B" to yield D-(—)-p-hydroxy-α-tert.-butoxycarboxamidophenylacetic acid as a white solid. This product was collected and dried 18 hr. in vacuo over $P_2O_5$ at 25° to yield 13.5 g. (72.2%) of off-white powder. M.p. 102°. The IR and NMR spectra were consistent for the structure.

E. D-(—)-α-tert.-Butoxycarboxamidophenylacetic acid

The procedure followed was that used above for D-(—)-p-hydroxy-α-tert.-butoxycarboxamidophenylacetic acid. Two crops of sample were obtained to yield 5.2 g. (30%) M.p. 82°. The IR and NMR spectra were consistent for the structure.

F.
2-(tert.-Butoxycarbonylaminomethyl)1,2-cyclohexenylacetic acid which is also named [2-(N-t-Butoxycarbonylamino)methyl-1-cyclohexen-1-yl]acetic acid (a)
α-[2-(t-Butoxycarbonylaminomethyl)-1,4-cyclohexadienyl]acetic acid (1)

To a stirred solution of 8.0 g. (0.048 mole) of α-(2-aminomethyl-1,4-cyclohexadienyl)acetic acid and 3.8 g. (0.096 mole) of NaOH in 150 ml. of water was added a solution of 10.3 g. (0.072 mole) of t-butoxycarbonylazide in 80 ml. of THF and the mixture was stirred for 18 hours at room temperature. The THF was removed under reduced pressure and the residual solution was washed with ether (2×100 ml.), acidified with 6 N HCl and extracted with ether (3×100 ml.). The combined extracts were washed with water (2×100 ml.) and a saturated NaCl solution (100 ml.), dried with $Na_2SO_4$ and evaporated to dryness. The oily residue was triturated with n-hexane to give 10.5 g. (82%) of colorless powder 1 melting at 113° C.

IR: $\nu_{max}^{nuj}$ 3370, 1715, 1640, 1530, 1280, 1160 cm$^{-1}$.
NMR: $\delta_{ppm}^{CDCl_3}$ 1.45 (9H, s, t-Bu-H̲),

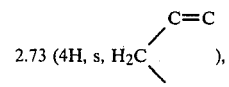
2.73 (4H, s, $H_2C$ ), 3.16 (2H, s, C̲H̲$_2$CO), 3.76 (2H, d, 6Hz, C̲H̲$_2$N) 4.90 (1H, m, NH),

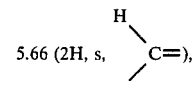
5.66 (2H, s, ), 10.6 (1H, br-s, COOH).
Anal. Calcd. for $C_{14}H_{21}NO_4$: C, 62.90; H, 7.92; N, 5.24. Found: C, 63.13; H, 8.21; N, 5.26.

(b)
[2-(N-t-Butoxycarbonylamino)methyl-1-cyclohexen-1-yl]-acetic acid (2)

A solution of [2-(N-t-butoxycarbonylamino)methyl-1,4-cyclohexadien-1-yl]acetic acid (1), (1.33 g., 5 mmoles) in 3% ammonium hydroxide (10 ml.) was hydrogenated at 40 psi with palladium on charcoal (10%, 0.2 g.). A theoretical amount of hydrogen was taken up in 3 hours. The catalyst was removed and the filtrate was acidified to pH 2 with dil. HCl and extracted with ethyl acetate (2×50 ml.). The combined extracts were washed with water (20 ml.), dried with $Na_2SO_4$ and evaporated under reduced pressure to afford an oil (1.34 g.) which solidified on standing for several days. Recrystallization from n-hexane-ethyl acetate gave 1.2 g. (90%) of 2 as colorless prisms melting at 118°–119° C.

IR: $\nu_{max}^{nujol}$ 3450, 1730, 1660, 1510 cm$^{-1}$.
NMR: $\delta_{ppm}^{CDCl_3}$ 1.58 (9H, s, t-butyl-H̲), 1.50–1.90 (4H, m, —C̲H̲$_2$—), 1.90–2.20 (4H, m, allylic methylene-H̲), 3.18 (2H, s, CH$_2$—CO), 3.78 (2H, d, 6 Hz, CH$_2$—N), 5.00 (1H, br-s, NH), 8.98 (1H, br-s, COOH).

Anal. Calcd. for $C_{14}H_{23}NO_4$: C, 62.43; H, 8.61; N, 5.20. Found: C, 62.12; H, 8.77; N, 5.37.

G. 2-t-Butoxycarbonylaminomethyl-4-hydroxyphenylacetic acid is prepared, for example, according to U.S. Pat. No. 3,823,141.

H. o-(tert.-Butoxycarbonylaminomethyl)phenylthioacetic acid is prepared, for example, according to U.S. Pat. No. 3,657,232 and see also U.S. Pat. No. 3,813,390.

I. β-[o-(tert.-Butoxycarbonylaminomethyl)phenyl]-propionic acid is prepared, for example, according to U.S. Pat. No. 3,813,391.

J. D-(—)-N-t-Butoxycarbonyl-2-(3'-methyl-4'-hydroxyphenyl)glycine 2-(3'-Methyl-4'-hydroxyphenyl)glycine A solution of 59.02 g. (0.6 mole) of 75% glyoxylic acid in 100 ml. of water was added to a suspension of 54.6 g. (0.5 mole) of 2-methylphenol and 140 ml. of conc. ammonium hydroxide in 400 ml. of water at room temperature. The temperature of the mixture rose to 37°. The mixture was stirred at room temperature for 65 hours. The solution, initially at pH 10.1, was adjusted to pH 6.8 with 6 N hydrochloric acid causing the product to crystallize. The product was collected by filtration, washed with water and dried in vacuo over phosphorus pentoxide giving 31.5 g. (34.8%) of 2-(3'-methyl-4'-hydroxyphenyl)glycine; decomp. 196°-199°. The infrared and nuclear magnetic resonance spectra were consistent for the desired product. Reference: Belgium Pat. No. 774,029 to Beecham Group Limited, 1972 (Farmdoc 27, 122T) which reports m.p. 205°-207° C.

Anal. Calcd. for $C_9H_{11}NO_3$: C, 59.66; H, 6.13; N, 7.73. Found: C, 57.68; H, 6.23; N, 7.47; $H_2O$, 2.34. Found, corrected for 2.34% $H_2O$: C, 59.06; H, 6.12; N, 7.67.

D,L-N-Chloroacetyl-2-(3'-methyl-4'-hydroxyphenyl)glycine

A suspension of 20.2 g. (0.112 mole) of D,L-2-(3'-methyl-4'-hydroxyphenyl)glycine in 175 ml. of water was adjusted to pH 10.3 with 20% sodium hydroxide causing a solution. The solution was cooled in an ice bath. Chloracetic anhydride (38.2 g., 0.224 mole) was added all at once and the pH of the reaction mixture was maintained at pH 10 by the addition of 20% sodium hydroxide until no further pH change was detected. Then reaction mixture was stirred an additional 10 min. in the cold. The reaction mixture was then acidified to pH 2.0 with 6 N hydrochloric acid causing the product to crystallize. The product was collected by filtration, washed with water and air dried. Recrystallization from 200 ml. of hot water gave 13.7 g. (47.4%) of D,L-N-chloroacetyl-2-(3'-methyl-4'-hydroxyphenyl)glycine. The infrared and nuclear magnetic resonance spectra were consistent for the desired product.

Anal. Calcd. for $C_{11}H_{12}NO_4Cl \cdot H_2O$: C, 47.92; H, 5.118; N, 5.081. Found: C, 48.11; H, 5.16; N, 5.15.

D-(—)-N-chloroacetyl-2-(3'-methyl-4'-hydroxyphenyl)glycine

D,L-N-Chloroacetyl-2-(3'-methyl-4'-hydroxyphenyl)glycine (5.0 g., 0.0194 mole) and L-ephenamine acetate (6.1 g., 0.0213 mole) were dissolved in 50 ml. of isopropyl alcohol by heating on a steam bath. Water (50 ml.) was added and upon cooling, the L-ephenamine salt crystallized. The salt was collected by filtration and air dried.

The salt was suspended in 30 ml. of water and 50 ml. of methylene chloride and the mixture adjusted to pH 10.0 with 20% sodium hydroxide. The phases were separated and the aqueous phase was extracted twice more with methylene chloride.

The aqueous solution was then adjusted to pH 2.0 with 6 N hydrochloric acid causing the product to crystallize. The product was collected by filtration and dried in vacuo over phosphorus pentoxide affording 0.9 g. (36.1%) of D-(—)-N-chloroacetyl-2-(3'-methyl-4'-hydroxyphenyl)glycine; m.p. 170°-172°, $[\alpha]_D^{24°} = 185.9°$ (C 1, 95% EtOH). The infrared and nuclear magnetic resonance spectra were consistent for the desired product.

Anal. Calcd. for $C_{11}H_{12}NO_4Cl$: C, 51.27; H, 4.696; N, 5.436. Found: C, 51.21; H, 4.77; N, 5.29.

1,2-Diphenyl-2-methylaminoethanol, commonly called ephenamine (per Federal Register, June 7, 1951), has the structure

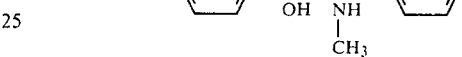

The compound is also named N-methyl-1,2-diphenyl-2-hydroxy-ethylamine or alpha, beta-diphenyl-beta-hydroxy-N-methyl-ethylamine or 1,2-diphenyl-2-methylamino-1-ethanol.

This invention utilizes only the levo-erythroisomer. Methods for its preparation and reaction with penicillin G were described in U.S. Pat. Nos. 2,645,638 (V. V. Young) and 2,768,081 (F. H. Buckwalter). The latter reviews earlier literature as does W. B. Wheatley et al., J. Org. Chem., 18(11), 1564–1571 (1953). It was used to resolve racemic phenoxymethyl penicillin by Sheehan et al., J. Am. Chem. Soc., 81, 3089–3094 (1959); see especially p. 3091.

D-(—)-2-(3-Methyl-4'-hydroxyphenyl)glycine

D-(—)-N-Chloroacetyl-2-(3'-methyl-4'-hydroxyphenyl)glycine (11.1 g., 0.0431 mole) was combined with 100 ml. of 2 N hydrochloric acid and the mixture was refluxed for 1.5 hours. The solution was cooled and the pH adjusted to 5.0 with 20% sodium hydroxide causing the product to crystallize. The product was collected by filtration, washed with water and dried in vacuo over phosphorus pentoxide giving 7.4 g. (94.7%) of D-(—)-2-(3'-methyl-4'-hydroxyphenyl)glycine; decomp. 205°-209°, $[\alpha]_D^{24} = -152.6°$ (C 1, 1.N HCl). The infrared and nuclear magnetic resonance spectra were consistent for the desired product.

Anal. Calcd. for $C_9H_{11}NO_3$: C, 59.66; H, 6.13; N, 7.73. Found: C, 58.62; H, 5.49; N, 7.78; $H_2O$, 1.46. Found, corrected for 1.46% $H_2O$: C, 59.48; H, 5.41; N, 7.84.

D-(—)-N-t-Butoxycarbonyl-2-(3'-methyl-4'-hydroxyphenyl)glycine

To a slurry of 7.2 g. (0.0397 mole) of D-(—)-2-(3'-methyl-4'-hydroxyphenyl)glycine and 3.2 g. (0.08 mole) of powdered magnesium oxide stirred in 100 ml. of 50% dioxane at room temperature, 9.7 g., (0.068 mole) of t-butoxycarbonyl azide was added dropwise. The reaction mixture was then heated to 42°-45° under a nitrogen atmosphere for 19 hours. The mixture was then diluted with 100 ml. of ice water. The solution was layered with ethyl acetate and filtered to remove some insoluble material that had separated. The aqueous phase of the filtrate was separated and extracted twice more with ethyl acetate. The aqueous solution was then adjusted to pH 5.0 with 42% phosphoric acid and extracted 5 times with ethyl acetate. The combined organic extracts were washed 3 times with water, dried over sodium sulfate and the solvent removed at reduced pressure leaving an oil. The oil was dried in vacuo over phosphorus pentoxide resulting in 10.6 g. (95%) of D-(−)-N-t-butoxycarbonyl-2-(3'-methyl-4'-hydroxyphenyl)glycine. The infrared spectrum was consistent for the desired structure.

K.
D-(−)-N-t-Butoxycarbonyl-2-(3'-methoxy-4'-hydroxyphenyl)glycine

2-(3'-Methoxy-4'-hydroxyphenyl)glycine

A solution of 59.2 g. (0.6 mole) of 75% glyoxylic acid in 100 ml. of water was added to a suspension of 62.07 g. (0.5 mole) of 2-methoxyphenol and 140 ml. of concentrated ammonium hydroxide in 400 ml. of water at room temperature. The temperature of the mixture rose to 35°. The mixture was stirred at room temperature for 65 hours. The product that had crystallized was collected by filtration, washed with water, then acetone and dried in vacuo over phosphorus pentoxide giving 57.4 g. (58.2%) of 2-(3'-methoxy-4'-hydroxyphenyl)glycine; decomp. 218°–220° (Lit. 240°). The infrared and nuclear magnetic resonance spectra were consistent for the desired product.

Anal. Calcd. for $C_9H_{11}NO_4$: C, 54.82; H, 5.62; N, 7.10. Found: C, 53.77; H, 5.91, N, 6.97; $H_2O$, 1.13 Found, corrected for 1.13% $H_2O$: C, 54.38; H, 5.85; N, 7.05.

Reference: B. Block, *Z. Physiol. Chem.*, 98, 226 (1917).

Resolution of 2-(3'-Methoxy-4'-hydroxyphenyl)glycine

A. Methyl 2-(3'-Methoxy-4'-hydroxyphenyl)glycinate

A cooled suspension of 94 g. (0.476 mole) of 2-(3'-methoxy-4'-hydroxyphenylglycine in 500 ml. of absolute methanol was gassed at a rapid rate with HCl for 20 min. At first a clear solution was obtained and then crystalline product separated in quantity. After 20 hours the methyl ester hydrochloride was filtered and washed sparingly with methanol; 99.6 g. after air drying. A cooled solution of the hydrochloride in 800 ml. of water was adjusted to pH 8 (NaOH) giving a crystalline precipitate of the ester free base; 81.3 g. The IR and NMR spectra were consistent.

Anal. Calcd. for $C_{10}H_{13}NO_4$: C, 56.86; H, 6.20; N, 6.63. Found: C, 56.46; H, 6.28; N, 6.55; $H_2O$, 0.59.

B. D-(−)-2-(3'-Methoxy-4'-hydroxyphenyl)glycine

A mixture of 50 g. (0.237 mole) of methyl 2-(3'-methoxy-4'-hydroxyphenyl)glycinate, 19 ml. (0.333 mole) of acetic acid and 1 l. of i-PrOH (isopropyl alcohol) was heated to boiling giving a partial solution. Dibenzoyl-d-tartaric acid monohydrate (89.2 g., 0.237 mole) was added with good stirring and then the mixture was refluxed. Soon the salt started to crystallize. The heat was shut off and the flask was allowed to cool slowly to room temperature. After cooling in an ice bath the precipitate was collected by filtration. The filtrate was concentrated to about one-third of its initial volume giving a small second crop of salt; total yield of both crops 54.1 g. after air drying (solid A; see below).

The filtrate was concentrated free of solvent. The viscous reside was combined with 300 ml. of 1 N HCl and the mixture extracted with 400 ml. of of $CHCl_3$. The $CHCl_3$ phase was extracted twice with 100 ml. portions of 1 N HCl. The combined HCl extracts were concentrated briefly to remove residual $CHCl_3$ and refluxed for 1 hr. The solution was concentrated to a small volume causing the amino acid HCl salt to crystallize. The product was collected by filtration and recrystallized from 50 ml. of 1 N HCl. A solution of the product in 200 ml. of water was adjusted to pH 4.5 (NaOH). The mixture was heated nearly to boiling and allowed to cool to precipitate D-(−)-2-(3'-methoxy-4'-hydroxyphenyl)glycine as fluffy needle-like crystals. After cooling overnight, the product was collected by filtration, washed sparingly with water and methanol and dried at 40°; 8.7 g., $[\alpha]_D^{24°} = -136.5°$ (c 1 1 N HCl). The IR and NMR spectra were fully consistent.

Anal. Calcd. for $C_9H_{11}NO_4.H_2O$: C, 50.23; H, 6.09; N, 6.51; $H_2O$, 8.37. Found: C, 50.43; H, 6.23; N, 6.51; $H_2O$, 8.95.

C. L-(+)-2-(3'-Methoxy-4'-hydroxyphenyl)glycine

Solid A above (54.1 g.) was suspended in 300 ml. of 1 N HCl and 500 ml. of $CHCl_3$ with good agitation. The salt did not break up readily in this system, therefore, the $CHCl_3$ was separated as well as possible and 300 ml. of MIBK added with good agitation. The MIBK phase was extracted with an additional 200 ml. of 1 N HCl in 3 portions. The combined and filtered HCl extracts were concentrated briefly to remove residual solvents and heated at reflux for 1 hr. to hydrolyze the ester. The reaction mixture was concentrated to a small volume. After cooling in an ice bath the crystalline amino acid HCl salt was collected by filtration. The salt was recrystallized from 75 ml. of 1 N HCl, dissolved in 500 ml. of water by warming, the solution polish filtered and adjusted to pH 4.5 (NaOH) causing the zwitterion to crystallize. The mixture was heated to boiling, filtered, and stored in the cold to precipitate the crystalline product, L-(+)-2-(3'-methoxy-4'-hydroxyphenyl)glycine. The product was collected by filtration, washed sparingly with water and methanol and dried at 40°; 9.6 g., $[\alpha]_D^{24°} = +127.2°$ (c 1 1 N HCl). The IR and NMR spectra were consistent.

Anal. Calcd. for $C_9H_{11}NO_4.H_2O$: C, 50.23; H, 6.09; N, 6.51; $H_2O$, 8.37. Found: C, 50.53; H, 6.06; N, 6.62; $H_2O$, 7.46.

D-(−)-N-(t-Butoxycarbonyl)-2-(3'-methoxy-4'-hydroxyphenyl)glycine

A mixture of 8.6 g. (0.04 mole) of D-(−)-2-(3'-methoxy-4'-hydroxyphenyl)glycine, 3.2 g. (0.08 mole) of magnesium oxide, 9.7 g. (0.068 mole) of t-butoxycarbonyl azide and 240 ml. of 1:1 dioxane-water was stirred and heated at 45°–50° for 20 hours under a nitrogen atmosphere. The cooled reaction mixture was diluted with 240 ml. of ice water, filtered and extracted once with ethyl acetate. The acidified (pH 2) aqueous phase was extracted 5 times with ethyl acetate. The combined and dried ($Na_2SO_4$) ethyl acetate extracts were concentrated free of solvent at reduced pressure giving the product as a viscous oil; 6.3 g.

L.
D-(−)-N-t-Butoxycarbonyl-2-(4-acetoxyphenyl)glycine

This compound is prepared by substitution for the D-(−)-2-(3′-methyl-4′-hydroxyphenyl)glycine in the procedure set out above of an equimolar weight of D-(−)-2-(4-acetoxyphenyl)glycine prepared in the following manner.

Preparation of D-(−)-2-amino-2-(4-acetoxyphenyl)acetic acid

Method A (in acetic acid as solvent)

203.5 g. (1 mole) of D-(−)-p-hydroxyphenylglycine chloride 800 ml. of acetic acid and 314 g. (4 moles) of acetyl chloride are stirred 48 hours at room temperature. The solid is collected, washed three times with acetone (3×250 ml.) and twice with ethanol (2×250 ml.) and dried at 40°. Yield 210 g. (85.4%). This hydrochloride is dissolved in 3.0 l of water; the solution is cooled to +5° to 10° C. and the pH adjusted to 4.5 with 20% NH$_4$OH. The suspension is stirred 1 hour at 5° C. and the solid collected, washed twice with water and twice with acetone, and dried at 40° C. Yield 133 g. (64% from D-(−)-p-hydroxyphenylglycine). αD (1% HCl N/10)=−104.5.

Method B (in methylene chloride)

4.07 g. (0.02 Mole) of D-(−)-p-hydroxyphenylglycine hydrochloride, 30 ml. of methylene chloride and 6.28 g. (0.08 mole) of acetyl chloride are stirred 48 hours at room temperature. The solid is collected, washed twice with acetone and twice with ethanol. Yield 4.17 g. (84.5%). Anal. cl=14.8% (calculated 14.4%).

Method C (in trifluoroacetic acid)

1.67 g. (0.01 Mole) of D-(−)-p-hydroxyphenylglycine is added with stirring, to 10 ml. of trifluoroacetic acid at room temperature. After dissolution, 1.57 g. (0.02 mole) of acetyl chloride is added. After a slightly exothermic reaction, a solid appears. The suspension is stirred 1½ hr. at room temperature and the trifluoroacetic acid is removed in vacuum. The remaining solid is collected washed with methylene chloride and with ethanol. The D-(−)-2-amino-2-(4-acetoxyphenyl)acetic acid is identical to that prepared by Methods A or B Yield: 1.9 g. (75%)

M.
D-(−)-N-t-Butoxycarbonyl-2-(1′-cyclohexenyl)glycine

This compound is prepared by substitution for the D-(−)-2-(3′-methyl-4′-hydroxyphenyl)glycine in the procedure set our above of an equimolar weight of D-(−)-2-(1′-cyclohexenyl)glycine prepared according to Belgium No. 773,773 (Farmdoc 25,515T) or U.S. Pat. No. 3,824,237.

N.
D-(−)-N-t-Butoxycarbonyl-2-(3′-chloro-4′-hydroxyphenyl)glycine is prepared, for example, as disclosed in U.S. Pat. No. 3,489,751.

O.
D-(−)-N-t-Butoxycarbonyl-2-(1′,4′-cyclohexadienyl)glycine

This compound is prepared by substitution for the D-(−)-2-(3′-methyl-4′-hydroxyphenyl)glycine in the procedure set out above of an equimolar weight of D-(−)-2-(1′,4′-cyclohexadienyl)glycine (also named D-2-amino-2-(1,4-cyclohexadienyl)acetic acid) prepared according to U.S. Pat. No. 3,485,819.

P.
D-(−)-2-tert.-Butoxycarboxamido-3-(1′,4′-cyclohexadienyl)propionic acid This compound is prepared by substitution for the D-(−)-2-(3′-methyl-4′-hydroxyphenyl)glycine in the procedure set out above of an equimolar weight of D-2-amino-3-(1,4-cyclohexadienyl)propionic acid prepared according to U.S. Pat. No. 3,485,819.

Q.
D-(−)-2-tert.-Butoxycarboxamido-3-(4′-methoxy-1′,4′-cyclohexadienyl)propionic acid This compound is prepared by substitution for the D-(−)-2-(3′-methyl-4′-hydroxyphenyl)glycine in the procedure set out above of an equimolar weight of D-2-amino-3-(4′-methoxy-1,4-cyclohexadienyl)propionic acid prepared according to U.S. Pat. No. 3,485,819.

R. 2-t-Butoxycarbonylaminomethylphenyl-acetic acid is prepared, for example, according to U.S. Pat. No. 3,766,175.

S.
N-tert.-Butoxycarbonyl-1-aminocyclohexanecarboxylic acid

This compound is prepared by substitution for the D-(−)-2-(3′-methyl-4′-hydroxyphenyl)glycine in the procedure set out above of an equimolar weight of 1-amino-cyclohexanecarboxylic acid.

T. D-(−)-α-tert.-Butoxycarboxamido-3-thienylacetic acid is prepared, for example, according to U.S. Pat. Nos. 3,634,418, 3,198,804 and appropriate references cited therein.

U. D-(−)-α-tert.-Butoxycarboxamido-2-thienylacetic acid is prepared, for example, according to U.S. Pat. Nos. 3,634,418, 3,198,804 and appropriate references cited therein.

V.
β-(2-tert.-Butoxycarbonylaminomethyl-1,4-cyclohexadienyl)-propionic acid (a) β-(2-Aminomethyl-1,4-cyclohexadienyl)propionic acid A solution of β-(o-aminomethylphenyl)propionic acid (10.74 g., 60 mmoles) in liquid ammonia (1000 ml.) (pretreated with ca. 50 mg. of lithium to remove a trace of water) was cautiously diluted with dry t-BuOH (300 ml.). To the solution was added portionwise lithium (2.08 g., 0.3 atom) over a period of 3 hr. and the mixture was stirred overnight to remove liquid ammonia and evaporated to dryness. The residue was dissolved in water (200 ml.). The solution was chromatographed on a column of IR-120 (H$^+$ form, 500 ml.) and eluted continuously with water (2000 ml.) and 5% ammonium hydroxide (ca. 2000 ml.). Ninhydrin positive fractions were combined, evaporated to dryness and the residue was crystallized from 90% ethanol to afford colorless needles. Yield of β-(2-aminomethyl-1,4-cyclohexadienyl)propionic acid was 9.68 g. (89%) M.p. 228°–229° C.

IR: $\nu_{max}^{nuj}$ 2130, 1540, 1300 cm$^{-1}$.

NMR: $\delta_{ppm}^{D_2O}$ 2.68 (4H, s, CH$_2$CH$_2$CO), 2.74 (4H, s, ring methylene), 3.68 (2H, s, CH$_2$N), 5.79 (2H, s, ring vinyl-H).

Anal. Calcd. for $C_{10}H_{15}NO_2$: C, 66.27; H, 8.34; N, 7.73. Found: C, 66.25, 66.31; H, 8.35, 8.52; N, 7.61, 7.71.

(b)
β-(2-t-Butoxycarbonylaminomethyl-1,4-cyclohexadienyl)propionic acid

To a mixture of β-(2-aminomethyl-1,4-cyclohexadienyl)propionic acid (1.40 L g., 7.7 mmoles) and triethylamine (2.02 g., 20 mmoles) in 50% aqueous THF (20 ml.) was added a solution of t-butyl azidoformate (1.43 g., 10 mmoles) in THF (5 ml.) and the reaction mixture was stirred overnight at room temperature. The mixture was washed with ether (2×20 ml) and the aqueous layer was acidified to pH 2 with dil. hydrochloric acid. The mixture was extracted with chloroform (4×30 ml.) and the combined extracts were washed with water and dried. Evaporation of the extracts under reduced pressure afforded β-(2-tert.-butoxycarbonylaminomethyl-1,4-cyclohexadienyl)propionic acid as a colorless oil. Yield, 2.10 g. (97%).

IR: $\nu_{max}^{liq}$ 1700, 1510, 1240, 1160 cm$^{-1}$.

NMR: $\delta_{ppm}^{CDCl_3}$ 1.47 (9H, s, t-Bu-H), 2.45 (4H, s, $CH_2CH_2$), 2.69 (4H, s, ring methylene), 3.80 (2H, d, 5 Hz, $CH_2N$), 5.70 (2H, s, ring vinyl-H).

W.
β-(2-t-Butoxycarbonylaminomethyl-1-cyclohexenyl)-propionic acid

β-(2-t-Butoxycarbonylaminomethyl-1,4-cyclohexadienyl)propionic acid (0.92g, 3.2 mmoles) was dissolved in 3% aqueous ammonium hydroxide (20 ml.) and hydrogenated at 30 psi with palladium on carbon (10%, 0.1 g.) in a Parr apparatus for 3 hr. The mixture was filtered and the filtrate was acidified to pH 2 with dil. hydrochloric acid and extracted with ethyl acetate (3×30 ml.). The combined extracts were washed with a small amount of water and dried. Removal of the solvent under reduced pressure afforded β-(2-t-butoxycarbonylaminomethyl-1-cyclohexenyl)-propionic acid as an oil; yield 0.84 g. (91%).

IR: $\nu_{cm-1}^{liq}$ 3350 (NH), 3200-2400 (COOH), 1750 (CO), 1250, 1165 (BOC).

NMR: $\delta_{ppm}^{CDCl_3}$ 1.48 (9H, s, t-Bu), 1.5-1.8 (4H, m, $CH_2CH_2$), 1.8-2.2 (4H, m, allyl-$CH_2$), 2.4 (4H, $CH_2CH_2$—CO), 3.72 (2H, s, N—$CH_2$).

X.
D-(−)-N-tert.-Butoxycarbonyl-2-(4'-hydroxymethylphenyl)glycine

This compound, which is also named D-(−)-N-t-butoxycarbonyl-p-hydroxymethyl-phenylglycine, is prepared according to South Africa No. 73/4055; for convenience the pertinent disclosure therein is reproduced below.

To a solution of 1.4-benzenedicarboxaldehyde (50.0 g., 0.373 mole) in 200 ml. of dry tetrahydrofuran (THF) under nitrogen in an ice bath was added dropwise lithium tri(t-butoxy)aluminum hydride (104.0 g., 0.410 mole) dissolved in 500 ml. of dry tetrahydrofuran. After stirring for one half hour in an ice bath, the reaction mixture was poured into 2 l. of ice cold 2 N hydrochloric acid. The aqueous solution was extracted with four 800 ml. portions of ether. The combined ether layers were washed with 500 ml. of ice cold 5% sodium bicarbonate solution and then with 500 ml. of saturated sodium chloride solution. After drying, the ether was removed under reduced pressure to give 46 g. of crude p-hydroxymethylbenzaldehyde. The crude product was chromatographed over 1 kg. of neutral alumina and the fractions eluted with ether and concentrated. Upon cooling there crystallized out p-hydroxymethylbenzaldehyde (17.0 g., 35% yield), m.p. 44.5°–46° C.

To a stirred mixture of p-hydroxymethylbenzaldehyde (10.0 g., 0.0735 mole) and ammonium carbonate (17.1 g., 0.15 mole) in 110 ml. of 60% ethanol heated to 50° C. there was added dropwise sodium cyanide (4.0 g., 0.081 mole) dissolved in 10 ml. water. The mixture was stirred and heated to 55°–60° C. for three hours and then the temperature raised to 85° C. for one hour. After cooling in an ice bath, the pH of the solution was brought to 6 by the addition of concentrated hydrochloric acid. Upon overnight cooling, the solid which had precipitated was filtered, washed with cold water, and dried. The 5-(p-hydroxymethylphenyl)hydantoin (11.0 g., 72% yield), m.p. 189°–196° (dec.), was used to prepare the amino acid without further purification.

A mixture of 5-(p-hydroxymethylphenyl)hydantoin (10.9 g., 0.053 mole) and barium hydroxide (.8 $H_2O$) (25.5 g., 0.081 mole) in 125 ml. water was stirred and refluxed for 18 hours. After cooling in an ice bath the reaction mixture was diluted with 125 ml. water. The solution was acidified with concentrated sulfuric acid to pH 1, the barium sulfate filtered, and the pH of the filtrate brought to 6 with lead carbonate. After filtration of the lead sulfate, the filtrate was saturated with hydrogen sulfide and the lead sulfide filtered. The aqueous solution was then concentrated to 100 ml. by azeotroping with ethanol under reduced pressure. After cooling, there was precipitated p-hydroxymethylphenylglycine (5.2 g., 54% yield) m.p. 228°–229° C. (dec.). After recrystallization from ethanol-water the compound had m.p. 230°–231° (dec.).

Anal. Calcd. for $C_9H_{11}NO_3$: C, 59.66; H, 6.12; N, 7.73. Found: C, 59.46; H, 6.24; N, 7.93.

To a solution of p-hydroxymethylphenylglycine (8.0 g., 0.044 mole) and triethylamine (8.8 g., 0.087 mole) in 160 ml. water was added t-butoxycarbonyl azide (6.95 g., 0.049 mole) dissolved in 120 ml. tetrahydrofuran. After stirring overnight at room temperature, the reaction mixture was washed twice with 200 ml. portions of ether. The aqueous layer was covered with ether and in an ice bath was acidified to pH 3–3.5 with 3 N hydrochloric acid. The acidic solution was extracted three times with 200 ml. portions of ether. The combined ether layers were washed with saturated sodium chloride solution, dried, and the ether evaporated under reduced pressure. The resulting oil was triturated with chloroform-hexane and the solid filtered off to give dl-N-t-butoxycarbonyl-p-hydroxymethylphenylglycine (7.74 g., 63% yield), m.p. 139°–141.5° (dec.).

Anal. Calcd. for $C_{14}H_{19}NO_5$: C, 59.78, H, 6.81; N, 4.98. Found: C, 59.67; H, 6.76; N, 4.69.

dl-N-t-Butoxycarbonyl-p-hydroxymethylphenylglycine (7.560 g., 0.0269 mole) and quinone (10.199 g., 0.0269 mole) were mixed and dissolved in 110 ml. of boiling ethanol. The solution was allowed to cool to room temperature and to crystallize overnight. The salt was filtered off and the crystallization repeated three times.

The salt (17.76 g., m.p. 198°–201° dec., $[\alpha]_D^{25}$ −149.8, C=1, $CH_3OH$) gave after three recrystallization resolved salt (4.6 g., m.p. 205°–6° dec., $[\alpha]_D^{25}$ −163.4, C=1, $CH_3OH$). An additional recrystallization did not increase the optical rotation.

The (−) quinine salt of (−)-N-t-butoxycarbonyl-p-hydroxymethylphenylglycine was suspended in 75 ml.

water and 175 ml. ether in an ice bath and 3 N hydrochloride acid added to pH 2.5. The ether layer was removed and the aqueous layer extracted twice with 100 ml. portions of ether. The combined ether layers were washed with 100 ml. saturated sodium chloride, dried, and the ether removed under reduced pressure. The residue was triturated with chloroform-hexane and filtered to give D-(−)-N-t-butoxycarbonyl-p-hydroxymethylphenylglycine (1.68 g., 98% recovery), m.p. 111°–113.5° dec., $[\alpha]_D^{25} = -136.5$ (C=1, CH$_3$OH).

The use of an "en-amine" blocking group with a prospective 7-side chain containing a free amine group prior to acylation of a nucleus such as II herein is well known as from U.S. Pat. Nos. 3,223,141, 3,813,390, 3,813,391, 3,823,141 and Belgium No. 773,773. For convenience some specific examples follow.

Sodium 2-[N-(1-carbethoxypropen-2-yl)aminomethyl]-1,4-cyclohexadienyl acetate (4)

To a stirred solution of 460 mg. (0.02 mole) of metallic sodium in 100 ml. of absolute EtOH was added 3.34 g. (0.02 mole) of 2-aminomethyl-1,4-cyclohexadienylacetic acid and 3.1 g. (0.024 mole of ethyl acetoacetate and the mixture was heated to reflux for 4 hours with stirring. The hot reaction mixture was filtered and the filtrate was allowed to keep cold overnight to give 2.0 g. of colorless needles 4 melting at 264° C. The additional product (3.3 g.) was obtained by concentration of the mother liquid. The total yield was 5.3 g. (88%).

IR: $\nu_{max}^{nuj}$ 3300, 1635, 1600, 1570, 1300, 1275, 1170, 1090 cm$^{-1}$.

NMR: $\delta_{ppm}^{D2O}$ 1.23 (3H, t, 7 Hz, CH$_2$C$\underline{H}_3$), 1.96 & 2.25 (3H, s, C=C—C$\underline{H}_3$, cis & trans), 2.70 (4H, s, H$_2$C 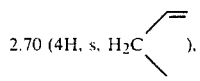 ), 3.04 (2H, s, C$\underline{H}_2$CO), 3.66 & 3.95 (2H, s, C$\underline{H}_2$-N, cis & trans), 4.07 (2H, q, 7 Hz, C$\underline{H}_2$CH$_3$), 4.45 & 4.56 (1H, s, 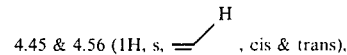, cis & trans), 5.76 (2H, s, 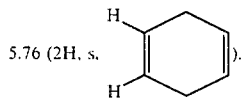 ).

Anal. Calcd. for C$_{15}$H$_{20}$NO$_4$Na: C, 59.79; H, 6.69; N, 4.64. Found: C, 59.69; H, 6.76; N, 4.75.

Sodium D-N-(2-methoxycarbonyl-1-methylvinyl)-α-amino-α-(3'-methyl-4'-hydroxyphenyl)acetate To a stirred solution of 3.02 g. (0.078 mole) of NaOH in 320 ml. of methanol is added 0.08 mole of D-(−)-2-(3'-methyl-4'-hydroxyphenyl)glycine and the resulting mixture is heated at reflux while a solution of 9.6 ml. (0.088 mole) of methyl acetoacetate in 80 ml. of methanol is added over a thirty minute period. After an additional 30 min. refluxing, the methanol is distilled off while toluene is added at the same rate so as to keep approximately the same internal volume. When the internal temperature reaches 100° C. the suspension is cooled in ice water for 4 hours, filtered, washed well with toluene, air dried, and vacuum dried over P$_2$O$_5$ to constant weight to yield solid sodium D-N-(2-methoxycarbonyl-1-methylvinyl)-α-amino-α-(3'-methyl-4'-hydroxyphenyl)acetate.

Sodium D-N-(2-methoxycarbonyl-1-methylvinyl)-α-amino-α-(3'-methoxy-4'-hydroxyphenyl)acetate To a stirred solution of 3.02 g. (0.078 mole) of NaOH in 320 ml. of methanol is added 0.08 mole of D-(−)-2-(3'-methoxy-4'-hydroxyphenyl)glycine and the resulting mixture is heated at reflux while a solution of 9.6 ml. (0.088 mole) of methyl acetoacetate in 80 ml. of methanol is added over a thirty minute period. After an additional 30 min. refluxing, the methanol is distilled off while toluene is added at the same rate so as to keep approximately the same internal volume. When the internal temperature reaches 100° C. the suspension is cooled in ice water for 4 hours, filtered, washed well with toluene, air dried, and vacuum dried over P$_2$O$_5$ to constant weight to yield solid sodium D-N-(2-methoxycarbonyl-1-methylvinyl)-α-amino-α-(3'-methoxy-4'-hydroxyphenyl)acetate.

The similar use of a proton as the protecting group, as in an acid chloride hydrochloride, is equally well known and may be illustrated as follows:

D-(−)-2-(3'-Methoxy-4'-hydroxyphenyl)glycyl chloride hydrochloride is prepared in a high state of purity and very efficiently by the following procedure:

About 0.06 moles of D-(−)-2-(3'-methoxy-4'-hydroxyphenyl)glycine is slurried in 100 ml. of dioxane. The slurry is stirred and COCl$_2$ (phosgene) is passed in while the slurry temperature is held at 50°–58° C. The COCl$_2$ is passed in for a total time of 3.5 hours. A yellow solution is obtained. The solution is purged with nitrogen to expel the excess COCl$_2$. HCl gas is bubbled through the solution for 2.5 hours. The solution is stirred and a small amount is diluted with some ether to obtain some crystals which are added to the batch as seed. The solution is stirred at 20°–25° C. for 16 hours. The resulting slurry of crystalline D-(−)-2-(3'-methoxy-4'-hydroxyphenyl)glycyl chloride hydrochloride is filtered to collect the product. The filter-cake is washed with dioxane and methylene chloride and then dried in a vacuum desiccator over P$_2$O$_5$ to yield about 7 g. of D-(−)-2-(3'-methoxy-4'-hydroxyphenyl)-glycyl chloride hydrochloride.

Preparation of D-(−)-2-amino-2-(4-acetoxyphenyl)acetyl chloride hydrochloride 83.6 g. (0.40 Mole) of D-(−)-2-amino-2-(4-acetoxyphenyl)acetic acid and 1.25 l of anhydrous methylene chloride are cooled to −5° C. with stirring. Then 152 g. of phosphorous pentachloride are slowly added followed by 4 ml. of dimethyl formamide. The mixture is stirred 4 hours at 0° C. The solid is collected, washed with anhydrous methylene chloride and vacuum dried at room temperature. Yield: 61 g. (57.5%). Anal. Total chlorine=27.2% (Theory 26.9%).

Preparation of D-mandelic acid carboxyanhydride

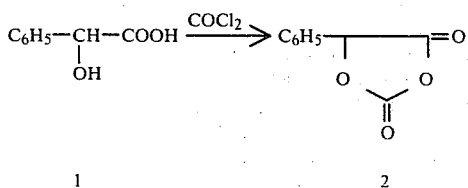

D-Mandelic acid carboxyanhydride (2)

Phosgene was bubbled through a solution of 2.0 g. (0.013 mole) of D(−)-mandelic acid (1) in dry tetrahydrofuran for 30 minutes. The solution was allowed to stand overnight after which time it was heated under reflux for 10 minutes. Evaporation of the solvent under reduced pressure afforded an oily residue which was solidified by trituration with n-hexane (20 ml.). The product was collected by filtration and dried in vacuo on KOH. Yield 2.3 g. of D-mandelic acid carboxyanhydride.

IR: $\nu_{max}^{nuj}$ 1895, 1875, 1780 cm$^{-1}$.

Among the most active compounds of the present invention are those having the D configuration at the α-carbon atom in the 7-side chain, that is, those made from D-2-phenylglycine or D-mandelic acid or a monosubstituted D-2-phenylglycine or D-mandelic acid as illustrated herein. In addition, the configuration at the two optically active, asymmetric centers in the β-lactam nucleus is that found in cephalosporin C produced by fermentation and in the 7-aminocephalosporanic acid derived therefrom.

The following examples are given in illustration of, but not in limitation of, the present invention. All temperatures are in degrees Centigrade. 7-Aminocephalosporanic acid is abbreviated as 7-ACA; -ACA- represents the moiety having the structure

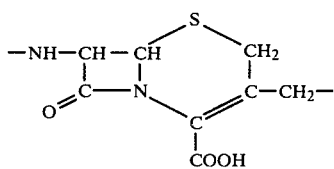

and thus 7-ACA can be represented as

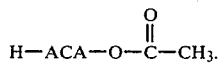

Methyl isobutyl ketone is represented as MIBK. "Skellysolve B" is a petroleum ether fraction of B.P. 60°–68° C. consisting essentially of n-hexane.

LA-1 resin is a mixture of secondary amines wherein each secondary amine has the formula

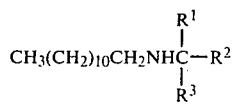

wherein each of R$^1$, R$^2$ and R$^3$ is a monovalent aliphatic hydrocarbon radical and wherein R$^1$, R$^2$ and R$^3$ contain in the aggregate from eleven to fourteen carbon atoms. This particular mixture of secondary amines, which is sometimes referred to in these examples as "Liquid Amine Mixture No. II," is a clear amber liquid having the following physical characteristics: viscosity at 25° C. of 70 cpd., specific gravity at 20° C. of 0.826; refractive index at 25° C. of 1.4554; distillation range at 10 mm., up to 170° C.−0.5%, 170°–220° C.−3%, 220°–230° C.−90% and above 230° C.−6.5%.

IR-120 is also called Amberlite IR-120 and is a strong cation exchange resin containing sulfonic acid radicals. Amberlite IR-120 is a commercially available cation exchange resin of the polystyrene sulfonic acid type; it is thus a nuclear sulfonated polystyrene resin cross-lined with divinyl benzene obtained by the procedure given by Kunin, Ion Exchange Resins, 2nd. Edition (1958), John Wiley and Sons, Inc. Therein see pages 84 and 87 for example.

DESCRIPTION OF THE PREFERRED EMBODIMENTS

Preparation of 1-Carboxyethyltetrazol-5-thiol

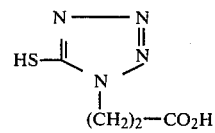

(A) 2-Carboethoxyethylisocyanate

β-alanine ethyl ester hydrochloride (93.6 g.), triethylamine (123.5 g) and methylene chloride (400 ml) were mixed together and cooled to −10° C. Carbon disulfide (46.5 g) dissolved in 150 ml. of chloroform was added to the above solution during a two-hour period while keeping the temperature at about −10° C. After the addition was complete, the temperature was allowed to warm to 10° C. for about 10 minutes. The solution was again cooled to −10° C. and 66.3 g of ethyl chloroformate in 60 ml of chloroform was added dropwise over a 40-minute period with stirring. The temperature was allowed to rise to room temperature for 30 minutes and again cooled to 0° C. an additional 61.6 of triethylamine was added to 0° C. and then the solution was stirred at room temperature for 3 hours.

The mixture was treated with water and the organic phase collected, washed with 2×250 ml of 2 N HCl, then 2×250 ml of NaHCO$_3$, then 2×250 ml of water. The organic phase was dried over Na$_2$SO$_4$ and the solvent removed in vacuo to produce 93.7 g of an oil found to be the desired product. The IR and NMR spectra were consistent with the structure.

(B) 1-Carboxyethyltetrazol-5-thiol

Sodium azide (29.7 g) was dissolved in 400 ml of water and heated to 60° C. in a nitrogen atmosphere. 2-Carboethoxyethylisocyanate (46.9 g) dissolved in 50 ml of Skellysolve B (essentially n-hexane) was added to the heated sodium azide solution. The solution was stirred for about 150 minutes at about 70°–72° C., then cooled to 30° C. in an ice bath. 50% sodium hyroxide solution was added until the pH was 12. The mixture was heated for forty minutes at 70° C. and cooled to 15° C. in an ice bath. The pH was adjusted to 2 using conc. Hcl and then extracted with ethyl acetate (4×150 ml). The ethyl acetate extracts were washed with water, then dried over sodium sulfate. The solvent was evaporated in vacuo and the product was collected as crystals from methylene chloride to yield 19.5 g of title product.

Preparation of 1-Carboxyalkyltetrazol-5-thiol

Substitution in the procedure for the preparation of 1-carboxyethyltetrazol-5-thiol for the β-alanine ethyl ester used therein of an equimolar quantity of an appropriately substituted amino acid ester of 4 to 10 carbon atoms produces the corresponding 1-Carboxy ($C_1$–$C_9$ alkyl)tetrazol-5-thiol; e.g.,
1-Carboxypropyltetrazol-5-thiol,
1-Carboxybutyltetrazol-5-thiol,
1-Carboxypentyltetrazol-5-thiol,
1-Carboxyhexyltetrazol-5-thiol,
1-Carboxyheptyltetrazol-5-thiol,
1-Carboxyoctyltetrazol-5-thiol, and
1-Carboxynonyltetrazol-5-thiol.

Preparation of 7-amino-7-methoxy-3-(1-carboxymethyltetrazol-5-ylthiomethyl)-3-cephem-4-carboxylic acid In general, the procedure described in U.S. Pat. No. 3,875,146 for the preparation of 7-methoxy substituted-7-aminocephalosporanic acids is followed to produce the starting material for the title compound.

9. Air dry the solid to constant weight. This product may vary in color from yellow to dark brown.

10. Pass the product through a 200 mesh stainless steel screen.

11. Suspend 10 grams of the 200 mesh powder in 200 ml. of n-propanol with rapid stirring.

12. Add 2.0 ml. of concentrated hydrochloric acid and stir vigorously for 0.5 hour at room temperature.

13. Filter the slurry. Wash the brown solids with 20 ml. of n-propanol and add the wash to the filtrate (save the filter cake for possible recovery of additional product).

14. Add 1.5 grams of charcoal ("Darco G-60") to the n-propanol filtrate of step 13. Slurry for 0.5 hour. Remove the carbon by filtration. Wash the carbon with 20 ml. of n-propanol and add the wash to the filtrate.

15. With rapid stirring, add triethylamine to the n-propanol filtrate to an apparent pH of 3.0. Crystals form. Slurry for 10 minutes 16. Collect the white crystals by filtration and wash with 30 ml. of n-propanol, 50 ml. of methanol, and vacuum dry at 40° C. for 24 hours.

Method II

Method I.

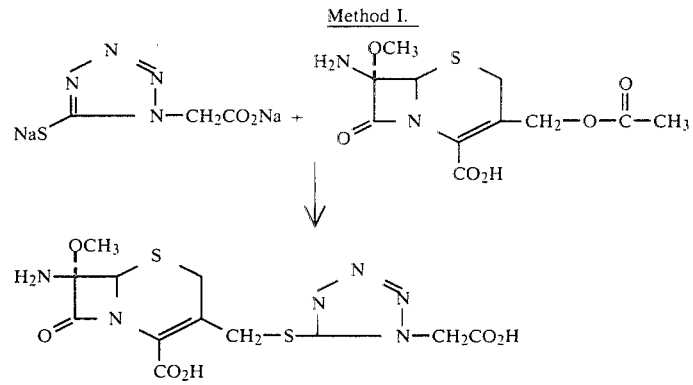

1. Into a 3 necked flask set up with an agitator, a temperature regulator, thermometer and a nitrogen inlet tube, place 18 grams (0.066 mole) of 7-amino-7-methoxycephalosporanic acid, and 300 ml. of 0.1 M pH 6.4 phosphate buffer (20.7 grams of sodium phosphate, monobasic $0.1H_2O$ + 8.5 grams of sodium phosphate, dibasic, anhydrous, q.s. to 2 liters).

2. With agitation of the mixture described in step 1, add 1.5 grams of sodium bisulfite and 16 grams (0.078 moles) of 1-carboxymethyl-5-mercaptotetrazole disodium.

3. With agitation continuing, bubble nitrogen through the mixture for 10 minutes.

4. Maintaining agitation and nitrogen inflow, heat the slurry over a 20 minute period to 56° C. During this time interval, 6.5 grams of sodium bicarbonate is added in small increments.

5. With continued agitation and nitrogen inflow, maintain the temperature of the solution at 56° C. for 4 hours. The pH should remain at between 6.2–6.6.

6. Cool the reaction mixture in an ice bath to 5° C.

7. Add 50 ml. of a 1:1 phosphoric acid/water solution to the mixture or concentrated HCl to a pH of 2.0–3.0.

8. Collect the product by filtration. Wash the filter cake with 20 ml. of cold water followed by 200 ml. of cold methanol.

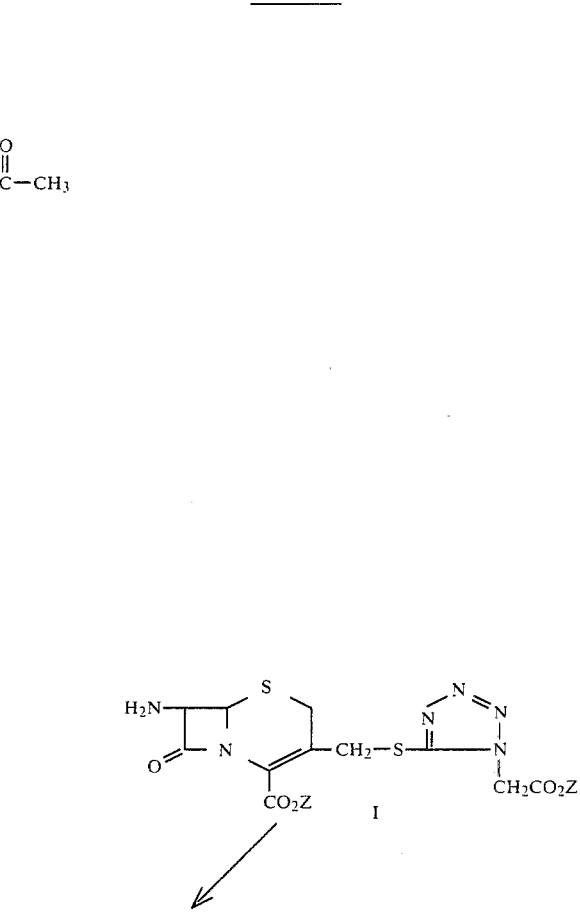

-continued
Method II

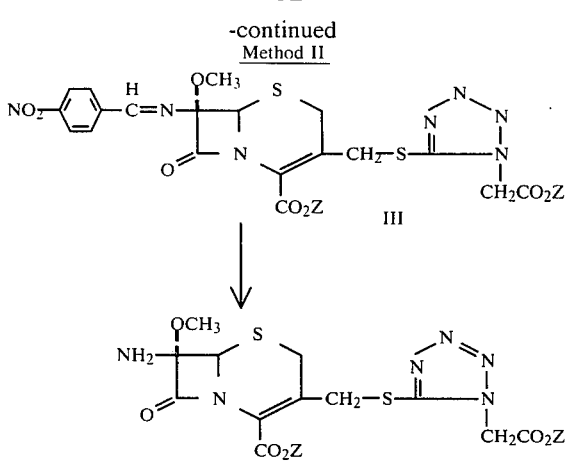

in which Z is benzhydryl ester.

(A) 7-amino-3-(1-Carboxymethyltetrazol-5-ylthiomethyl)-3-cephem-4-carboxylic acid is dissolved in dioxane in the presence of a catalytic amount of p-toluenesulfonic acid. Methanol is added and the solutions are taken to dryness in vacuo several times, following which additional anhydrous dioxane is added. Diphenyldiazomethane is added in a ratio of 2 moles of drayomethane per mole of cephalosporin. The solvents are removed in vacuo to produce 7-amino-3-(1-carboxymethyltetrazol-5-ylthiomethyl)-3-cephem-4-carboxylic acid dibenzhydryl ester (I).

(B) The dibenzhydryl ester obtained in step A supra is dissolved in methylene chloride and p-nitrobenzaldehyde is added in about a 1:1 molar ratio of aldehyde to cephalosporin. A small amount of anhydrous magnesium sulfate is added and the mixture is stirred for 0.5 hours at ambient temperatures to produce 7-(p-Nitrobenzylideneamino)-3-(1-carboxymethyltetrazol-5-yl-thiomethyl)-3-cephem-4-carboxylic acid dibenzhydryl ester (II).

(C) Compound II obtained in Step B is dissolved in dry tetrahydrofuran and the solution is cooled to −78° C. under a N₂ atmosphere. An amount of phenyl lithium, equimolar in quantity to the amount of cephalosporin is added at −78° C. The temperature is allowed to rise to −50° C. and an amount of freshly prepared o-methyl-dimethyl sulfoxonium methosulfate [(CH₃)₂S⊕OCH₃O⊖SO₂CH₃], in 1:1 DMSO:hexamethylphosphoramide is added. The methoxylation reaction mixture is stirred for 10 minutes at −50° C. and then allowed to warm to room temperature to produce the product, 7-Methoxy-7-(p-Nitrobenzylideneamino)-3-(1-carboxymethyltetrazol-5-yl-thiomethyl)-3-cephem-4-carboxylic acid dibenzhydryl ester (III).

(D) Compound III obtained in Step C is hydrolyzed by treating the compound with an equimolar amount of aniline hydrochloride in methanol, at room temperature for 1 to 24 hours.

Preparation of
7-amino-7-methoxy-3-(1-carboxyalkyltetrazol-5-ylthiomethyl)-3-cephem-4-carboxylic acid Substitution in the procedure above of the appropriate thiol, e.g.,
1-carboxypropyl-5-mercaptotetrazole disodium,
1-carboxybutyl-5-mercaptotetrazole disodium,
1-carboxypentyl-5-mercaptotetrazole disodium,
1-carboxyhexyl-5-mercaptotetrazole disodium,
1-carboxyheptyl-5-mercaptotetrazole disodium,
1-carboxyoctyl-5-merceptotetrazole disodium and
1-carboxynonyl-5-mercaptotetrazole disodium
produces the corresponding 7-amino-7-methoxy-3-(1-carboxyalkyltetrazol-5-ylthiomethyl)-3-cephem-4-carboxylic acid.

Preparation of 3-aminomethyl-2-thiophene acetic acid

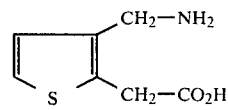

(A) Thiophene-3-carboxaldehyde dimethyl acetal (2a)

A mixture of thiophene-3-carboxaldehyde[1] (322 g., 1.9 moles), trimethoxymethane (636 g., 6 moles) and IR-120 resin (H⁺, 6 g) in methanol (200 ml) was refluxed over a period of 4 hours. The resin was removed and the filtrate was evaporated under reduced pressure to give a colorless oil which was distilled under reduced pressure. Yield 423 g (94%); B.p. 90°–95° C. 13 mmHg.
[1]S. Gronowitz, Arkev, kemi., 8, 411 (1955)

IR: $\nu_{max}^{liq}$ 3150, 1045, 1025 cm⁻¹.

NMR: $\nu_{ppm}^{neat}$ 3.21 (6H, s, OCH₃),

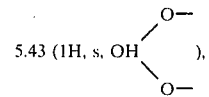

7.0–7.4 (3H, m, thiophene-H)

(B) 2-Formylthiophene-3-carboxaldehyde dimethylacetal (3a)

To a stirred solution of 2a (423 g, 2.68 moles) in anhydrous ether (1 L) was added dropwise in 1 hr. a freshly prepared solution of n-butyllithium (27 moles) in ether keeping a gentle reflux under dry N₂. Reflux being continued for 0.5 hr., a solution of DMF (dimetylformamide) (432 g., 6 moles) in anhydrous ether (0.8 L) was added dropwise to the mixture over a period of 0.75 hr. with vigorous stirring. After the complete addition, the mixture was stirred overnight, poured onto crushed ice (1 Kg) with stirring and allowed to raise to room temperature. The organic layer was separated, and the washed layer was saturated with NaCl and extracted thoroughly with ether (2×200 ml). The ether extracts were combined, dried over MgSO₄, and concentrated. The residue was distilled under reduced pressure and the pale yellow oil was collected at 100°–125° C., 0.7 mmHg. Yellow 277 g (56%).

IR: $\nu_{max}^{liq}$ 3110, 1660, 1100 cm⁻¹.

NMR: $\delta_{ppm}^{neat}$ 3.40 (6H, s, OCH₃),

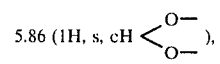

7.27 (1H, d, J=6 Hz, thiophene-H3), 7.81 (1H, d-d, J=6 Hz, thiophene-Hz), 10.34 (1H, d, J=1, 5 Hz, —CHO).

(C) 1-methylsulfinyl-1-methylthio-2-(3-carboxaldehyde ethylene (4b)

Preparation of 4b was carried out according to the procedure similar to that reported by K. Ogura et al[4]. Triton B (40% in methanol, 2 ml) in THF (tetrahydrofuran) (5 ml) was added to a solution of methyl methylthiomethyl sulfoxide[2] (2.5 g, 20 m moles) and 2-formyl-3-thiophenecarboxaldehyde ethylene acetal[3] (3b). The mixture was refluxed for about one hour and concentrated under reduced pressure. The residue was dissolved in benzene (150 ml) and extracted with water (3×20 ml). The organic layer was dried over MgSO$_4$ and evaporated to dryness under reduced pressure. The residue was dissolved in benzene (150 ml) and extracted with water (3×20 ml). The organic layer was dried over MgSO$_4$ and evaporated to dryness under reduced pressure. The residue was column-chromatographed on silica gel (80 g) eluting with benzene (500 ml) and chloroform (100 ml) successively. From the chloroform eluate 4.9 g (85%) of the product 4b was isolated as a pale yellow oil.

[2] K. Ogura, et al., Bull. Chem. Soc. (Japan), 45, 2203 ('72)
[3] D. W. McDowell et al., J. Org. Chem. 31, 3592 ('66)
[4] K. Ogura, et al., Tetrahedron Letters, 1383 (1972).

Ir: $\nu_{max}^{liq}$ 3110, 1600 cm$^{-1}$.

Nmr: $\delta_{ppm}^{CDCl_3}$ 2.42 (3H, x, S-CH$_3$), 2.78 (3H, s, SO-CH$_3$), 4.15 (4H, m, C$_2$CH$_2$-),

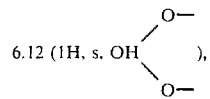

6.12 (1H, s, OH)

7.34 (1H, d, J=4.5Hz, thiophene-H$\beta$), 7.40 (1H, d, J=4.5Hz, thiophene-H$\alpha$), 8.28 (1H, s, —CH=).

The semicarbazone of 4 was prepared by a usual manner and crystallized from ethanol-DMF. M.p. 212°-213° C.

Anal. Calcd. for C$_{10}$H$_{13}$N$_3$O$_2$S$_2$: C, 39.58; H, 4.32; N, 13.85; S, 31.70. Found: C, 39.46; H, 4.24; N, 14.05; S, 31.63.

(D) 1-Methylsulfinyl-1-methylthio-2-(3-carboxaldehyde dimethylacetal-2-thienyl)ethylene (4a)

The compound 4a was prepared by the procedure similar to that for 4b. Triton B (40% in methanol, 50 ml) was added to a solution of methyl methylthiomethylsulfoxide (72 g., 0.58 mole) and 3a (108 g, 0.58 mole) in THF (300 ml) and the mixture was refluxed for 4 hours. Separation by column chromatography with silica gel (400 g) eluting with chloroform (5 L) gave 130.5 g (78%) of 4a as a pale yellow oil.

IR: $\nu_{max}^{liq}$ 3100, 1580, 1100, 1050$^{-1}$.

NMR: $\delta_{ppm}^{CCl_4}$ 2.42 (3H, s, S—CH$_3$), 2.70 (3H, s, SO—CH$_3$), 3.34 (6H, s, OCH$_3$),

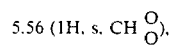

5.56 (1H, s, CH O/O), 7.20 (1H, d, J=6 Hz, thiophene-H$\beta$), 7.40 (1H, d, J=6 Hz, thiophene-H$\alpha$), 8.12 (1H, s, —CH=).

(E) Ethyl 3-formyl-2-thienylacetate[4] (5)

Dry hydrogen chloride (33 g) was absorbed in anhydrous ethanol (500 ml). To this solution 4a (130 g, 0.45 mole) was added and the mixture heated under reflux for 5 mins. The reaction mixture was diluted with water and evaporated under reduced pressure. The residue was extracted with benzene (2×100 ml) and the benzene extracts were combined, washed with water (50 ml), dried over MgSO$_4$ and evaporated to dryness. The oily residue was column-chromatographed on silica gel (400 g) eluting with chloroform (5 L). Fractions containing the desired product were combined and concentrated. The residual oil (60 g) was distilled under reduced pressure to afford 23 g (23%) of 5, boiling at 120°-126° C./1 mmHg.

IR: $\nu_{max}^{liq}$ 3110, 1730, 1670 cm$^{-1}$.

NMR: $\delta_{ppm}^{CDCl_3}$ 1.30 (3H, t, J=6 Hz, —CH$_2$CH$_3$), 4.25 (2H, q, J=6 Hz, —CH$_2$CH$_3$), 4.26 (2H, s, —CH$_2$CO), 7.25 (1H, d, J=5 Hz, thiophene-H$\beta$(, 7.48 (1H, d, J=5 Hz, thiophene-H$\alpha$), 10.15 (1H, s, CHO).

The analytical sample of 5 was submitted as the 2,4-dinitrophenylhydrazone which was crystallized from chloroform. M.p. 178°-179° C.

IR: $\nu_{max}^{nujol}$ 1720, 1610, 1570 cm$^{-1}$.

Anal. Calcd. for C$_{15}$H$_{14}$N$_4$O$_6$S: C, 47.62; H, 3.73; N, 14.81; S, 8.47. Found: C, 47.33; H, 3.47; N, 14.77; S, 8.68.

According to the similar procedure 2.2 g (7.6 m moles) of the ethylene acetal 4b was treated with 1.1 g of dry hydrogen chloride in 800 ml of anhydrous ethanol to afford 5 which was purified by column chromatography on silica gel (30 g). Elution with chloroform gave 663 mg (44%) of 5 as a pale yellow oil.

(F) Ethyl 3-formyl-2-thienylacetate oxime (6)

Sodium carbonate (1.7 g, 16 m mole) was added to a solution of the aldehyde 5, (3.14 g, 16 m mole) and hydroxylamine hydrochloride (2.2 g, 32 m mole) in 50% aq. ethanol (40 ml) at 5° C. with stirring. The reaction mixture was warmed up to room temperature. After 2.5 hrs., the reaction mixture was concentrated under reduced pressure. The residue was extracted with benzene (3×50 ml). The benzene extracts were washed with water (10 ml), dried over MgSO$_4$, and evaporated under reduced pressure. Separation by column chromatography on silica gel (60 g) gave 2.7 g (80%) of colorless oil 6.

IR: $\nu_{max}^{liq}$ 3400, 1730, 1620 cm$^{-1}$.

NMR: $\delta_{ppm}^{Aceton-d6}$ 1.23 (3H, t, J=7.5 Hz, —CH$_2$C$_3$), 4.01 (2H, s, —CH$_2$CO), 4.14 (2H, q, J=7.5 Hz, —OH$_2$CH$_3$), 7.31 (2H, s, thiophene-H), 8.26 (1H, s, —CH=N), 10.15 (1H, s, NOH, disappeared by addition of D$_2$O).

(G) The $\delta$-lactam of 3-aminomethyl-2-thienylacetic acid (7)

Method A: Catalytic reduction

A mixture of the oxime 6 (2.65 g, 12.5 m moles), 10% palladium on charcoal, dry hydrogen chloride (1.4 g, 37.2 m moles) in anhydrous ethanol (68 ml) was hydrogenated overnight under atmospheric pressure at room temperature. The catalyst was exchanged twice and the reaction was carried out over a period of 3 days. The catalyst was removed and the filtrate was concentrated under reduced pressure. To the residue was added water (10 ml) and the mixture washed with ethyl acetate (2×10 ml). The aqueous layer was adjusted to pH 9 with sodium carbonate, saturated with sodium chloride, and extracted with ethyl acetate (3×20 ml). The ethyl acetate extracts were dried over MgSO$_4$, treated with charcoal, and evaporated under reduced pressure. Recrystallization from ethyl acetate gave 417 mg (22%) of colorless needless 7 melting at 194°-195° C.

IR: $\nu_{max}^{KBr}$ 3200, 1650, 1480 cm$^{-1}$.

NMR: $\delta_{ppm}^{DMSO-d6}$ 3.53 (2H, t, J=3 Hz, —CH$_2$CO—), 4.36 (2H, d-t, J=3, 1.5 Hz, changed to a triplet by addition of D$_2$O, J=3 Hz, CH$_2$N), 6.95 (1H, d, J=4.5 Hz, thiophene-H$\beta$), 7.45 (1H, d, J=4.5 Hz, thiophene-Hα), 8.0 (1H, m, disappeared by addition of D₂O, NH).

Anal. Calcd. for C₇H₇NOS: C, 54.88; H, 4.61; N, 9.14; S, 20.93. Found: C, 55.04; H, 4.45; N, 9.13; S, 20.50.

Method B: Zn-dust reduction

To a solution of the oxime 6 (18.3 g, 86 m moles) in acetic acid (200 ml), zinc dust (17 g, 258 m moles) was added portionwise over a period of 1 hr. at 40°–50° C. with vigorous stirring. The reaction mixture was stirred overnight at room temperature and heated at 60° C. for 4 hours. The contents were filtered and the filtrate was concentrated under reduced pressure. To the residual oil was added water (100 ml) and the mixture washed with ether (2×50 ml). The aqueous solution was layered with ethyl acetate (100 ml) and adjusted to pH 10 with sodium carbonate. The precipitate was filtered off. The filtrate was extracted with ethyl acetate. The ethyl acetate extracts were washed with water (10 ml), dried over MgSO₄, and evaporated under reduced pressure. The residual solid was triturated with benzene. Crystallization from ethyl acetate gave 2.7 g (21%) of the lactam 7 which was identical to Method A in the IR and the NMR spectra.

H. 3-Aminomethyl-2-thienylacetic acid (8)

A mixture of the lactam 7 (2.88 g, 18.8 m moles) and 6b hydrochloric acid (50 ml) was heated under reflux for 3 hrs. The reaction mixture was concentrated under reduced pressure. To the residue was added water (20 ml) and the mixture treated with charcoal and evaporated under reduced pressure. The trituration of the residue with THF gave the amino acid 8 hydrochloride (3.72 g, 95%; m.p. 171°–172° C.; ir (KBr) cm⁻¹: 3450, 3000, 1700, 1200; nmr (D₂O)ppm: 4.80 (2H, s, —CH₂CO), 4.27 (2H, s, CH₂—N), 7.26 (1H, d, J=6 Hz, thiophene-Hβ), 7.53 (1H, d, J=6 Hz, thiophene-Hα). The hydrochloride (3.71 g, 17.9 m moles) was dissolved in water (10 ml) chromatographed on a column of IR-120 (H, 30 ml) and developed successively with water (100 ml) and 5N-NH₄OH (2 L). The ammonia eluate was evaporated to dryness. The residue was crystallized from aqueous acetone to give 3.0 g (98%) of 8, m.p. 223°–225° C.

IR: $\nu_{max}^{HBr}$ 3000, 1620, 1520 cm⁻¹.

NMR: $\delta_{ppm}^{D_2O-Na_2CO_3}$ 3.20 (sH, s,—CH₂OC), 4.13 (2H, s, CH₂N), 7.04 (1H, d, J=6 Hz, thiophene-Hβ), 7.30 (1H, d, J-6 Hz, thiophene-Hα).

Anal. Calcd. for C₇H₉NO₂S: C, 49.10; H, 5.30; N, 8:18; S, 18.73. Found: C, 48.53: h, 5.22; N, 7.98; S,18.97.

I. 3-t-Butoxycarbonylaminomethyl-2-thienylacetic acid (9)

A mixture of 3-aminomethyl-2-thienylacetic acid 8 (3.1 g, 18 m moles) and triethylamine (8 g, 80 m moles) in 50% aqueous acetone (80 ml) was added dropwise t-butoxycarbonyl azide (5.7 g, 40 m moles) over a period of 20 mins. at 0° C. with vigorous stirring. The reaction mixture was stirred overnight at room temperature and concentrated under reduced pressure. The concentrate was washed with ether (2×20 ml), adjusted to pH 2 with conc. HCl and extracted with ethyl acetate (2×50 ml). The ethyl acetate extracts were washed with saturated aqueous sodium chloride, dried over MgSO₄, treated with charcoal and evaporated under reduced pressure. The residue was triturated with n-hexane and crystallized from n-hexane and benzene to give 4.5 g (92%) of colorless needles 9, melting at 62°–63° C.

IR: $\nu_{max}^{nujol}$ 3350, 1700 cm⁻¹.

NMR: $\delta_{ppm}^{CDCl_3}$ 1.43 (9H, s, BOC-H), 3.27 (2H, s, CH₂CO), 4.16 (2H, d, J=6 Hz, CH₂-N, a singlet when D₂O was added, 5.00 (1H, br, —NH—, disappeared by addition of D₂O), 6.30 (1H, broad s, —COOH, disappeared by addition of D₂O), 6.86 (1H, d, J=6 Hz, thiophene-Hβ), 7.06 (1H, d, J=6 Hz, thiophene-Hα).

Anal. Calcd. for C₁₂H₁₇NO₄S: C, 52.89; H, 6.29; N, 5.14; S, 11.77. Found: C, 53.30; H, 6.39; N, 5.13; S, 11.72.

J. Alternate Synthesis of 1-Carboxymethyl-5-mercaptotetrazole

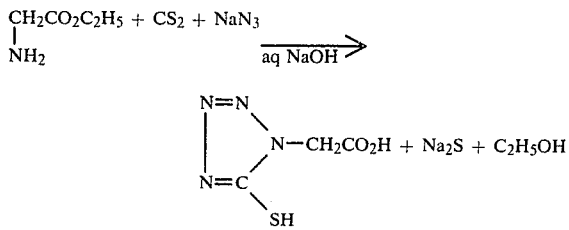

To a stirred mixture of 13.95 g (0.10 m) of glycine ethyl ester hydrochloride, 8.0 g (0.20 m) of sodium hydroxide and 8.37 g (0.11 m) of carbon disulfide was added a solution of 7.47 g (0.115 m) of sodium azide in 125 ml of water. The solution was heated at reflux for 6½ hrs. and stored 16 hrs. at 25°. The dark brown mixture was filtered and the filtrate acidified to pH 1.5 with conc. hydrochloric acid. The solution was carbon treated and the yellow filtrate was extracted 4×100 ml with ethyl acetate. The ethyl acetate was washed with water, dried over magnesium sulfate and evaporated at 40° (15 mm) to an oil. The oil was triturated with methylene chloride and the product was collected. The sample was dried in vacuo over phosphorus pentoxide for 16 hrs. at 25°. The IR and NMR spectra were consistent for the structure.

Reference: German Pat. No. 106645.

K. Preparation of 7β-(o-N-t-Butoxycarbonylaminomethyl-phenylacetamido)-7α-methoxycephalosporanic acid (1) Benzhydryl 7-(o-N-t-butoxycarbonylaminomethyl-phenylacetamide)cephalosporanate Mercuric oxide yellow (16.12 g., 74 mmol) was added to a mixture of benzophenone hydrazone (5.88 g. 30 mmol) and anhydrous sodium sulfate (8 g) in dry ether (100 ml). To the stirred mixture was added KOH-saturated ethanol (1.5 ml) and stirring was continued for 1.5 hrs. at room temperature. The mixture was filtered and the filtrate was added to a solution of 7-(o-N-t-butoxycarbonylaminomethylphenylacetamido)cephalosporanic acid (10.38 g., 20 mmol) in THF (60 ml). The reaction mixture was stirred for 3 hrs. at room temperature and evaporated under reduced pressure. The residue was triturated with n-hexane (200 ml) and collected by filtration. The crude product was dissolved in hot benzene (100 ml) and treated with a small amount of carbon. The filtrate was diluted with ether (500 ml) and kept to stand in a refrigerator overnight to afford the title product as a colorless crystalline solid. Yield 12.25 g (89%); m.p. 150°–153° C.

IR: $\nu_{max}^{KBr}$ 3340, 3300, 1785, 1740, 1720, 1680, 1540, 1230, 1170 cm$^{-1}$.

UV: $\lambda_{max}^{EtOH}$ 263 nm ($\epsilon$ 8580). $[\alpha]_D^{26}$: +5°, (c=1.0, chloroform).

NMR: $\delta_{ppm}^{CDCl_3}$ 1.45 (9H, s, t-Bu-$\underline{H}$), 2.02 (3H, s, OAc), 3.39 (2$\underline{H}$, m 2-H), 3.68 (2H, s, CH$_2$CO), 4.32 (2H, d, 4 Hz, CH$_2$N, a singlet by addition of D$_2$O), 4.72 (1H, d, 14 Hz, 3-$\underline{H}$), 4.93 (1H, d, 4 Hz, 6-$\underline{H}$), 5.05 (1H, d, 14 Hz, 3-$\underline{H}$), 5.35 (1H, br, CH$_2$N$\underline{H}$, disappeared by addition of D$_2$O), 5.86 (1H, d-d, 4 & 8 Hz, 7-$\underline{H}$, a doublet with J=4 Hz by addition of D$_2$O), 6.95 (1H, s, Ph$_2$C$\underline{H}$), 7.2–7.6 (14H, m, phenyl-$\underline{H}$).

Anal. Calc'd. for C$_{37}$H$_{39}$N$_3$O$_8$S: C, 64.80; H, 5.73; N, 6.13; S, 4.68. Found: C, 64.70, 64.65; H, 5.95, 5.70; N, 6.12, 6.00; S, 4.82, 4.68.

(2) Benzhydryl 7β-(o-N-t-butoxycarbonylaminomethyl-phenylacetamido)-7α-methoxycephalosporanic A chilled solution (−65° C.) of the compound from step 1 (3050 mg, 4.45 mmol) in dry THF (20 ml) was poured in one portion into a solution of lithium (108 mg. 15.6 mmol) in methanol-THF (12 ml:20 ml) which was chilled at −65° C. in dry ice-acetone bath. After one minute t-butylhypochlorite (529 mg., 0.58 ml. 4.9 mmol) was added to the mixture and stirred for 15 mins. at the same temperature. Acetic acid (1 ml) was added to the mixture to quench the reaction. The mixture was poured into water (200 ml) and extracted with ethyl acetate (4×50 ml). The combined extracts were washed with water and evaporated under reduced pressure. The residue was dissolved in hot benzene (20 ml) and treated with a small amount of carbon. The filtrate was diluted with ether (200 ml) and kept in a refrigerator to give the title compound as a crystalline product. Yield 2094 mg (66%); mp 171°–173° C. Recrystallized from benzene-ether, mp 174°–175° C.

IR: $\nu_{max}^{KBr}$ 3350, 3250, 1785, 1750, 1735, 1680, 1525, 1230, 1170, 1080 cm$^{-1}$.

UV: $\lambda_{max}^{EtOH}$ 247 nm (λ 6790), 267, nm (λ 7070).

$[\alpha]_D^{22}$: +98° (c=0.5, chloroform).

NMR: $\delta_{ppm}^{CDCl_3}$ 1.43 (9H, s, t-Bu-H), 2.00 (3H, s, OAc), 3.2–3.4 (2H, m, 2-H), 3.49 (3H, s, OMe), 3.72 (2H, s, CH$_2$DO), 4.34 (2H, d, 6 Hz, a singlet by addition of D$_2$O, CH$_2$N), 4.74 (1H, d, 14 Hz, 3-H), 5.04 (1H, s, 6-H), 5.10 (1H, d, 14 Hz, 3-H), 6.93 (1H, x, CHPh$_2$), 7.2–7.5 (14H, m, phenyl-H).

Anal. calc'd. for C$_{38}$H$_{41}$N$_3$O$_9$S: C, 63.76; H, 5.77; N, 5.87; S, 4.38. Found: C, 63.62, 63.67; H, 5.83, 5.65; N, 5.87, 5.73; S, 4.89, 4.72.

(3) 7β-(o-Aminomethylphenylacetamido)-7α-methoxycephalosporanic acid

A mixture of the product from step 2 (4.60 g., 6.43 mmol) and TFA (8 ml) was stirred for 20 minutes to 0° to 20° C. to afford a viscous solution, which was diluted with ether (100 ml) to precipitate the TFA salt of the title product which was collected by filtration and dissolved in acetonitrile (200 ml). The solution was treated with a small amount of carbon. A mixture of conc. NH$_4$OH-acetonitrile (1:1) was added dropwise into the filtrate with stirring until no more precipitation occurred. The title product was collected by filtration, washed with acetonitrile (50 ml) and dried. Yield 2.49 g (86%): m.p. 161°–165° C. (dec.).

IR: $\nu_{max}^{KBr}$ 3600–2400, 1770, 1740(sh), 1665, 1600, 1230, 1135 cm$^{-1}$.

UV: $\lambda_{max}^{1\%NaHCO_3}$ 237 nm (λ 6300), 265 nm (λ 7700).

NMR: $\delta_{ppm}^{D_2O+NaHCO_3}$ 2.10 (3H, s, OAc), 3.15 (1H, d, 18 Hz, 2-$\underline{H}$), 3.53 (3H, s, OCH$_3$) 3.62 (1H, d, 18 Hz, 2-$\underline{H}$), 3.90 (2$\underline{H}$, s, CH$_2$N), 5.12 (1H, s, 6-$\underline{H}$), 7.45 (4H, s, phenyl-$\underline{H}$).

Anal. calc'd. for C$_{20}$H$_{23}$N$_3$O$_7$S.2H$_2$O: C, 49.48; H, 5.61; N, 8.65; S, 6.60. Found: C, 49.64, 49.38; H, 4.93, 4.86; N, 8.86, 8.92; S, 6.57.

(4) 7β-(o-N-t-Butoxycarbonylaminomethyl-phenylacetamido)-7α-methoxycephalosporanic acid A mixture of the product from step 3 (800 mg, 1.8 mmol), t-butyl 3,6-dimethylpryimidin-2-ylthiocarbonate (864 mg., 3.7 mmol) and triethylamine (273 mg., 0.38 ml., 2.7 mmol) in 50% aqueous THF (12 ml) was stirred for 4 hrs. at room temperature. The mixture was diluted with ethyl acetate (100 ml) and washed several times with 10-ml portions of 6 N HCl until the yellow color of the aqueous layer disappeared. The organic layer was washed with water and dried. Evaporation of the solvent under reduced pressure gave the title product which was collected by filtration, washed with n-hexane and dried. Yield 568 mg (57%): mp 102°–106° C. (dec.).

IR: $\nu_{max}^{KBr}$ 3300, 1780, 1720, 1700, 1515, 1230, 1165 cm$^{-1}$.

UV: $\lambda_{max}^{EtOH}$ 244 nm ($\epsilon$ 6630), 266 nm ($\epsilon$ 7150).

NMR: $_{ppm}^{CDCl_3}$ 1.48 (9H, s, t-Bu-$\underline{H}$), 2.08 (3H, s, COCH$_3$), 3.3–3.4 (2H, m, 2-$\underline{H}$), 3.48 (3H, s, OCH$_3$), 3.78 (2H, s, C$\underline{H}_2$CO$_2$), 4.30 (2H, d, 6 Hz, a singlet by addition of D$_2$O), 4.82 (1H, d, 15 Hz, 3-$\underline{H}$), 5.08 (1H, s, 6-$\underline{H}$), 5.12 (1H, d, 15 Hz, 3-$\underline{H}$), 7.26 (4H, s, phenyl-$\underline{H}$), 8.20 (1H, br, disappeared by addition of D$_2$O, NH or COOH), 8.85 (1H, br-s, disappeared by addition of D$_2$O).

Anal. calc'd. for C$_{25}$H$_{31}$N$_3$O$_9$S: C, 54.63; H, 5.69; N, 7.65; S, 5.84. Found: C, 54.33, 54.42; H, 5.73, 5.59; N, 7.44, 7.39; S, 6.01, 5.97.

EXAMPLE 1

7-(2-Aminomethylphenylacetamido)-3-(1-carboxymethyltetrazol-5-ylthiomethyl)-3-cephem-4-carboxylic acid

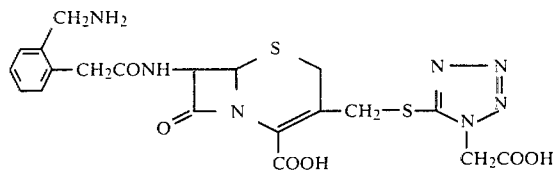

1. Into a 3 necked flask containing 100 ml. of deionized water and set up with an agitator and thermometer, add 7.6 grams (0.021 mole) of 7-amino-3-(1-carboxymethyltetrazol-5-ylthiomethyl)-3-cephem-4carboxylic acid and 3.4 grams (0.034 mole) of N-methylmorpholine. Cool to 0° C. With agitation, the solution is maintained at 0° C. using an ice bath.

2. In a separate flask set up with an agitator, add 9.6 grams (0.03 mole) of sodium 2-(1-methoxycarbonyl-1-propen-2-ylaminomethyl)phenylacetate and 184 ml. of tetrahydrofuran. With agitation, the suspension is cooled to −30° C., using a dry ice acetone bath. Maintaining agitation and temperature at −30° C., add 20 drops of dimethylbenzylamine and 4.4 grams (0.03 mole) of isobutyl chloroformate. Stir the resulting mixture for 5 minutes.

3. Add all of the mixture from step 2 to the agitation solution in step 1 at one time. The resulting solution is maintained at 3° C. with agitation for 1 hour.

4. Evaporate the tetrahydrofuran from the reaction mixture at 30° C. using vacuum (15 mm).

5. Adjust the pH of the remaining aqueous solution to 4.0 using concentrated hydrochloric acid.

6. Add 2.5 grams of charcoal ("Darco G-60") to the solution and mix for 20 minutes. Remove the carbon by filtration.

7. The filtrate is layered with 120 ml. of ethyl acetate and with agitation the pH is lowered to 3.8 with concentrated hydrochloric acid. Some light tan colored solids may separate and are removed by filtration. (Save for reworking and recovery).

8. Using an ice bath, the filtrate is cooled to 5° C. and with agitation the pH is lowered to 2.5–2.8 with concentrated hydrochloric acid. Maintain the temperature at 5° C. and continue agitation for 1 hour.

9. Collect the product by filtration. Wash the filter cake with 5 ml. of cold deionized water followed by 5 ml. of cold methanol.

10. Air dry the solid 7-(2-aminomethylphenylacetamido)-3-carboxymethyltetrazol-5-ylthiomethyl)-3-cephem-4-carboxylic acid to constant weight. (A typical run produced 4.1 grams of product).

11. The product as obtained from step 10 is passed through a 200 mesh stainless steel screen.

12. Ten grams of this 200 mesh product is slurried in 100 ml. of chloroform. Five ml. of triethylamine is added and the mixture is heated to 50° C. with rapid stirring. The mixture is slurried at 50° C. for 5 minutes.

13. The mixture is filtered hot (7-ACA, 7-amino-3-(1-carboxymethyltetrazol-5-ylthiomethyl)-3-cephem-4-carboxylic acid, pigments and other impurities are soluble in the hot chloroform-triethylamine solution). The filter cake is washed with 25 ml. of chloroform and air dried for 2 hours. Yield: 1–8 grams of 7-(2-aminomethylphenylacetamido)-3-(1-carboxymethyltetrazol-5-ylthiomethyl)-3-cephem-4-carboxylic acid.

14. The product as obtained for step 13 is passed through a 200 mesh screen.

15. Ten grams of this 200 mesh product is slurried in 75 ml. of 0.1 N hydrochloric acid for 10–15 minutes. The mixture is filtered and the filter cake is washed with 25 ml. of water, 50 ml. of methanol, and air dried at room temperature for 2–3 hours. Yield: Up to 10 g. is obtained.

16. Ten grams of 7-(2-aminomethylphenylacetamido)-3-(1-carboxymethyltetrazol-5-ylthiomethyl)-3-cephem-4-carboxylic acid as obtained from step 15 is slurried in 65 ml. of methanol.

(a) Two ml. of concentrated hydrochloric acid is added. A solution or near solution is obtained. Stir for 5 minutes.

(b) One hundred and 30 ml. of water is rapidly added with vigorous stirring to the solution of (a) above. An instantaneous precipitate (containing most of the color) is obtained. (A pH of 1.3 to 1.6 is required.)

(c) The mixture is slurried for 1 minute and rapidly filtered. (Save solids for rework and recovery.)

(d) The filtrate is seeded and moderately stirred. The onset of crystallization is about 15–30 minutes.

(e) The mixture is stirred at ambient room temperature or at 4° C. for 2 hours after the onset of crystallization.

(f) The crystals are removed by filtration, washed with 25 ml. of 65% water, 35% methanol mixture (v/v), 50 ml. of methanol, and vacuum dried at 50° C. for 24 hours. Yield: Up to 9 grams of purified, white 7-(2-aminomethylphenylacetamido)-3-(1-carboxymethyltetrazol-5-ylthiomethyl)-3-cephem-4-carboxylic acid is obtained.

17. The following are two alternate procedures for the crystallization of 7-(2-aminomethylphenylacetamido)-3-(1-carboxymethyltetrazol-5-ylthiomethyl)-3-cephem-4-carboxylic acid.

(A)

1. Ten grams of product as obtained from step 15 is slurried in 100 ml. of methanol.

2. Two ml. of concentrated hydrochloric acid is added and a solution or near solution is obtained.

3. One and five tenths gram of charcoal ("Darco G-60") is added and the mixture is slurried for 0.5 hour.

4. The carbon is removed by filtration and washed with 20 ml. of methanol. The methanol wash is added to the filtrate.

5. One hundred and twenty ml. of water is added to the filtrate. (A small amount of precipitate may come out. This is removed by filtration and saved for rework-recovery.)

6. The solution of step 5 is rapidly stirred and adjusted to pH 2.5–3.0 with 10% sodium hydroxide. Crystals form.

7. The mixture is slurried for 0.5 hour. The crystals are removed by filtration, washed with 20 ml. of 50% methanol-water (v/v), 30 ml. of methanol and vacuum dried at 50° C. for 24 hours. Yield: Up to 9 grams of purified 7-(2-aminomethylphenylacetamido)-3-(1-carboxymethyltetrazol-5-ylthiomethyl)-3-cephem-4-carboxylic acid is obtained.

(B)

1. Ten grams of product as obtained from step 15 is slurried in 75 ml. of water.

2. Ten percent sodium hydroxide is added to a maintained pH of 6.8–7.2. A solution or partial solution may be obtained.

3. One and five tenths grams of charcoal ("Darco G-60") is added and the mixture is slurried for 0.5 hour at a maintained pH of 6.8–7.2 (continued addition of 0.1 to 1 N sodium hydroxide).

4. The carbon is removed by filtration. The carbon is washed with 20 ml. of water which is added to the filtrate.

5. The pH 6.8–7.2 solution of step 4 may be crystallized at pH 2.5–3.0 as described in steps 6 and 7 of A, above or at pH 1.2–1.5 (by addition of hydrochloric acid) and as described in d, e, and f of step 16. In both instances, up to 9 grams of crystalline 7-(2-aminomethylphenylacetamido)-3-(1-carboxymethyltetrazol-5-ylthiomethyl)-3-cephem-4-carboxylic acid is obtained. This product is frequently obtained as a crystalline monohydrate. When this compound was administered intramuscularly by injection at a dose of 10 mg/kg of body weight in mice, a blood level of 19.7 mg/ml was obtained at 15 minutes.

The protective dose in 50% of the animals challenged of title compound in mice against a lethal intramuscular dose of E. Coli A15119, K. Pneumoniae A9977 and E. cloacae A21020 was 0.39–0.42, 1.5–25 and 1–3.2 mg/kg. respectively.

EXAMPLE 2

Dipotassium 7-(D-α-hydroxyphenylacetamido)-3-(1-carboxymethyltetrazol-5-ylthiomethyl)-3-cephem-4-carboxylate

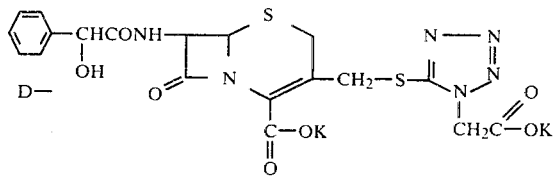

A. 7-(D-α-formyloxyphenylacetamido)-3-(1-carboxymethyltetrazol-5-yl-thiomethyl)-3-cephem-4-carboxylic acid To a suspension of 500 mg. (0.0134 mole) of 7-amino-3-(1-carboxymethyltetrazol-5-ylthiomethyl)-3-cephem-4-carboxylic acid in 10 ml. of water at 0° was added with stirring 200 mg. of sodium bicarbonate. As soon as the solution was complete 340 mg. (0.0172 mole) of D-(−)-2-formyloxy-2-phenylacetyl chloride was added all at once in 10 ml. of acetone. As soon as a precipitate formed, solid sodium bicarbonate was added and the solution was stirred at pH 8 for 1 hr. The acetone was evaporated at 15 mm at 30°, and the solution was layered with 20 ml. of ethyl acetate and acidified with 1:1 phosphoric acid. After extraction with ethyl acetate, the mixture was filtered and the organic layer was separated and evaporated to produce what was identified as substantially pure 7-(D-α-formyloxyphenylacetamido)-3-(1-carboxymethyltetrazol-5-yl-thiomethyl)-3-cephem-4-carboxylic acid.

B. Dipotassium 7-(D-α-hydroxyphenylacetamido)-3-(1-carboxymethyltetrazol-5-ylthiomethyl)-3-cephem-4-carboxylate The solid isolated in step A was dissolved in 5 ml. of methanol and 5 drops of conc. hydrochloric acid. The solution was treated with carbon and heated for 3 min. on the steambath. The mixture was filtered and diluted with 15 ml. of water. The gummy solid was triturated with cold water and finally with anhydrous ether. The solid was dissolved in 5 ml. of acetone and was treated with 50 mg. of potassium 2-ethylhexanoate. Dipotassium 7-(D-α-hydroxyphenylacetamido)-3-(1-carboxymethyltetrazol-5-ylthiomethyl)-3-cephem-4-carboxylate, as a white solid, was collected and weighed 90 mg. m.p. 175° slow decomp.

Anal. Calcd. for $C_{19}H_{16}K_2N_6O_7S_2$: C, 39.19; H, 2.77; N, 14.42. Found: C, 39.87; H, 3.50; N, 12.58.

When this compound was administered intramuscularly by injection at a dose of 10 mg/kg of body weight in mice, a blood level of 21.4 mg/ml was obtained at 15 minutes.

The protective dose in 50% of the animals challenged of title compound in mice against a lethal intramuscular dose of E. Coli A 15119, was 0.8 mg/kg.

EXAMPLE 3

7-(D-α-Aminophenylacetamido)-3-(1-carboxymethyltetrazol-5-ylthiomethyl)-3-cephem-4-carboxylic acid.

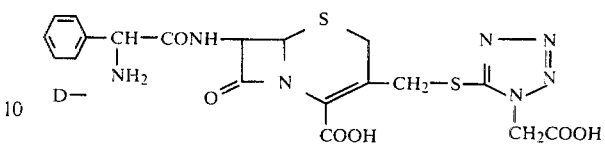

A solution of 0.55 g. (0.0022 mole) of D-(−)-α-tert.-butoxycarboxamidophenylacetic acid and 0.22 g. (0.0022 mole) of triethylamine (TEA) in 17 ml. of tetrahydrofuran (THF) at 0° was stirred vigorously with 0.300 g. (0.0022 mole) of isobutyl chloroformate. The mixture was stirred for 30 min. at 0° and a solution of 0.0022 mole of 7-amino-3-(1-carboxymethyltetrazol-5-ylthiomethyl)-3-cephem-4-carboxylic acid and 0.445 g. (0.0044 mole) of TEA in 6.8 ml. of 50% THF was added. The resulting solution was stirred for 2 hr. at 25° and then the THF evaporated at 40° at 15 mm to an oil. The oil was washed 2×50 ml. of ether, diluted in half with water and acidified to pH 3.0 with dilute hydrochloric acid. The mixture was stirred for 1 hr. in an ice-bath and the product was extracted into 75 ml. of ethyl acetate. The extract was washed with 2×20 ml. of water and 2×50 ml. of saturated sodium chloride solution. The ethyl acetate was evaporated at 35° at 15 mm. to an oil and triturated with Skellysolve B to yield 480 mg. (35.3%) of 7-(D-α-tert.-butoxycarboxamidophenylacetamido)-3-(1-carboxymethyltetrazol-5-ylthiomethyl)-3-cephem-4-carboxylic acid. This sample was added to 1 ml. of trifluoroacetic acid and the solution was stirred for 1 hr. at 0° and then diluted with 50 ml. of ether. The salt was collected, dissolved in 10 ml. of $H_2O$ and adjusted to pH 4.0 with dilute ammonium hydroxide ($NH_4OH$). The product was collected, washed with water and acetone and dried in vacuo over $P_2O_5$ for 18 hr. at 25° to yield 150 mg. (23.96%) of 7-(D-α-aminophenylacetamido)-3-(1-carboxymethyltetrazol-5-ylthiomethyl)-3-cephem-4-carboxylic acid; m.p. >180°, slow decomp. The IR and NMR spectra were consistent for the structure.

Anal Calcd. for $C_{19}H_{19}N_7O_6S_2 \cdot 1\frac{1}{2} H_2O$: C, 42.84; H, 4.16; N, 18.41. Found: C, 43.17; H, 4.12; N, 16.74.

EXAMPLE 4

7-(2-Aminomethyl-1,4-cyclohexadienylacetamido)-3-(1-carboxymethyltetrazol-5-ylthiomethyl)-3-cephem-4-carboxylic acid

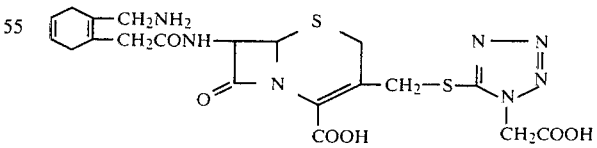

A solution of 0.80 g. (0.003 mole) of 2-t-butoxycarbonylaminomethyl-1,4-cyclohexadienylacetic acid and 0.303 g. (0.003 mole) of triethylamine in 19.2 ml. of THF was stirred at 0° and 0.41 g. (0.003 mole) of isobutyl chloroformate was added. The mixture was stirred for 30 min. at 0° and added to a solution of 0.003 mole of 7-amino-3-(1-carboxymethyltetrazol-5-ylthiomethyl)-3-cephem-4-carboxylic acid and 0.61 g. (0.006 mole) of TEA in 9.2 ml. of 50% THF. The resulting solution was stirred for 1½ hr. at 25°. The tetrahydrofuran was evaporated at 30° at 15 mm and the residue was washed 2×30 with ether and then diluted in half with water. The solution was acidified to pH 3.5 with dilute hydrochloric acid and the product was collected, dried for 18 hr. in vacuo over $P_2O_5$ at 25° to yield 1.55 g. (54.0%) of white powder. A total of 3.4 ml. of trifluoroacetic acid was added to the above 7-(α-(2-t-butoxycarbonylaminomethyl-1,4-cyclohexadienylacetamido)-3-(1-carboxymethyltetrazol-5-ylthiomethyl)-3-cephem-4-carboxylic acid and stirred for 1 hr. at 0°. The solution was diluted with 150 ml. ether and the precipitate was collected by filtration. The trifluoroacetate salt was suspended in 3.4 ml. of water and adjusted to pH 4.5 with dilute ammonium hydroxide. The gummy residue was triturated with water, collected and washed with water and acetone. The product was dried 18 hr. in vacuo over $P_2OhD_5$ at 25° to yield 53 mg. (15.72%) 7-(2-aminomethyl-1,4-cyclohexadienylacetamido)-3-(1-carboxymethyltetrazol-5-ylthiomethyl)-3-cephem-4-carboxylic acid; m.p. >160°, slow decomp.

Anal. Calcd. for $C_{20}H_{23}N_7O_6S_2 \cdot \frac{1}{2} H_2O$: C, 45.18; H, 4.55; N, 18.44. Found: C, 45.46; H, 4.68; N, 17.09.

The IR and NMR spectra were consistent for the structure.

EXAMPLE 5

7-(α-Amino-4-hydroxyphenylacetamido)-3-(1-carboxymethyltetrazol-5-ylthiomethyl)-3-cephem-4-carboxylic acid

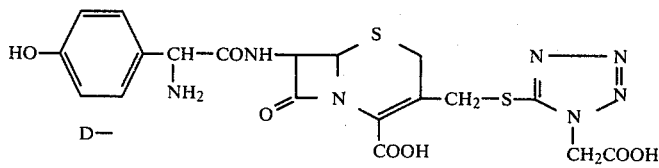

To a solution of 2.7 g. (0.01 mole) of D-(−)-N-tert-butoxycarbonyl-p-hydroxyphenylglycine in 92 ml. of tetrahydrofuran was added 1.1 g. (0.01 mole) of N-methylmorpholine. The solution was cooled to 0° and 1.4 g. (0.01 mole) of isobutylchloroformate was added all at once. The stirring was continued for 10 minutes and the mixed anhydride solution was added to a 0° solution of 3.7 g. (0.01 mole) of 7-amino-3-(1-carboxymethyltetrazol-5-ylthiomethyl)-3-cephem-4-carboxylic acid and 1.1 g. (0.01 mole) of N-methylmorpholine in 50 ml. of water. The solution was stirred for 1 hr. and the tetrahydrofuran was evaporated at 30° (15 mm) to a total volume of 45 ml. The solution was lowered to pH 2 with 1:1 phosphoric acid and extracted with ethyl acetate, washed with water and the solvent was azeotroped to a glassy solid at 30° (15 mm). The residue was triturated with ether to remove any starting acid and collected by filtration. This was hydroscopic and was transferred immediately to 5 ml. of trifluoroacetic acid and stirred for 1 hr. at 27°. The solution was diluted with 25 ml. of ether and the product was collected by filtration and suspended in 5 ml. of water. The mixture was adjusted to pH 3 with conc. ammonium hydroxide and diluted with 10 ml. of isopropanol. The light tan solid was collected by filtration and dried in vacuo over $P_2O_5$ for 24 hr. to yield 300 mg. 7-(α-amino-4-hydroxyphenylacetamido)-3-(1-carboxymethyltetrazol-5-ylthiomethyl-3-cephem-4-carboxylic acid. M.p. 175° slow decomp. Anal. Calcd. for $C_{19}H_{19}N_7O_7S_2 \cdot \frac{3}{4}$ i-$C_3H_7O$: C, 42.78; H, 4.44; N, 17.32. Found: C, 42.86; H, 4.55; N, 15.39. The IR and NMR spectra were consistant for the structure. The NMR spectrum did show the presence of 0.75 mole isopropyl alcohol in the product.

EXAMPLE 6

Substitution in the procedure of example 2 for the D-(−)-2-formyloxy-2-phenylacetyl chloride used therein of an equimolar quantity of monosubstituted D-(−)-2-formyloxy-2-phenylacetyl chloride prepared from the following monosubstituted D-mandelic acids:
D-2-chloro-mandelic acid;
D-3-chloro-mandelic acid,
D-4-chloro-mandelic acid,
D-2-bromo-mandelic acid,
D-3-bromo-mandelic acid,
D-4-bromo-mandelic acid,
D-2-fluoro-mandelic acid,
D-3-fluoro-mandelic acid,
D-4-fluoro-mandelic acid,
D-2-trifluoromethyl-mandelic acid,
D-3-trifluoromethyl-mandelic acid,
D-4-trifluoromethyl-mandelic acid,
D-2-amino-mandelic acid,
D-3-amino-mandelic acid,
D-4-amino-mandelic acid,
D-2-nitro-mandelic acid,
D-3-nitro-mandelic acid,
D-4-nitro-mandelic acid,
D-2-hydroxy-mandelic acid,
D-3-hydroxy-mandelic acid,
D-4-hydroxy-mandelic acid,
D-2-methyl-mandelic acid,
D-3-methyl-mandelic acid,
D-4-methyl-mandelic acid,
D-2-methoxy-mandelic acid,
D-3-methoxy-mandelic acid,
D-4-methoxy-mandelic acid respectively produces the monosubstituted 7-(D-α-formyloxyphenylacetamido)-3-(1-carboxymethyltetrazol-5-ylthiomethyl)-3-cephem-4-carboxylic acid compound in step A, which is subsequently converted to
Dipotassium 7-(D-2-chloro-mandelamido)-3-(1-carboxymethyltetrazol-5-ylthiomethyl)-3-cephem-4-carboxylate,
Dipotassium 7-(D-3-chloro-mandelamido)-3-(1-carboxymethyltetrazol-5-ylthiomethyl)-3-cephem-4-carboxylate,
Dipotassium 7-(D-4-chloro-mandelamido)-3-(1-carboxymethyltetrazol-5-ylthiomethyl)-3-cephem-4-carboxylate,
Dipotassium 7-(D-2-bromo-mandelamido)-3-(1-carboxymethyltetrazol-5-ylthiomethyl)-3-cephem-4-carboxylate,
Dipotassium 7-(D-3-bromo-mandelamido)-3-(1-carboxymethyltetrazol-5-ylthiomethyl)-3-cephem-4-carboxylate, Dipotassium 7-(D-4-bromo-mandelamido)-3-(1-carboxymethyltetrazol-5-ylthiomethyl)-3-cephem-4-carboxylate, Dipotassium 7-(D-2-fluoro-mandelamido)-3-(1-carboxymethyltetrazol-5-ylthiomethyl)-3-cephem-4-carboxylate, Dipotassium 7-(D-3-fluoro-mandelamido)-3-(1-carboxymethyltetrazol-5-ylthiomethyl)-3-cephem-4-carboxylate, Dipotassium 7-(D-4-fluoro-mandelamido)-3-(1-carboxymethyltetrazol-5-ylthiomethyl)-3cephem-4-carboxylate, Dipotassium 7-(D-2-trifluoromethyl-mandelamido)-3-(1-carboxymethyltetrazol-5-ylthiomethyl)-3-cephem-4-carboxylate, Dipotassium 7-(D-3-trifluoromethyl-mandelamido)-3-(1-carboxymethyltetrazol-5-ylthiomethyl)-3-cephem-4-carboxylate, Dipotassium 7-(D-4-trifluoromethyl-mandelamido)-3-(1-carboxymethyltetrazol-5-ylthiomethyl)-3-cephem-4-carboxylate, Dipotassium 7-(D-2-amino-mandelamido)-3-(1-carboxymethyltetrazol-5-ylthiomethyl)-3-cephem-4-carboxylate, Dipotassium 7-(D-3-amino-mandelamido)-3-(1-carboxymethyltetrazol-5-ylthiomethyl)-3-cephem-4-carboxylate, Dipotassium 7-(D-4-amino-mandelamido)-3-(1-carboxymethyltetrazol-5-ylthiomethyl)-3-cephem-4-carboxylate, Dipotassium 7-(D-2-nitro-mandelamido)-3-(1-carboxymethyltetrazol-5-ylthiomethyl)-3-cephem-4-carboxylate, Dipotassium 7-(D-3-nitro-mandelamido)-3-(1-carboxymethyltetrazol-5-ylthiomethyl)-3-cephem-4-carboxylate, Dipotassium 7-(D-4-nitro-mandelamido)-3-(1-carboxymethyltetrazol-5-ylthiomethyl)-3-cephem-4-carboxylate, Dipotassium 7-(D-2-hydroxy-mandelamido)-3-(1-carboxymethyltetrazol-5-ylthiomethyl)-3-cephem-4-carboxylate, Dipotassium 7-(D-3-hydroxy-mandelamido)-3-(1-carboxymethyltetrazol-5-ylthiomethyl)-3-cephem-4-carboxylate, Dipotassium 7-(D-4-hydroxy-mandelamido)-3-(1-carboxymethyltetrazol-5-ylthiomethyl)-3-cephem-4-carboxylate, Dipotassium 7-(D-α-formyloxyphenylacetamido)-3-(1-carboxymethyltetrazol-5-ylthiomethyl)-3-cephem-4-carboxylate, Dipotassium 7-(D-2-methyl-mandelamido)-3-(1-carboxymethyltetrazol-5-ylthiomethyl)-3-cephem-4-carboxylate, Dipotassium 7-(D-3-methyl-mandelamido)-3-(1-carboxymethyltetrazol-5-ylthiomethyl)-3-cephem-4-carboxylate, dipotassium 7-(D-4-methyl-mandelamido)-3-(1-carboxymethyltetrazol-5-ylthiomethyl)-3-cephem-4-carboxylate, Dipotassium 7-(D-2-methoxy-mandelamido)-3-(1-carboxymethyltetrazol-5-ylthiomethyl)-3-cephem-4-carboxylate, Dipotassium 7-(D-3-methoxy-mandelamido)-3-(1-carboxymethyltetrazol-5-ylthiomethyl)-3-cephem-4-carboxylate and Dipotassium 7-(D-4-methoxy-mandelamido)-3-(1-carboxymethyltetrazol-5-ylthiomethyl)-3-cephem-4-carboxylate respectively.

EXAMPLE 7

Substitution for the D-mandelic acid carboxyanhydrides in the procedure of Example 27 of an equimolar weight of the carboxyanhydride prepared in similar fashion from D-2-thiopheneglycolic acid and D-3-thiopheneglycolic acid respectively produces dipotassium 7-(D-α-hydroxy-2-thienylacetamido)-3-(1-carboxymethyltetrazol-5-ylthiomethyl)-3-cephem-4-carboxylate and dipotassium 7-(D-α-hydroxy-3-thienylacetamido)-3-(1-carboxymethyltetrazol-5-yl-thiomethyl)-3-cephem-4-carboxylate respectively.

EXAMPLE 8

Substitution in the procedure of Example 3 for the N-tert.-butoxycarbonyl derivative of D-α-aminophenylacetic acid (also called D-α-tert.-butoxycarboxamidophenylacetic acid) of an equimolar weight of the N-tert.-butoxycarbonyl derivative of D-α-amino-2-thienylacetic acid,
D-α-amino-3-thienylacetic acid,
d-α-amino-m-nitrophenylacetic acid,
D-α-amino-p-methylphenylacetic acid,
D-α-amino-m-methylphenylacetic acid,
D-α-amino-p-chlorophenylacetic acid,
D-α-amino-m-chlorophenylacetic acid,
D-α-amino-p-fluorophenylacetic acid,
D-α-amino-m-fluorophenylacetic acid,
D-α-amino-p-aminophenylacetic acid,
D-α-amino-p-dimethylaminophenylacetic acid,
D-α-amino-m,p-dimethoxyphenylacetic acid,
D-α-amino-p-iodophenylacetic acid,
D-α-amino-m-chloro-p-hydroxyphenylacetic acid,
D-α-amino-p-methoxyphenylacetic acid,
D-α-amino-m-methoxyphenylacetic acid,
D-α-amino-m-hydroxyphenylacetic acid,
D-α-amino-p-acetamidophenylacetic acid,
D-α-amino-m-aminophenylacetic acid, and
D-α-amino-m-acetamidophenylacetic acid, respectively, produces 7-(D-α-amino-thienylacetamido)-3-(1-carboxymethyltetrazol-5-ylthiomethyl)-ceph-3-em-4-oic acid,
7-(D-α-amino-3-thienylacetamido)-3-(1-carboxymethyltetrazol-5-ylthiomethyl)-ceph-3-em-4-oic acid,
7-(D-α-amino-m-nitrophenylacetamido)-3-(1-carboxymethyltetrazol-5-ylthiomethyl)-ceph-3-em-4-oic acid,
7-(D-α-amino-p-methylphenylacetamido)-3-(1-carboxymethyltetrazol-5-ylthiomethyl)-ceph-3-em-4-oic acid,
7-(D-α-amino-m-methylphenylacetamido)-3-(1-carboxymethyltetrazol-5-ylthiomethyl)-ceph-3-em-4-oic acid,
7-(D-α-amino-p-chlorophenylacetamido)-3-(1-carboxymethyltetrazol-5-ylthiomethyl)-ceph-3-em-4-oic acid,
7-(D-α-amino-m-chlorophenylacetamido)-3-(1-carboxymethyltetrazol-5-ylthiomethyl)-ceph-3-em-4-oic acid,
7-(D-α-amino-p-fluorophenylacetamido)-3-(1-carboxymethyltetrazol-5-ylthiomethyl)-ceph-3-em-4-oic acid,
7-(D-α-amino-m-fluorophenylacetamido)-3-(1-carboxymethyltetrazol-5-ylthiomethyl)-ceph-3-em-4-oic acid, 7-(D-α-amino-p-aminophenylacetamido)-3-(1-carboxymethyltetrazol-5-ylthiomethyl)-ceph-3-em-4-oic acid, 7-(D-α-amino-p-dimethylaminophenylacetamido)-3-(1-carboxymethyltetrazol-5-ylthiomethyl)-ceph-3-em-4-oic acid, 7-(D-α-amino-m-p-dimethoxyphenylacetamido)-3-(1-carboxymethyltetrazol-5-ylthiomethyl)-ceph-3-em-4-oic acid, 7-(D-α-amino-m-iodophenylacetamido)-3-(1-carboxymethyltetrazol-5-ylthiomethyl)-ceph-3-em-4-oic acid, 7-(D-α-amino-m-chloro-p-hydroxyphenylacetamido)-3-(1-carboxymethyltetrazol-5-ylthiomethyl)-ceph-3-em-4-oic acid 7-(D-α-amino-p-methoxyphenylacetamido)-3-(1-carboxymethyltetrazol-5-ylthiomethyl)-ceph-3-em-4-oic acid, 7-(D-α-amino-m-methoxyphenylacetamido)-3-(1-carboxymethyltetrazol-5-ylthiomethyl)-ceph-3-em-4-oic acid, 7-(D-α-amino-m-hydroxyphenylacetamido)-3-(1-carboxymethyltetrazol-5-ylthiomethyl)-ceph-3-em-4-oic acid, 7-(D-α-amino-p-acetamidophenylacetamido)-3-(1-carboxymethyltetrazol-5-ylthiomethyl)-ceph-3-em-4-oic acid, 7-(D-α-amino-m-aminophenylacetamido)-3-(1-carboxymethyltetrazol-5-ylthiomethyl)-ceph-3-em-4-oic acid, and 7-(D-α-amino-m-acetamidophenylacetamido)-3-(1-carboxymethyltetrazol-5-ylthiomethyl)-ceph-3-em-4-oic acid, respectively.

EXAMPLE 9

7-Phenoxyacetamido-3-(1-carboxymethyltetrazol-5-ylthiomethyl)-3-cephem-4-carboxylic acid by thiolation of 7-phenoxyacetamidocephalosporanic acid Sodium 7-phenoxyacetamidocephalosporanate (0.27 mole) is suspended in 1000 ml. of 0.1 M phosphate buffer pH 6.4 to which is added 0.31 mole disodium 1-carboxymethyl-5-mercaptotetrazole. The solution is heated at 55° C. under a nitrogen atmosphere for 5 hr. After 1 hr. the pH is adjusted to 6.4 by addition of a small amount of 40% $H_3PO_4$. At the end of the 5 hr. heating period, the solution is cooled to 23° C. and the pH adjusted to 2 by addition of 3 N HCl under a layer of ethyl acetate. The product is extracted into ethyl acetate and stirred for 15 min. at 23° C. with 2 g. of ("Darco KB") decolorizing charcoal. It is then filtered through a pad of diatomaceous earth ("Celite") and the ethyl acetate removed under vacuum to leave an oil which is triturated to a solid with diethyl ether, collected by filtration and dried over $P_2O_5$ under vacuum to yield solid 7-phenoxyacetamido-3-(1-carboxymethyltetrazol-5-ylthiomethyl)-3-cephem-4-carboxylic acid.

EXAMPLE 10

Replacement of the sodium 7-phenoxyacetamidocephalosporanate in the procedure of Example 9 with an equimolar weight of
sodium 7-phenylacetamido-cephalosporanate,
sodium 7-(2-thienylacetamido)-cephalosporanate,
sodium 7-(3-thienylacetamido)-cephalosporanate,
sodium 7-(4-pyridylthioacetamido)-cephalosporanate,
sodium 7-(cyanoacetamido-cephalosporanate,
sodium 7-(1-tetrazolylacetamido)-cephalosporanate,
sodium 7-trifluoromethylthioacetamido-cephalosporanate,
sodium 7-(α-azidophenylacetamido)-cephalosporanate,
sodium 7-sydnone-3-acetamido-cephalosporanate,
sodium 7-chloroacetamido-cephalosporanate, and
sodium 7-bromoacetamido-cephalosporanate, respectively, produces
7-phenylacetamido-3-(1-carboxymethyltetrazol-5-ylthiomethyl)-3-cephem-4-carboxylic acid,
7-(2-thienylacetamido)-3-(1-carboxymethyltetrazol-5-ylthiomethyl)-3-cephem-4-carboxylic acid,
7-(3-thienylacetamido)-3-(1-carboxymethyltetrazol-5-ylthiomethyl)-3-cephem-4-carboxylic acid,
7-(4-pyridylthioacetamido)-3-(1-carboxymethyltetrazol-5-ylthiomethyl)-3-cephem-4-carboxylic acid,
7-cyanoacetamido-3-(1-carboxymethyltetrazol-5-ylthiomethyl)-3-cephem-4-carboxylic acid,
7-(1-tetrazolylacetamido)-3-(1-carboxymethyltetrazol-5-ylthiomethyl)-3-cephem-4-carboxylic acid,
7-trifluoromethylthioacetamido-3-(1-carboxymethyltetrazol-5-ylthiomethyl)-3-cephem-4-carboxylic acid,
7-(α-azidophenylacetamido)-3-(1-carboxymethyltetrazol-5-ylthiomethyl)-3-cephem-4-carboxylic acid,
7-sydnone-3-acetamido-3-(1-carboxymethyltetrazol-5-ylthiomethyl)-3-cephem-4-carboxylic acid,
7-chloroacetamido-3-(1-carboxymethyltetrazol-5-ylthiomethyl)-3-cephem-4-carboxylic acid, and
7-bromoacetamido-3-(1-carboxymethyltetrazol-5-ylthiomethyl)-3-cephem-4-carboxylic acid, respectively.

EXAMPLE 11

7-[D-α-Amino-α-(p-hydroxyphenyl)acetamido]-3-(1-carboxymethyltetrazol-5-ylthiomethyl)-3-cephem-4-carboxylic acid by thiolation of 7-[D-α-t-butoxycarbonylamino-α-(p-hydroxyphenyl)acetamidocephalosporanic acid followed by deblocking

A.

7-[α-(4-Hydroxyphenyl)-α-D-(t-butoxycarbonylamino)-acetamido]-3-(1-carboxymethyltetrazol-5-ylthiomethyl)-3-cephem-4-carboxylic acid Sodium 7-[α-(4-hydroxyphenyl)-α-D-(t-butoxycarbonylamino)-acetamido]cephalosporanate (0.27 mole) is suspended in 1000 ml. of 0.1 M phosphate buffer pH 6.4 to which is added 0.31 mole disodium 1-carboxymethyl-5-mercaptotetrazole. The solution is heated at 55° C. under a nitrogen atmosphere for 5 hr. After 1 hr. the pH is adjusted to 6.4 by addition of a small amount of 40% $H_3PO_4$. At the end of the 5 hr. heating period, the solution is cooled to 23° C. and the pH adjusted to 2 by addition of 3 N HCl under a layer of ethyl acetate. The product is extracted into ethyl acetate and stirred for 15 min. at 23° C. with 2 g. of ("Darco KB") decolorizing charcoal. It is then filtered through a pad of diatomaceous earth ("Celite") and the ethyl acetate removed under vacuum to leave an oil which is triturated to a solid with diethyl ether, collected by filtration and dried over $P_2O_5$ under vacuum to yield solid 7-[α-(4-hydroxyphenyl)-α-D-(t-butoxycarbonylamino)-acetamido]-3-(1-carboxymethyltetrazol-5-ylthiomethyl)-3-cephem-4-carboxylic acid.

B.
7-[D-α-Amino-α-(p-hydroxyphenyl)acetamido]-3-(1-carboxymethyltetrazol-5-ylthiometyl)-3-cephem-4-carboxylic acid 7-[α-(4-Hydroxyphenyl)-α-D-(t-butoxycarbonylamino)-acetamido]-3-(1-carboxymethyltetrazol-5-yl-thiometyl)-3-cephem-4-carboxylic acid (0.1 mole) is dissolved in 30 ml. of trifluoroacetic acid at 5° C. It is allowed to come to 23° C. and stirred for an additional 30 min. This solution is slowly poured into 1000 ml. of anhydrous ethyl ether with vigorous stirring. The precipitate is collected by filtration, washed with 100 ml. ethyl ether and dried over $P_2O_5$ under vacuum for 1 hr. It is then dissolved in 75 ml. $H_2O$ and after stirring 30 min. at 23° C. the solids are filtered off. 2 g. of ("Darco KB") decolorizing charcoal is added to the filtrate and after stirring 10 min. at 23° C. the slurry is filtered through a "Celite" pad. The pH of the filtrate is adjusted to 4 by addition of triethylamine and the solids filtered off. The filtrate is evaporated under high vacuum to an oil and triturated with acetonitrile. The product 7-[D-α-amino-α-(p-hydroxyphenyl)acetamido]-3-(1-carboxymethyltetrazol-5-ylthiomethyl)-3-cephem-4-carboxylic acid, is collected by filtration and air dried.

EXAMPLE 12

Replacement of the sodium 7-[α-(4-hydroxyphenyl)-α-D-(t-butoxycarbonylamino)acetamido]-cephalosporanate in the procedure of Example 11 with an equimolar weight of the cephalosporanic acid produced, for example, by acylation of 7-ACA in the usual manner with 2-(tert.-butoxycarbonylaminomethyl)-1,4-cyclohexadienylacetic acid,
D-(−)-α-tert.-butoxycarboxamidophenylacetic acid,
2-(tert.-butoxycarbonylaminomethyl)-1,2-cyclohexenylacetic acid,
2-t-butoxycarbonylaminomethyl-4-hydroxyphenylacetic acid,
o-(tert.-butoxycarbonylamino ethyl)phenylthioacetic acid,
β-[o-(tert.-butoxycarbonylaminomethyl)phenyl]propionic acid,
D-(−)-N-t-butoxycarbonyl-2-(3'-methyl-4'-hydroxyphenyl)glycine,
D-(−)-N-t-butoxycarbonyl-2-(3'-methoxy-4'-hydroxyphenyl)glycine,
D-(−)-N-t-butoxycarbonyl-2-(4-acetoxyphenyl)glycine,
D-(−)-N-t-butoxycarbonyl-2-(1'-cyclohexenyl)glycine,
D-(−)-N-t-butoxycarbonyl-2-(3'-chloro-4'-hydroxyphenyl)glycine,
D-(−)-N-t-butoxycarbonyl-2-(1',4'-cyclohexadienyl)glycine,
D-(−)-2-tert.-butoxycarboxamido-3-(1',4'-cyclohexadienyl)propionic acid,
D-(−)-2-tert.-butoxycarboxamido-3-(4'-methoxy 1',4'-cyclohexadienyl)propionic acid,
2-t-butoxycarbonylaminomethylphenyl-acetic acid, N-tert.-butoxycarbonyl-1-aminocyclohexanecarboxylic acid,
D-(−)-α-tert.-butoxycarboxamido-3-thienylacetic acid,
D-(−)-α-tert.-butoxycarboxamido-2-thienylacetic acid,
β(2-tert.-butoxycarbonylaminomethyl-1,4-cyclohexadienyl)propionic acid,
β(2-t-butoxycarbonylaminomethyl-1-cyclohexenyl)propionic acid, and
D-(−)-N-tert.-butoxycarbonyl-2-(4'-hydroxymethylphenyl)glycine, respectively, produces 7-(2-aminomethyl-1,4-cyclohexadienylacetamido)-3-(1-carboxymethyltetrazol-5-ylthiomethyl)-3-cephem-4-carboxylic acid,
7-(D-α-aminophenylacetamido)-3-(1-carboxymethyltetrazol-5-ylthiomethyl)-3-cephem-4-carboxylic acid,
7-(2-aminomethyl-1,2-cyclohexenylacetamido)-3-(1-carboxymethyltetrazol-5-ylthiomethyl)-3-cephem-4-carboxylic acid,
7-(2-aminomethyl-4-hydroxyphenylacetamido)-3-(1-carboxymethyltetrazol-5-ylthiomethyl)-3-cephem-4-carboxylic acid,
7-(o-aminomethylphenylthioacetamido)-3-(1-carboxymethyltetrazol-5-ylthiomethyl)-3-cephem-4-carboxylic acid,
7-[β-(o-aminomethylphenyl)propionamido[-3-(1-carboxymethyltetrazol-5-ylthiomethyl)-3-cephem-4-carboxylic acid,
7-[D-α-amino-α-(3'-methyl-4'-hydroxyphenyl)acetamido]-3-(1-carboxymethyltetrazol-5-ylthiomethyl)-3-cephem-4-carboxylic acid,
7-[D-α-amino-α-(3'-methoxy-4'-hydroxyphenyl)acetamido]3-(1-carboxymethyltetrazol-5-ylthiomethyl)-3-cephem-4-carboxylic acid,
7-[D-α-amino-α-(4-acetoxyphenyl)acetamido]-3-(1-carboxymethyltetrazol-5-ylthiomethyl)-3-cephem-4-carboxylic acid,
7-[D-α-amino-α-(1'-cyclohexenyl)acetamido]-3-(1-carboxymethyltetrazol-5-ylthiomethyl)-3-cephem-4-carboxylic acid,
7-[D-α-amino-α-(3'-chloro-4'-hydroxyphenyl)acetamido]3-(1-carboxymethyltetrazol-5-ylthiomethyl)-3-cephem-4-carboxylic acid,
7-[D-α-amino-α-(1',4'-cyclohexadienyl)acetamido]-3-(1-carboxymethyltetrazol-5-ylthiomethyl)-3-cephem-4-carboxylic acid,
7-[D-(1',4'-cyclohexadienyl)propionamido]-3-(1-carboxymethyltetrazol-5-ylthio ethyl)-3-cephem-4-carboxylic acid,
7-[D-(4'-methoxy-1',4'-cyclohexadienyl)propionamido]-3-(1-carboxymethyltetrazol-5-ylthiomethyl)-3-cephem-4-carboxylic acid,
7-(2-aminomethylphenylacetamido)-3-(1-carboxymethyltetrazol-5-ylthiomethyl)-3-cephem-4-carboxylic acid,
7-(1-aminocyclohexanecarboxamido-3-(1-carboxymethyltetrazol-5-ylthiomethyl)-3-cephem-4-carboxylic acid,
7-(D-α-amino-3-thienylacetamido)-3-(1-carboxymethyltetrazol-5-ylthiomethyl)-3-cephem-4-carboxylic acid,
7-(D-α-amino-2-thienylacetamido)-3-(1-carboxymethyltetrazol-5-ylthiomethyl)-3-cephem-4-carboxylic acid,
7-(2-aminomethyl-1,4-cyclohexadienyl-propionamido)-3-(1-carboxymethyltetrazol-5-ylthiomethyl)-3-cephem-4-carboxylic acid,
7-[β-(aminomethyl-1-cyclohexenyl)propionamido]-3-(1-carboxymethyltetrazol-5-ylthiomethyl)-3-cephem-4-carboxylic acid and
7-[D-α-amino-α-(4'-hydroxymethylphenyl)acetamido]-3-(1-carboxymethyltetrazol-5-ylthiomethyl)-3-cephem-4-carboxylic acid, respectively.

EXAMPLE 13

Replacement of the D-(—)-N-tert.-butoxycarbonyl-p-hydroxyphenylglycine in the procedure of Example 5 with an equimolar weight of 2-(tert.-butoxycarbonylaminomethyl)-1,4-cyclohexadienylacetic acid, D-(—)-α-tert.-butoxycarboxamidophenylacetic acid, 2-(tert.-butoxycarbonylaminomethyl)-1,2-cyclohexenylacetic acid, 2-t-butoxycarbonylaminomethyl-4-hydroxyphenylacetic acid, o-(tert.-butoxycarbonylamino ethyl)phenylthioacetic acid, β[o-(tert.-butoxycarbonylaminomethyl)phenyl]propionic acid, D-(—)-N-t-butoxycarbonyl-2-(3'-methyl-4'-hydroxyphenyl)glycine, D-(—)-N-t-butoxycarbonyl-2-(3'-methoxy-4'-hydroxyphenyl)glycine, D-(—)-N-t-butoxycarbonyl-2-(4-acetoxyphenyl)glycine, D-(—)-N-t-butoxycarbonyl-2-(1'-cyclohexenyl)glycine, D-(—)-N-t-butoxycarbonyl-2-(3'-chloro-4'-hydroxyphenyl)glycine, D-(—)-N-t-butoxycarbonyl-2-(1',4'-cyclohexadienyl)glycine, D-(—)-2-tert.-butoxycarboxamido-3-(1',4'-cyclohexadienyl)propionic acid, D-(—)-2-tert.-butoxycarboxamido-3-(4'-methoxy 1',4'-cyclohexadienyl)propionic acid, 2-t-butoxycarbonylaminomethylphenyl-acetic acid, N-tert.-butoxycarbonyl-1-aminocyclohexanecarboxylic acid, D-(—)-α-tert.-butoxycarboxamido-3-thienylacetic acid, D-(—)-α-tert.-butoxycarboxamido-2-thienylacetic acid, β-(2-tert.-butoxycarbonylaminomethyl-1,4-cyclohexadienyl)propionic acid, β-(2-t-butoxycarbonylaminomethyl-1-cyclohexenyl)propionic acid, and D-(—)-N-tert.-butoxycarbonyl-2-(4'-hydroxymethylphenyl)glycine, respectively, produces 7-(2-aminomethyl-1,4-cyclohexadienylacetamido)-3-(1-carboxymethyltetrazol-5-ylthiomethyl)-3-cephem-4-carboxylic acid, 7-(D-α-aminophenylacetamido)-3-(1-carboxymethyltetrazol-5-ylthiomethyl)-3-cephem-4-carboxylic acid, 7-(2-aminomethyl-1,2-cyclohexenylacetamido)-3-(1-carboxymethyltetrazol-5-ylthiomethyl)-3-cephem-4-carboxylic acid, 7-(2-aminomethyl-4-hydroxyphenylacetamido)-3-(1-carboxymethyltetrazol-5-ylthiomethyl)-3-cephem-4-carboxylic acid, 7-(o-aminomethylphenylthioacetamido)-3-(1-carboxymethyltetrazol-5-ylthiomethyl)-3-cephem-4-carboxylic acid, 7-[β-(o-aminomethylphenyl)propionamido]-3-(1-carboxymethyltetrazol-5-ylthiomethyl)-3-cephem-4-carboxylic acid, 7-[D-α-amino-α-(3'-methyl-4'-hydroxyphenyl)acetamido]-3-(1-carboxymethyltetrazol-5-ylthiomethyl)-3-cephem-4-carboxylic acid, 7-[D-α-amino-α-(3'-methoxy-4'-hydroxyphenyl)acetamido]-3-(1-carboxymethyltetrazol-5-ylthiomethyl)-3-cephem-4-carboxylic acid, 7-[D-α-amino-α-(4-acetoxyphenyl)acetamido]-3-(1-carboxymethyltetrazol-5-ylthiomethyl)-3-cephem-4-carboxylic acid, 7-[D-α-amino-α-(1'-cyclohexenyl)acetamido]-3-(1-carboxymethyltetrazol-5-ylthiomethyl)-3-cephem-4-carboxylic acid, 7-[D-α-amino-α-(3'-chloro-4'-hydroxyphenyl)acetamido]3-(1-carboxymethyltetrazol-5-ylthiomethyl)-3-cephem-4-carboxylic acid, 7-[D-α-amino-α-(1',4'-cyclohexadienyl)acetamido]-3-(1-carboxymethyltetrazol-5-ylthiomethyl)-3-cephem-4-carboxylic acid, 7-[D-(1',4'-cyclohexadienyl)propionamido]-3-(1-carboxymethyltetrazol-5-ylthioethyl)-3-cephem-4-carboxylic acid, 7-[D-(4'-methoxy-1',4'-cyclohexadienyl)propionamido]-3-(1-carboxymethyltetrazol-5-ylthiomethyl)-3-cephem-4-carboxylic acid, 7-(2-aminomethylphenylacetamido)-3-(1-carboxymethyltetrazol-5-ylthiomethyl)-3-cephem-4-carboxylic acid, 7-(1-aminocyclohexanecarboxamido- 3-(1-carboxymethyltetrazol-5-ylthiomethyl)-3-cephem-4-carboxylic acid, 7-(D-α-amino-3-thienylacetamido)-3-(1-carboxymethyltetrazol-5-ylthiomethyl)-3-cephem-4-carboxylic acid, 7-(D-α-amino-2-thienylacetamido)-3-(1-carboxymethyltetrazol-5-ylthiomethyl)-3-cephem-4-carboxylic acid, 7-(2-aminomethyl-1,4-cyclohexadienyl-propionamido)-3-(1-carboxymethyltetrazol-5-ylthiomethyl)-3-cephem-4-carboxylic acid, 7-[β-(aminomethyl-1-cyclohexenyl)propionamido]-3-(1-carboxymethyltetrazol-5-ylthiomethyl)-3-cephem-4-carboxylic acid and 7-[D-α-amino-α-(4'-hydroxymethylphenyl)acetamido]-3-(1-carboxymethyltetrazol-5-ylthiomethyl)-3-cephem-4-carboxylic acid, respectively.

EXAMPLE 14

Sodium 7-{D-α-[3-(2-furoyl)ureido]-4-hydroxyphenylacetamido}cephalosporanate

Triethylamine (6.4 ml., 0.0454 mole) and 12.7 g. (0.1039 mole) of 2-furoyl isocyanate was added to an ice cooled suspension of 20.8 g. (0.0413 mole) of 7-(D-α-amino-4-hydroxyphenylacetamido)cephalosporanic acid (as a dimethylformamide-water solvate) in 175 ml. of dry dimethylformamide. After about 1 minute the ice bath was removed and the mixture stirred for 1 hr. The dark solution was diluted with 600 ml. of water, layered with ethyl acetate and the aqueous phase acidified to pH 2.5 with 42% phosphoric acid. The phases were separated and the aqueous dimethylformamide phase was extracted four times more with ethyl acetate. The combined organic extracts were washed five times with water, carbon treated, filtered and concentrated at reduced pressure to remove residual water. Fresh ethyl acetate was added and the stirred solution was treated slowly with 15.1 ml. (0.0408 mole) of sodium 2-ethylhexanoate in 1-butanol causing the product to crystallize; 18.1 g., 75.5%. The IR spectrum was consistent for the desired product.

7-{D-α-[3-(2-Furoyl)ureido]-4-hydroxyphenylacetamido}3-(1-carboxymethyltetrazol-5-ylthiomethyl)-cephem-4-carboxylic acid disodium salt A mixture of 4.0 g. (0.0069 mole) of sodium 7-{D-α-[3-(2-furoyl)ureido]-4-hydroxyphenylacetamido}cephalosporanate, 1.83 g. (0.00895 mole) of 5-mercapto-1-tetrazole acetic acid disodium salt and 200 ml. of pH 6.4, 0.1 M phosphate buffer was heated at 75° for 6 hours under a nitrogen atmosphere. The reaction mixture which had been stored in the refrigerator overnight was filtered to remove a small amount of precipitate. The filtrate was adjusted to pH 2 with 6 N HCl and the mixture extracted three times with ethyl acetate. The mixture was filtered during the first extraction to remove a small amount of insoluble material. The combined ethyl acetate extracts (volume=500 ml.) were washed twice with water, dried (sodium sulfate) filtered and treated with 5.1 ml. (0.0138 mole, 2 eqv.) of sodium 2-ethylhexanoate in 1-butanol causing an oil to separate. The solvent was concentrated somewhat to remove water and the mixture stored in the refrigerator. The solvent was decanted and the gummy product was triturated with acetone giving a filterable solid; yield 2.0 g. The product was dried in vacuo over phosphorus pentoxide. The IR spectrum was consistent for the desired product.

Samples of the compounds prepared in Examples 1, 2, 3, 4, 5 and 14 after solution in water and dilution with Nutrient Broth were found to exhibit the following Minimum Inhibitory Concentrations (M.I.C.) in mcg./ml. versus the indicated microorganisms as determined by overnight incubation at 37° C. by Tube Dilution.

| Organisms | | Ex. 1 (soluble at ≥250 mg/ml as Na+ salt) | Ex. 2 | Ex. 3 | Ex. 4 | Ex. 14 | Ex. 5 |
|---|---|---|---|---|---|---|---|
| Str. pneumoniae* $(10^{-3})$** | A9585 | 0.13 | 0.6 | 0.6 | 0.06 | 0.13 | 0.25 |
| Str. pyogenes* $(10^{-3})$ | A9604 | 0.13 | 0.6 | 0.6 | 0.13 | 0.13 | 1 |
| S. aureus Smith $(10^{-4})$ | A9537 | 1 | 1.3 | 2.5 | 0.5 | >1 | >1 |
| S. aureus-50% serum $(10^{-4})$ | A9537 | 4 | 16 | 32 | >0.5 | >63 | 16 |
| S. aureus BX1633 $(10^{-3})$ | A9606 | 1 | 2.5 | >2.5 | 1.3 | 2 | 8 |
| S. aureus BX1633 $(10^{-2})$ | A9606 | 2 | 4 | 16 | 2.5 | 8 | 8 |
| S. aureus Meth-Res $(10^{-3})$ | A15097 | 4 | 8 | 16 | 4 | 63 | 32 |
| Sal. enteritidis $(10^4)$ | A9531 | 0.06 | 0.08 | 0.3 | 0.16 | 0.5 | 0.5 |
| E. coli Juhl $(10^{-4})$ | A15119 | 0.5 | 4 | 8 | 1.3 | 16 | 8 |
| E. coli $(10^{-4})$ | A9675 | 16 | 32 | 16 | 16 | 16 | 32 |
| K. pneumoniae $(10^{-4})$ | A9977 | 0.13 | 1 | 1 | 0.3 | 1 | 1 |
| K. pneunomiae $(10^{-4})$ | A15130 | 2 | 32 | 8 | 2 | 125 | 8 |
| Pr. mirabilis $(10^{-4})$ | A9900 | 0.13 | 0.5 | 1 | 0.3 | 0.5 | 1 |
| Pr. morganii $(10^{-4})$ | A15153 | 32 | 16 | 32 | 8 | 32 | 125 |
| Ps. aeruginosa $(10^{-4})$ | A9843A | >125 | >125 | >125 | >125 | 16 | >125 |
| Ser. marcescens $(10^{-4})$ | A20019 | 125 | >125 | >125 | >125 | >125 | >125 |
| Ent. cloacae $(10^{-4})$ | A9656 | >125 | >125 | >125 | >125 | >125 | >125 |
| Ent. cloacae $(10^{-4})$ | A9657 | 0.25 | 2 | 1 | 0.3 | 63 | 2 |
| Ent. cloacae $(10^{-4})$ | A9659 | 32 | >125 | 63 | 32 | >125 | 125 |

*45% Antibiotic Assay Broth + 50% Nutrient Broth + 5% serum
**Dilution of overnight broth culture

EXAMPLE 15

Trihydrate of Monosodium Salt of 7-(2-Aminomethylphenylacetamido)-3-(1-carboxymethyltetrazol-5-yl-thiomethyl)-3-cephem-4-carboxylic acid 1. Ten grams of crystalline 7-(2-aminomethylphenylacetamido)-3-(1-carboxymethyltetrazol-5-yl-thiomethyl)-3-cephem-4-carboxylic acid (as described and prepared in Example 1) is suspended in 50 ml. of deionized water.

2. Ten percent sodium hydroxide is slowly added with rapid stirring to a maintained or constant pH of 7.4–7.7. A solution or near solution is obtained.

3. Two grams of activated charcoal ("Darco G-60") is added and the mixture is slurried for 0.5 hours. The pH is maintained at 7.4–7.7 with 1 N sodium hydroxide.

4. The carbon is removed by filtration and washed with 10 ml. of water. The wash is added to the filtrate.

5. The pH 7.4–7.7 solution of step 4 is made sterile and pyrogen-free by suitable aseptic filtration and techniques.

The combined time required for completion of steps 3, 4 and 5 should not exceed 5 hours at ambient room temperature.

6. Using sterile technique, an approximate equal volume (65 ml.) of sterile, pyrogen-free acetone is added to the rapidly stirring sterile solution of step 5 over a 5 minute period.

7. Based upon the approximate original aqueous volume, an additional 2 volumes (120 ml.) of sterile, pyrogen-free acetone is added with rapid stirring over 15-20 minutes. Crystals form.

8. The mixture is slurried for 10 minutes.

9. An additional 3 volumes (180 ml.) of sterile acetone is added over a 15 minute interval. The mixture is slurried for 0.5 hour.

10. The crystals are collected by filtration, washed with 75 ml. of sterile acetone and vacuum dried at 45°-50° C. or air dried at 50°-56° C. for 24 hours. Yield: Approximately 8.8 grams.

Properties of trihydrate of monosodium salt of 7-(2-aminomethylphenylacetamido)-3-(1-carboxymethyltetrazol-5-ylthiomethyl)-3-cephem-4-carboxylic acid:

% Water (KF)=9.2 (theory=9.05%)
% Sodium (flame photometer)=4.0 (theory=3.86%)
Solubility in water=>500 mg./ml.
Stability in water=Stable for at least 24 hours at room temperature at 250 mg./ml.

Formulation of Injectable Products

In situ preparation of monosodium salt of 7-(2-aminomethylphenylacetamido)-3-(1-carboxymethyltetrazol-5-ylthiomethyl)-3-cephem-4-carboxylic acid:

(A) 2.5 grams of 7-(2-aminomethylphenylacetamido)-3-(1-carboxymethyltetrazole-5-ylthiomethyl)-3-cephem-4-carboxylic acid (zwitterion) is suspended in 8.5 ml. of water with rapid stirring, sodium citrate or $Na_2HPO_4$ or $Na_3PO_4$ or other suitable "bases" are added until a solution is obtained (the pH should not be over 7.8). The amount of added "base" is noted.

(B) A physical mixture of 2.5 grams of 7-(2-aminomethylphenylacetamido)-3-(1-carboxymethyltetrazol-5-ylthiomethyl)-3-cephem-4-carboxylic acid and the solid "base" in proportions determined in "A" above is made. The later addition of water to obtain various concentrations of 7-(2-aminomethylphenylacetamido)-3-(1-carboxymethyltetrazol-5-ylthiomethyl)-3-cephem-4-carboxylic acid gives a solution of in situ prepared monosodium salt of 7-(2-aminomethylphenylacetamido)-3-(1-carboxymethyltetrazol-5-ylthiomethyl)-3-cephem-4-carboxylic acid.

This procedure may be desirable as trihydrate of monosodium salt of 7-(2-aminomethylphenylacetamido)-3-(1-carboxymethyltetrazol-5-ylthiomethyl)-3-cephem-4-carboxylic acid is not as stable at elevated temperatures as is the free-acid 7-(2-aminomethylphenylacetamido)-3-(1-carboxymethyltetrazol-5-ylthiomethyl)-3-cephem-4-carboxylic acid (zwitterion) monohydrate.

With regard to the stability of 7-(o-amino-methylphenylacetamido)-3-(1-methyl-1,2,3,4-tetrazol-5-ylthiomethyl)-3-cephem-4-carboxylic acid solutions at room temperature and at pH 10.3 (the lowest pH able to dissolve 150 mg./ml.) an almost instantaneous 50% loss of bioactivity is noted. An additional 21% activity is lost in the next 30 minutes.

By contrast, a solution containing 125.0 mg./ml. of the trihydrate of monosodium salt of 7-(2-aminomethylphenylacetamido)-3-(1-carboxymethyltetrazol-5-ylthiomethyl)-3-cephem-4-carboxylic acid at pH 7.0 showed no significant loss at room temperature for at least 24 hours.

The compound entitled 7-(o-aminomethylphenylacetamido)-3-(1-methyl-1,2,3,4-tetrazol-5-ylthiomethyl)-3-cephem-4-carboxylic acid of example 1 and claim 2 of U.S. Pat. No. 3,766,175 is a very potent cephalosporin exhibiting a highly desirable spectrum of activity particularly against certain Gram-negative organisms. Unfortunately, this zwitterion exhibits quite a low solubility in water and particularly in the blood stream which means at about pH 7.2 or thereabouts. To be more specific, attempts to measure this solubility gave results in the range of about 1.0-3.0 mg./ml. in both buffered aqueous media and in dog urine at room temperature. The pH of fresh beagle dog urine is 7.6. This raises a question as to the possible toxic effect in man of the administration of this zwitterion because of the fact that it is assumed that it will precipitate in crystalline form in the kidneys as it is concentrated therein during excretion. This, in man, would be highly undesirable. Conventional attempts to solve this prospective problem by the use of ordinary water soluble forms and derivatives of 7-(o-aminomethylphenylacetamido)-3-(1-methyl-1,2,3,4-tetrazol-5-ylthiomethyl)-3-cephem-4-carboxylic acid have proven unsuccessful because of conversion in the body of the salt or derivative to the zwitterion which then exhibits its natural low solubility in aqueous media and the blood. It was an objective of the present invention to solve this problem without loss of the valuable biological activity of 7-(o-aminomethylphenylacetamido)-3-(1-methyl-1,2,3,4-tetrazol-5-ylthiomethyl)-3-cephem-4-carboxylic acid. After various failures the problem was solved by the provision according to the present invention of 7-(2-aminomethylphenylacetamido)-3-(1-carboxymethyltetrazol-5-ylthiomethyl)-3-cephem-4-carboxylic acid which has the desired properties. To be more specific a sample of 7-(2-aminomethylphenylacetamido)-3-(1-carboxymethyltetrazol-5-ylthiomethyl)-3-cephem-4-carboxylic acid in pH 7.0 phosphate buffer at 25° C. exhibited a solubility in mg./ml. greater than 15.3 and less than 13.6; in this instance the capacity of the buffer was not sufficient and the pH dropped to 6.48. Thus the 7-(2-aminomethylphenylacetamido)-3-(1-carboxymethyltetrazol-5-ylthiomethyl)-3-cephem-4-carboxylic acid provided by the present invention even in its zwitterionic form is too soluble in the blood stream to crystallize in the kidneys and thereby cause fear of toxic results in at least some patients.

In addition, as set forth above the combination of the lack of aqueous solubility presented a problem which was solved by the preparation of the trihydrate of monosodium salt of 7-(2-aminomethylphenylacetamido)-3-(1-carboxymethyltetrazol-5-ylthiomethyl)-3-cephem-4-carboxylic acid of the present invention which exhibits such solubility at pH's suitable for injection in man such as about pH 7 and still exhibits satisfactory solubility in the blood stream and the fluids in the kidney even if converted in the body to the zwitterionic form.

In accordance with the above, the advantage of the compounds of the instant invention is their improved water solubility as compared to many of the other compounds known in the art, and in addition, the generally superior blood levels the compounds achieve upon parenteral administration by the intramuscular route.

EXAMPLE 16

7-(2-aminomethylphenylacetamido)-7-methoxy-3-(1-carboxymethyltetrazol-5-ylthiomethyl)-3-cephem-4-carboxylic acid Substitution in the procedure of Example 1 for the 7-amino-3-(1-carboxymethyltetrazol-5-ylthiomethyl)-3-cephem-4-carboxylic acid used therein of an equimolar quantity of 7-amino-7-methoxy-3-(1-carboxymethyltetrazol-5-thiomethyl)-3-cephem-4-carboxylic acid produces the title compound.

EXAMPLE 17

Dipotassium 7-(D-α-hydroxyphenylacetamido)-3-(1-carboxyethyltetrazol-5-ylthiomethyl)-3-cephem-4-carboxylate A solution of 1.5 g (0.0039 mole) of D-(−)-α-formyloxyphenylacetyl chloride in 20 ml. of acetone was added at 5° C. to a cold solution of 1.6 g (0.008 mole) of 7-amino-3-(1-carboxyethyltetrazol-5-ylthiomethyl)-3-cephem-4-carboxylic acid and 2.1 g of sodium bicarbonate in 25 ml of water. The solution was stirred for one hour and the acetone was removed at reduced pressure and layered with 50 ml of ethyl acetate. The mixture was acidified to pH 2 with 1:1 phosphoric acid. The ethyl acetate was washed with water, azeotroped to dryness at 15 mm pressure and the residue was slurried with ether. The product was collected and dried in vacuo over $P_2O_5$ to give 500 mg of product; m.p. >140° C. with decomp.

Anal. Calc'd. for $C_{21}H_{20}N_6O_8S_2.(C_2H_5)_2O$: C, 48.23; H, 4.84; N, 13.49. Found: C, 48.12; H, 4.31; N, 12.02.

The IR and NMR spectra were consistent with the structure. When this compound was administered intramuscularly by injection at a dose of 10 mg/kg of body weight in mice, a blood level of 16.0 mg/ml was obtained at 15 minutes.

EXAMPLE 18

Dipotassium 7-(D-α-hydroxyphenylacetamido)-7-methoxy-3-(1-carboxymethyltetrazol-5-yl-thiomethyl)-3-cephem-4-carboxylate Substitution in the procedure of example 2 for the 7-amino-3-(1-carboxymethyltetrazol-5-ylthiomethyl)-3-cephem-4-carboxylic acid used therein of an equimolar quantity of 7-amino-3-(1-carboxypentyltetrazol-5-ylthiomethyl)-3-cephem-4-carboxylic acid produces the title compound.

EXAMPLE 19

7-(D-α-Aminophenylacetamido)-7-methoxy-3-(1-carboxymethyltetrazol-5-ylthiomethyl)-3-cephem-4-carboxylic acid Substitution in the procedure of example 3 for the 7-amino-3-(1-carboxymethyltetrazol-5-ylthiomethyl)-3-cephem-4-carboxylic acid used therein of an equimolar quantity of 7-amino-7-methoxy-3-(1-carboxymethyltetrazol-5-yl-thiomethyl)-3-cephem-4-carboxylic acid produces the title compound.

EXAMPLE 20

7-(D-α-aminophenylacetamido)-3-(1-carboxy[$C_{1-9}$-alkyl]tetrazol-5-ylthiomethyl)-3-cephem-4-carboxylic acids Substitution in the procedure of example 3 for the 7-amino-3-(1-carboxymethyltetrazol-5-thiomethyl)-3-cephem-4-carboxylic acid used therein of the appropriate 7-amino-3-(1-carboxy[$C_{1-9}$alkyl]tetrazol-5-ylthiomethyl)-3-cephem-4-carboxylic acid, e.g., 7-amino-3-(1-carboxypropyltetrazol-5-ylthiomethyl)-3-cephem-4-carboxylic acid, 7-amino-3-(1-carboxybutyltetrazol-5-ylthiomethyl)-3-cephem-4-carboxylic acid, and the like, produces the corresponding title compound.

EXAMPLE 21

7-(2-aminomethyl-1,4-cyclohexadienylacetamido)-3-(1-carboxyethyltetrazol-5-ylthiomethyl)-3-cephem-4-carboxylic acid Substitution in the procedure of example 4 for the 7-amino-3-(1-carboxymethyltetrazol-5-yl-thiomethyl)-3-cephem-4-carboxylic acid used therein of 7-amino-3-(1-carboxyethyltetrazol-5-ylthiomethyl)-3-cephem-4-carboxylic acid produces the title compound.

EXAMPLE 22

7-(α-amino-4-hydroxyphenylacetamido)-3-(1-carboxyethyltetrazol-5-yl-thiomethyl)-3-cephem-4-carboxylic acid Substitution in the procedure of example 5 for the 7-amino-3-(1-carboxymethyltetrazol-5-yl-thiomethyl)-3-cephem-4-carboxylic acid used therein of b 7-amino-3-(1-carboxyethyltetrazol-5-ylthiomethyl)-3-cephem-4-carboxylic acid produces the title compound.

EXAMPLE 23

7-(3-aminomethyl-2-thienylacetamido)-3-(1-carboxymethyltetrazol-5-ylthiomethyl)-3-cephem-4-carboxylic acid (A)
7-(3-t-butoxycarbonylaminomethyl-2-thienylacetamido)-3-(1-carboxymethyltetrazol-5-ylthiomethyl)3-cephem-4-carboxylic acid A mixture of 3-t-butoxycarbonyl-aminomethyl-2-thienyl acetic acid (542 mg, 2 mmoles), 2,4-dinitrophenol (368 mg., 2 mmoles) and dicyclohexylcarbodiimide (412 mg., 2 mmoles) in tetrahydrofuran (THF) was stirred at room temperature for 1.5 hrs. The precipitated urea was removed and the filtrate was evaporated under reduced pressure. The resulting active ester (1.0 g) was dissolved in 10 ml of THF and added to a mixture of 7-amino-3-(1-carboxymethyl or tetrazol-5-ylthiomethyl-3-cephem-4-carboxylic acid (656 mg, 2 m moles) and triethylamine (816 mg, 8 m moles) in water (5 ml) at 0° C. with stirring. Stirring was continued for 3.5 hrs. at room temperature and the reaction mixture was added to water (20 ml and washed with ether (4×20 ml). The aqueous solution was layered with ethyl acetate and adjusted to pH 2 with conc. HCl at 5° C. The organic layer was separated and the aqueous layer extracted with ethyl acetate (2×50 ml). The ethyl acetate extracts were combined, washed with saturated aqueous sodium chloride, dried over $HgSO_4$ and evaporated under reduced pressure. The residual oil was chromatographed on silica gel (10 g). The column was developed successively with chloroform (150 ml) and 3% methanol-chloroform (100 ml). From the chloroform eluate 2,4-dinitrophenol (50 mg) was recovered and the title cephalosporin was isolated by evaporation of the methanol-chloroform eluate.

Yield: 29%; m.p. 185°–188° C. with decomposition.

Anal. Calc'd. for $C_{23}H_{27}N_7O_8S_3$: C, 42.91; H, 4.54; N, 15.23; S, 14.94. Found: C 43.02; H, 4.17; N, 15.07; S, 15.04.

(B)

7-(3-Aminomethyl-2-thienylacetamido)-3-(1-carboxymethyltetrazol-5-ylthiomethyl)-3-cephem-4-carboxylic acid Trifluoracetic acid (0.6 ml) was added to the blocked cephalosporin obtained in step A (610 mg., 1.05 mmoles) and 0° C. and the mixture stirred at room temperature for 15 mins. To the reaction mixture was added anhydrous ether (15 ml) to separate precipitate, which was collected by filtration, washed with anhydrous ether (2×10 ml) and dissolved in acetonitrile (10 ml). To the solution was added 2 drops of conc. ammonium hydroxide. The separated solid was collected by filtration, washed with acetonitrile (2×10 ml) and dried at 75° C./1 mmHg for 7 hrs. to afford the title product, which was collected as the monoammonium salt after treatment with one equivalent of ammonium hydroide.

Yield: 83%; m.p. 174°–178° C. with decomposition.

Anal. Calc'd. for $C_{18}H_{21}N_8O_6S_3.H_2O$: C, 38.56; H, 4.32; N, 19.98; S, 17.16. Found: C, 38.89; H, 4.06; N, 18.83; S, 15.24.

The IR and NMR were consistent with the structure.

EXAMPLE 24

7-(3-aminomethyl-2-thienylacetamido)-3-(1-carboxyethyltetrazol-5-ylthiomethyl)-3-cephem-4-carboxylic acid Substitution in the procedure of example 23 for the 7-amino-3-(1-carboxymethyltetrazol-5-ylthiomethyl)3-cephem-4-carboxylic acid used therein of an equimolar quantity of 7-amino-3-(1-carboxyethyltetrazol-5-ylthiomethyl)-3-cephem-4-carboxylic acid produces the title compound.

EXAMPLE 25

7-(3-Aminomethyl-2-thienylacetamido)-7-methoxy-3-(1-carboxymethyltetrazol-5-ylthiomethyl)-3-cephem-4-carboxylic acid Substitution in the procedure of example 23 for the 7-amino-3-(1-carboxymethyltetrazol-5-ylthiomethyl)3-cephem-4-carboxylic acid used therein of an equimolar quantity of 7-amino-7-methoxy-3-(1-carboxymethyltetrazol-5-ylthiomethyl)-3-cephem-4-carboxylic acid produces the title compound.

EXAMPLE 26

7-(2-aminomethylphenylacetamido)-3-(1-carboxyethyl-tetrazol-2-ylthiomethyl)-3-cephem-4-carboxylic acid (A)

Potassium-O-(1-carbomethoxy-propen-2-ylaminomethyl)-phenylacetate (Enamine)

1. Put 1000 g of O-aminomethylphenylacetic acid, 340 g of potassium hydroxide, 1412 g of methyl acetoacetate and 32,400 ml of absolute methanol into a tank.[1]

2. Heat the mixture to reflux for 4 hours while stirring.

3. Concentrate the reaction solution under reduced pressure at <50° C. to about 1/5 of the starting volume.[2]

4. Add 10,000 ml of MIBK to the concentrate and continue the concentration at reduced pressure until the methanol is removed.

5. Add 10,000 ml of MIBK or any amount necessary to make a workable slurry of the concentrate.

6. Stir and cool the mixture to 5°–10° C. for 30 minutes.

7. Filter the slurry and wash the cake with 5000 ml of MIBK and then 5000 ml of acetone.[3]

8. Dry the produce in an air circulating oven at ~40° C.

9. The yield is 1605–1680 g or 88–92% of white crystalline product. MP=140°–142° C.

(B)

7-(2-Aminomethylphenylacetamide)-3-(1-carboethyl-tetrazol-2-thiomethyl)-3-cephem-4-carboxylic acid (A[1]) Enamine (4.09 g) from step A and 90 ml of tetrahydrofuran were mixed in a 3-neck flask equipped with a stirrer, drying tube and cooled in a dry-ice acetone bath. Eight drops of N,N-dimethylbenzylamine was added and the mixture was cooled to −38° C. Isobutylchloroformate (1.95 g) was added and stirred for 15 minutes.

(B[1]) 7-amino-3(1-carboxyethyltetrazol-2-ylthiomethyl)-3-cephem-4-carboxylic acid (3.5 g) was dissolved in 50 ml of water and 2.29 g of N-methylmorpholine and cooled to 2° C. The anhydride from step A[1] was added to the solution with stirring. The mixture was stirred for 1.5 hours at 2° C. The tetrahydrofuran was removed in vacuo, the remainder layered with ethyl acetate and adjusted to pH 3. After stirring in an ice bath, the product was collected; 250 mg. M.P. 140 $\overline{c}$ decomposition.

The IR and NMR were consistent with the title product, but indicated about 20% impurities, primarily starting material. When this compound was administered intramuscularly by injection at a dose of 10 mg/kg of body weight in mice, a blood level of 22.3 mg/ml was obtained at 15 minutes.

EXAMPLE 27

Substitution in the procedure of example 2 for the D-(−)-2-formyloxy-2-phenylacetyl chloride used therein of an equimolar quantity of a D-mandelic acid carboxyanhydride prepared from the following D-mandelic acids by treating the mandelic acid with phosgene as described supra.

D-2-chloro-mandelic acid,
D-3-chloro-mandelic acid,
D-4-chloro-mandelic acid,
D-2-bromo-mandelic acid,
D-3-bromo-mandelic acid,
D-4-bromo-mandelic acid,
D-2-fluoro-mandelic acid,
D-3-fluoro-mandelic acid,
D-4-fluoro-mandelic acid,
D-2-trifluoromethyl-mandelic acid,
D-3-trifluoromethyl-mandelic acid,
D-4-trifluoromethyl-mandelic acid,
D-2-amino-mandelic acid,
D-3-amino-mandelic acid,
D-4-amino-mandelic acid,
D-2-nitro-mandelic acid,
D-3-nitro-mandelic acid,
D-4-nitro-mandelic acid, D-2-hydroxy-mandelic acid,
D-3-hydroxy-mandelic acid,
D-4-hydroxy-mandelic acid,
D-2-methyl-mandelic acid,
D-3-methyl-mandelic acid,
D-4-methyl-mandelic acid,
D-2-methoxy-mandelic acid,
D-3-methoxy-mandelic acid,
D-4-methoxy-mandelic acid respectively produces the
Dipotassium 7-(d-mandelamido)-3-(1-carboxymethyltetrazol-5-ylthiomethyl)-3-cephem-4-carboxylate,
Dipotassium 7-(D-2-chloro-mandelamido)-3-(1-carboxymethyltetrazol-5-ylthiomethyl)-3-cephem-4-carboxylate,
Dipotassium 7-(D-3-chloro-mandelamido)-3-(1-carboxymethyltetrazol-5-ylthiomethyl)-3-cephem-4-carboxylate,
Dipotassium 7-(D-4-chloro-mandelamido)-3-(1-carboxymethyltetrazol-5-ylthiomethyl)-3-cephem-4-carboxylate,
Dipotassium 7-(D-2-bromo-mandelamido)-3-(carboxymethyltetrazol-5-ylthiomethyl)-3-cephem-4-carboxylate,
Dipotassium 7-(D-3-bromo-mandelamido)-3-(1-carboxymethyltetrazol-5-ylthiomethyl)-3-cephem-4-carboxylate,
Dipotassium 7-(D-4-bromo-mandelamido)-3-(1-carboxymethyltetrazol-5-ylthiomethyl)-3-cephem-4-carboxylate,
Dipotassium 7-(D-2-fluoro-mandelamido)-3-(1-carboxymethyltetrazol-5-ylthiomethyl)-3-cephem-4-carboxylate,
Dipotassium 7-(D-3-fluoro-mandelamido)-3-(1-carboxymethyltetrazol-5-ylthiomethyl)-3-cephem-4-carboxylate,
Dipotassium 7-(D-4-fluoro-mandelamido)-3-(1-carboxymethyltetrazol-5-ylthiomethyl)-3-cephem-4-carboxylate,
Dipotassium 7-(D-2-trifluoromethyl-mandelamido)-3-(1-carboxymethyltetrazol-5-ylthiomethyl)-3-cephem-4-carboxylate,
Dipotassium 7-(D-3-trifluoromethyl-mandelamido)-3-(1-carboxymethyltetrazol-5-ylthiomethyl)-3-cephem-4-carboxylate,
Dipotassium 7-(D-4-trifluoromethyl-mandelamido)-3-(1-carboxymethyltetrazol-5-ylthiomethyl)-3-cepehm-4-carboxylate,
Dipotassium 7-(D-2-amino-mandelamido)-3-(1-carboxymethyltetrazol-5-ylthiomethyl)-3-cephem-4-carboxylate,
Dipotassium 7-(D-3-amino-mandelamido)-3-(1-carboxymethyltetrazol-5-ylthiomethyl)-3-cephem-4-carboxylate,
Depotassium 7-(D-4-amino-mandelamido)-3-(1-carboxymethyltetrazol-5-ylthiomethyl)-3-cephem-4-carboxylate,
Depotassium 7-(D-2-nitro-mandelamido)-3-(1-carboxymethyltetrazol-5-ylthiomethyl)-3-cephem-4-carboxylate,
Dipotassium 7-(D-3-nitro-mandelamido)-3-(1-carboxymethyltetrazol-5-ylthiomethyl)-3-cephem-4-carboxylate,
Dipotassium 7-(D-4-nitro-mandelamido)-3-(1-carboxymethyltetrazol-5-ylthiomethyl)-3-cephem-4-carboxylate,
Dipotassium 7-(D-2-hydroxy-mandelamido)-3-(1-carboxymethyltetrazol-5-ylthiomethyl)-3-cephem-4-carboxylate,
Dipotassium 7-(D-3-hydroxy-mandelamido)-3-(1-carboxymethyltetrazol-5-ylthiomethyl)-3-cephem-4-carboxylate,
Dipotassium 7-(D-4-hydroxy-mandelamido)-3-(1-carboxymethyltetrazol-5-ylthiomethyl)-3-cephem-4-carboxylate,
Dipotassium 7-(D-α-formyloxyphenylacetamido)-3-(1-carboxymethyltetrazol-5-ylthiomethyl)-3-cephem-4-carboxylate,
Dipotassium 7-(D-2-methyl-mandelamido)-3-(1-carboxymethyltetrazol-4-ylthiomethyl)-3-cephem-4-carboxylate,
Dipotassium 7-(D-3-methyl-mandelamido)-3-(1-carboxymethyltetrazol-5-ylthiomethyl)-3-cephem-4-carboxylate,
Dipotassium 7-(D-4-methyl-mandelamido)-3-(1-carboxymethyltetrazol-5-ylthiomethyl)-3-cephem-4-carboxylate,
Dipotassium 7-(D-2-methoxy-mandelamido)-3-(1-carboxymethyltetrazol-5-ylthiomethyl)-3-cephem-4-carboxylate,
Dipotassium 7-(D-3-methoxy-mandelamido)-3-(1-carboxymethyltetrazol-5-ylthiomethyl)-3-cephem-4-carboxylate and
Dipotassium 7-(D-4-methoxy-mandelamido)-3-(1-carboxymethyltetrazol-5-ylthiomethyl)-3-cephem-4-carboxylate respectively.

EXAMPLE 28

7β-(o-N-t-Butoxycarbonylaminomethylphenylacetamido)-7α-methoxy-3-(1-carboxymethyltetrazol-5-ylthiomethyl)-3-cephem-4-carboxylic acid

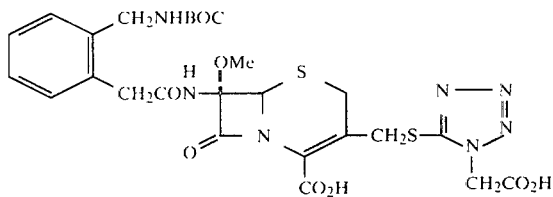

A mixture of 7β-(O-N-t-butoxycarbonylaminomethylphenylacetamido)-7α-methoxycephalosporanic acid (549 mg, 1 mmol), sodium bicarbonate (84 mg., 1 mmol) and 1-carboxymethyl-5-mercaptotetrazole disodium salt (816 mg., 4 mmol) in 0.1 M pH 7.0 phosphate buffer (5 ml) was heated for 1 hr. at 85° C. After cooling, the mixture was acidified to pH 1 with di 1. HCl and extracted with ethyl acetate (3×30 ml). The combined extracts were washed with water, dried and evaporated under reduced pressure to afford an oily residue which was chromatographed on a silica gel column (Wako-gel, C-200, 10 g). The column was eluted with chloroformmethanol (50:1). The first eluate (100 ml) contained the starting mercaptan (0.30 g). The second eluate (50 ml) containing the desired product was treated with a small amount of carbon and evaporated under reduced pressure to give the title product as amorphous powder (140 mg, 22%); m.p. 110°–120° C. (dec.).

IR: $\nu_{max}^{KBr}$ 3600–2400, 1780, 1690, 1520, 1385, 1250, 1160 cm$^{-1}$.

UV: $\lambda_{max}^{EtOH}$ 246 nm (ε 6300), 274 nm (ε 6700).

NMR:$\delta_{ppm}^{DMSO-d_6}$ 1.35 (9H, s, t-Bu-H), 3.38 (3H, s, OCH$_3$), 3.65 (2H, s, CH$_2$CO), 4.13 (1H, d, 14 Hz, 3-H, 4.16 (2H, d, 6 Hz, a singlet with D$_2$O, CH$_2$N), 4.50 (1H, d, 14 Hz, 3-H), 5.01 (1H, s, 6-H), 5.26 (2H, s, tetrazolCH₂CO), 7.20 (4H, s, phenyl-H), 9.20 (1H, s, CONH, disappeared by addition of D₂O).

Anal. calc'd. for $C_{26}H_{31}N_7O_9S_2.2H_2O$: C, 45.54; H, 5.14; N, 14.30. Found: C, 45.71, 45.73; H, 4.51, 4.42; N, 13.65, 13.91.

EXAMPLE 29

7β-(o-Aminomethylphenylacetamido)-7α-methoxy-3-(1-carboxymethyltetrazol-5-ylthiomethyl)-3-cephem-4-carboxylic acid

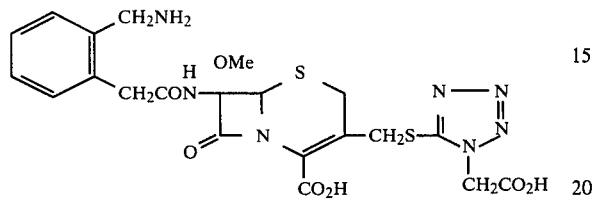

A cold mixture of the product obtained in example 28 (120 mg., 0.18 mmol) and trifluoroacetic acid (TFA) (0.3 ml) was stirred at room temperature for 20 mins. to give a viscous solution. The addition of ether (20 ml) to the solution gave the TFA salt of the product, which was collected by filtration and dissolved in acetonitrile-water (50:1, 20 ml). The solution was treated with a small amount of carbon. A mixture of conc. NH₄OH-acetonitrile (1:2) was added dropwise in the filtrate with stirring until no more precipitation occurred. The gummy precipitate was collected and triturated in acetonitrile (20 ml) to afford the title product, which was collected by filtration, washed with acetonitrile (5 ml) and dried. Yield 62 mg (63%); m.p. 185°–190° C. (dec.).

IR: $\nu_{max}^{KBr}$ 3600–2600, 1700, 1605, 1380, 1300, 1110, 1085 cm⁻¹.

UV: $\lambda_{max}^{1\%NaHCO_3}$ 238 nm (ε 8300), 270 nm (ε 9100).

Anal. calc'd. for $C_{21}H_{23}N_7O_7S_2.\tfrac{1}{2}H_2O$: C 45.15; H, 4.23; N, 17.55. Found: C, 45.26; H, 4.81; N, 18.51.

We claim:

1. A compound of the formula

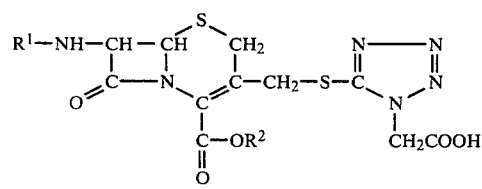

wherein R² is hydrogen, pivaloyloxymethyl, acetoxymethyl, methoxymethyl, acetonyl, phenacyl, p-nitrobenzyl, β,β,β-trichloroethyl, 3-phthalidyl or 5-indanyl and having the D configuration in the 7-side chain wherein R¹ has the structure

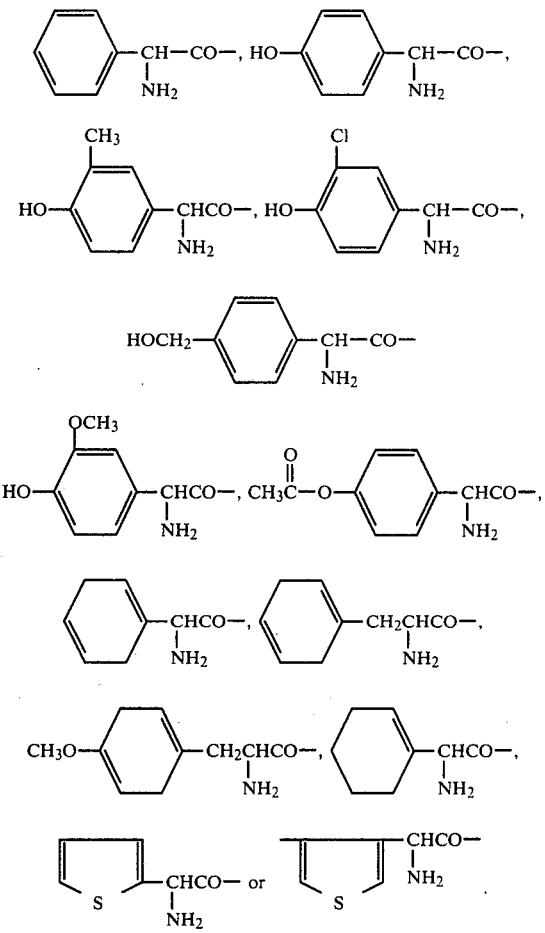

2. A nontoxic pharmaceutically acceptable salt of a compound of claim 1.

3. The compound of claim 1 having the D configuration in the 7-side chain and the formula

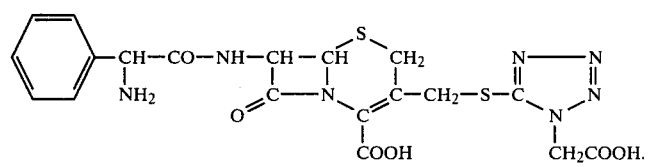

4. The compound of claim 1 having the D configuration in the 7-side chain and the formula

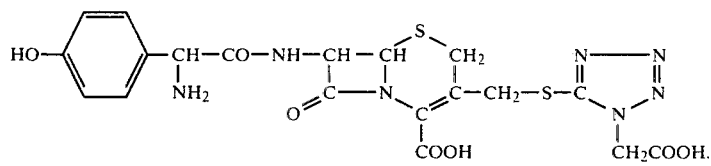

5. The compound of claim 1 having the D configuration in the 7-side chain and the formula

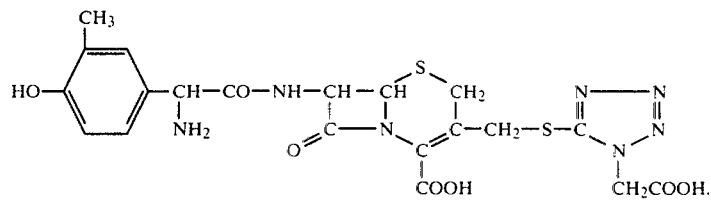

6. The compound of claim 1 having the D configuration in the 7-side chain and the formula

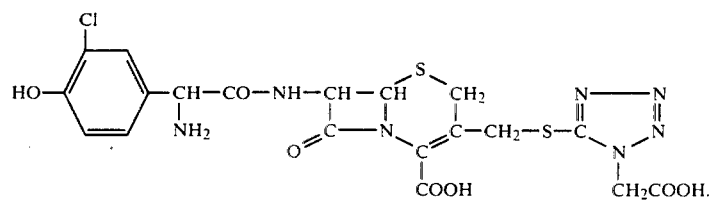

7. The compound of claim 1 having the D configuration in the 7-side chain and the formula

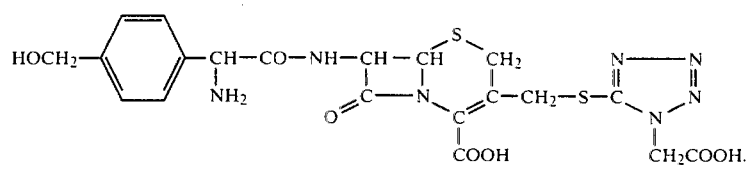

8. The compound of claim 1 having the D configuration in the 7-side chain and the formula

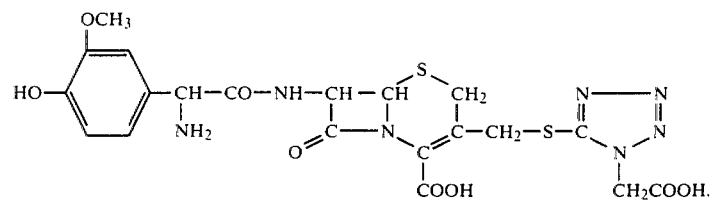

9. The compound of claim 1 having the D configuration in the 7-side chain and the formula

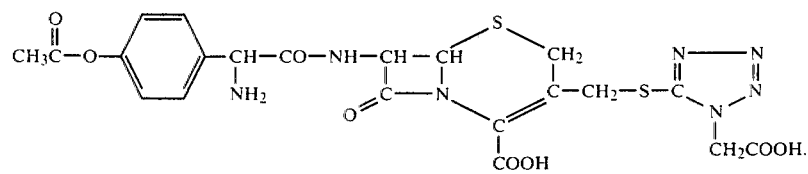

10. The compound of claim 1 having the D configuration in the 7-side chain and the formula

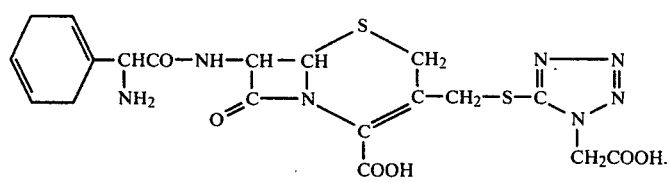

11. The compound of claim 1 having the D configuration in the 7-side chain and the formula

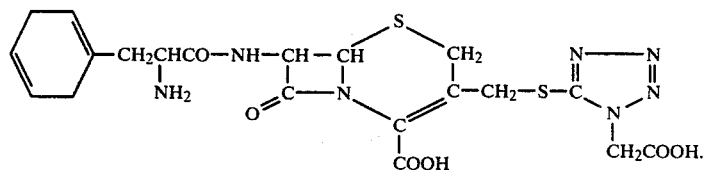

12. The compound of claim 1 having the D configuration in the 7-side chain and the formula

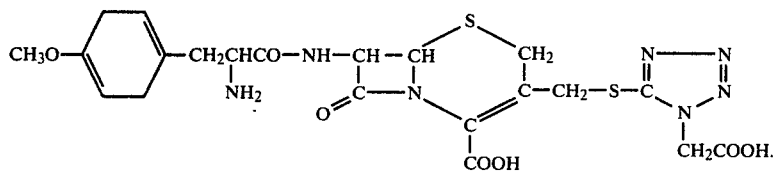

13. The compound of claim 1 having the D configuration in the 7-side chain and the formula

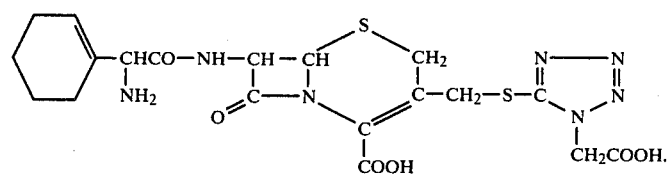

14. The compound of claim 1 having the D configuration in the 7-side chain and the formula

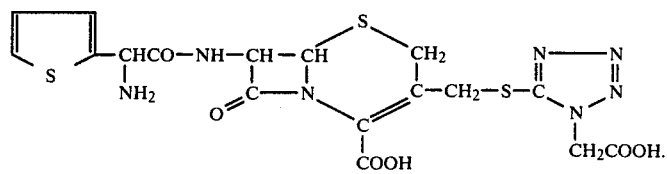

15. The compound of claim 1 having the D configuration in the 7-side chain and the formula

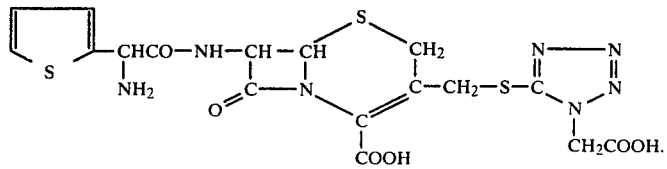

* * * * *